US00RE40089E

(19) United States
(12) Reissued Patent
Boon-Falleur et al.

(10) Patent Number: US RE40,089 E
(45) **Date of Reissued Patent: *Feb. 19, 2008**

(54) NUCLEIC ACID MOLECULES ENCODING THE MAGE-1 TUMOR REJECTION ANTIGEN PRECURSOR

(75) Inventors: Thierry Boon-Falleur, Brussels (BE); Pierre Van der Bruggen, Brussels (BE); Benoit Van den Eynde, Brussels (BE); Aline Van Pel, Brussels (BE); Etienne De Plaen, Brussels (BE); Christophe Lurquin, Brussels (BE); Patrick Chomez, Brussels (BE); Catia Traversari, Milan (IT)

(73) Assignee: Ludwig Institute for Cancer Research, New York, NY (US)

( * ) Notice: This patent is subject to a terminal disclaimer.

(21) Appl. No.: 08/590,097

(22) Filed: Jan. 24, 1996

Related U.S. Patent Documents

Reissue of:
(64) Patent No.: 5,342,774
Issued: Aug. 30, 1994
Appl. No.: 07/807,043
Filed: Dec. 12, 1991

U.S. Applications:
(63) Continuation-in-part of application No. 07/764,365, filed on Sep. 23, 1991, now abandoned, which is a continuation-in-part of application No. 07/728,838, filed on Jul. 9, 1991, now abandoned, which is a continuation-in-part of application No. 07/705,702, filed on May 23, 1991, now abandoned.

(51) Int. Cl.
*C12N 15/12* (2006.01)
*C12N 15/10* (2006.01)
*C12N 15/00* (2006.01)
*C12N 15/63* (2006.01)

(52) U.S. Cl. ..... 536/23.5; 536/23.1; 435/252.3; 435/320.1; 435/325

(58) Field of Classification Search ..... 435/69.3, 435/252.3, 320.1, 371, 325, 362, 367, 69.1, 435/440, 455, 466, 471, 476, 488, 235.1; 536/23.5, 23.1; 530/350; 935/9, 32, 34, 57, 935/62, 70, 71, 72, 73
See application file for complete search history.

(56) References Cited

U.S. PATENT DOCUMENTS 5,141,742 A * 8/1992 Brown et al. ..... 424/88
5,506,126 A * 4/1996 Seed et al.
5,843,448 A * 12/1998 Chen et al.
6,235,525 B1 * 5/2001 van den Eynde et al.
6,498,021 B1 * 12/2002 Guagler ..... 435/69.1
6,552,180 B1 * 4/2003 Guagler et al. ..... 536/23.5
6,946,289 B1 * 9/2005 Guagler et al. ..... 435/325

OTHER PUBLICATIONS

Brasseur et al., Int. J. Cancer 52: 839–841 (1992).*
Boon, Int. J. Cancer 54: 177–180 (1993).*
Kirkin et al., Apmus 106: 665–679 (1998).*
De Plaen et al., Immunogenetics 40: 360–369 (1994).*
Stevenson, Faseb J 5: 2250–2257 (1991).*
Boon et al., Cancer Cells 1: 25–28 (1989).*
Ding et al., Biochem Biophys Res Commun 202: 549–555 (1994).*
Skolnick, Trends in Biotech 18: 34–39 (2000).*
Boilk, Genome Research 10: 398–400 (2000).*
Smith et al., Nature Biotechnology 15: 1222–1123 (1997).*
Van Den Eynde et al., Int. J. Cancer 44: 634–640 (1989).*
De Plaen et al., PNAS 85: 2274–2278 (1988).*
Traversari et al., J. Exp. Med vol. 176 pp. 1453–1457, 1993.*
Boar Scientific American Mar. 1993 pp. 82–89.*
Sibille et al. J. Exp. Med. 172:35–45, 1990.*
Van der Bruggen et al. Science 254:1643–1647, 1991.*
Knuth et al Proc Natl Acad. Sci USA 86:2804–2808, 1989.*
Zakut et al. Cancer Research 53:5–8, 1993.*
Morgan et al. Cancer Research 43: 3155–3159, 1983.*
Gupta et al. Cancer Research 39:1683–1695, 1979.*
Lurquin et al. Cell, 58:293–303 1989.*
Bon et al. J. Exp. Med. 152: 1184–1193, 1980.*
Liao et al. Int. J. Cancer, 30:573–580, 1982.*
Wong et al. J. of Surgical Research 48:539–546, 1990.*
Gupta et al. JNCI 72: 75–82, 1984.*
Ricchetti et al. EMBO J 9(5): 1583–93 (see abstract), May 1990.*
Burgess et al. J. Cell Biology 111:2129–38, Nov. 1990.*
Lazar et al. Molecular and Cellular Biology 8(3): 1247–52, Mar. 1988.*

* cited by examiner

*Primary Examiner*—Phillip Gambel
(74) *Attorney, Agent, or Firm*—Fulbright & Jaworski

(57) ABSTRACT

The invention relates to an isolated DNA sequence which codes for an antigen expressed by tumor cells which is recognized by cytotoxic T cells, leading to lysis of the tumor which expresses it. Also described are cells transfected by the DNA sequence, and various therapeutic and diagnostic uses arising out of the properties of the DNA and the antigen for which it codes.

19 Claims, 32 Drawing Sheets

```
ACCACAGGAG AATGAAAAGA ACCCGGGACT CCCAAAGACG CTAGATGTGT GAAGATCCTG
ATCACTCATT GGGTGTCTGA GTTCTGCGAT ATTCATCCCT CAGCCAATGA GCTTACTGTT
CTCGTGGGGG GTTTGTGAGC CTTGGGTAGG AAGTTTTGCA AGTTCCGCCT ACAGCTCTAG
CTTGTGAATT TGTACCCTTT CACGTAAAAA AGTAGTCCAG AGTTTACTAC ACCCTCCCTC
CCCCCTCCCA CCTCGTGCTG TGCTGAGTTT AGAAGTCTTC CTTATAGAAG TCTTCCGTAT
AGAACTCTTC CGGAGGAAGG AGGGAGGACC CCCCCCCTTT GCTCTCCCAG CATGCATTGT
GTCAACGCCA TTGCACTGAG CTGGTCGAAG AAGTAAGCCG CTAGCTTGCG ACTCTACTCT
TATCTTAACT TAGCTCGGCT TCCTGCTGGT ACCCTTTGTG CC
```

Fig. 6A

```
ATG TCT GAT AAC AAG AAA CCA GAC AAA GCC CAC AGT GGC TCA GGT GGT
Met Ser Asp Asn Lys Lys Pro Asp Lys Ala His Ser Gly Ser Gly Gly
                 5                  10                  15
GAC GGT GAT GGG AAT AGG TGC AAT TTA TTG CAC CGG TAC TCC CTG GAA
Asp Gly Asp Gly Asn Arg Cys Asn Leu Leu His Arg Tyr Ser Leu Glu
            20                  25                  30
GAA ATT CTG CCT TAT CTA GGG TGG CTG GTC TTC GCT GTT GTC ACA ACA
Glu Ile Leu Pro Tyr Leu Gly Trp Leu Val Phe Ala Val Val Thr Thr
        35                  40                  45
AGT TTT CTG GCG CTC CAG ATG TTC ATA GAC GCC CTT TAT GAG GAG CAG
Ser Phe Leu Ala Leu Gln Met Phe Ile Asp Ala Leu Tyr Glu Glu Gln
    50                  55                  60
TAT GAA AGG GAT GTG GCC TGG ATA GCC AGG CAA AGC AAG CGC ATG TCC
Tyr Glu Arg Asp Val Ala Trp Ile Ala Arg Gln Ser Lys Arg Met Ser
65                  70                  75                  80
TCT GTC GAT GAG GAT GAA GAC GAT GAG GAT GAT GAG GAT GAC TAC TAC
Ser Val Asp Glu Asp Glu Asp Asp Glu Asp Asp Glu Asp Asp Tyr Tyr
                85                  90                  95
GAC GAC GAG GAC GAC GAC GAC GAT GCC TTC TAT GAT GAT GAG GAT GAT
Asp Asp Glu Asp Asp Asp Asp Asp Ala Phe Tyr Asp Asp Glu Asp Asp
            100                 105                 110
GAG GAA GAA GAA TTG GAG AAC CTG ATG GAT GAT GAA TCA GAA GAT GAG
Glu Glu Glu Glu Leu Glu Asn Leu Met Asp Asp Glu Ser Glu Asp Glu
        115                 120                 125
GCC GAA GAA GAG ATG AGC GTG GAA ATG GGT GCC GGA GCT GAG GAA ATG
Ala Glu Glu Glu Met Ser Val Glu Met Gly Ala Gly Ala Glu Glu Met
    130                 135                 140
GGT GCT GGC GCT AAC TGT GCC TGT GTT CCT GGC CAT CAT TTA AGG AAG
Gly Ala Gly Ala Asn Cys Ala Cys Val Pro Gly His His Leu Arg Lys
145                 150                 155                 160
AAT GAA GTG AAG TGT AGG ATG ATT TAT TTC TTC CAC GAC CCT AAT TTC
Asn Glu Val Lys Cys Arg Met Ile Tyr Phe Phe His Asp Pro Asn Phe
                165                 170                 175
CTG GTG TCT ATA CCA GTG AAC CCT AAG GAA CAA ATG GAG TGT AGG TGT
Leu Val Ser Ile Pro Val Asn Pro Lys Glu Gln Met Glu Cys Arg Cys
            180                 185                 190
GAA AAT GCT GAT GAA GAG GTT GCA ATG GAA GAG GAA GAA GAA GAA GAG
Glu Asn Ala Asp Glu Glu Val Ala Met Glu Glu Glu Glu Glu Glu Glu
        195                 200                 210
GAG GAG GAG GAG GAA GAG GAA ATG GGA AAC CCG GAT GGC TTC TCA CCT
Glu Glu Glu Glu Glu Glu Glu Met Gly Asn Pro Asp Gly Phe Ser Pro
220                 225                 230                 235

TAG
```

Fig. 6B

GCATGCAGTT GCAAAGCCCA GAAGAAAGAA ATGGACAGCG GAAGAAGTGG TTGTTTTTTT
TTCCCCTTCA TTAATTTTCT AGTTTTTAGT AATCCAGAAA ATTTGATTTT GTTCTAAAGT
TCATTATGCA AAGATGTCAC CAACAGACTT CTGACTGCAT GGTGAACTTT CATATGATAC
ATAGGATTAC ACTTGTACCT GTTAAAAATA AAAGTTTGAC TTGCATAC

Fig. 6C

ACCACAGGAG AATGAAAAGA ACCCGGGACT CCCAAAGACG CTAGATGTGT
GAAGATCCTG ATCACTCATT GGGTGTCTGA GTTCTGCGAT ATTCATCCCT
CAGCCAATGA GCTTACTGTT CTCGTGGGGG GTTTGTGAGC CTTGGGTAGG
AAGTTTTGCA AGTTCCGCCT ACAGCTCTAG CTTGTGAATT TGTACCCTTT
CACGTAAAAA AGTAGTCCAG AGTTTACTAC ACCCTCCCTC CCCCCTCCCA
CCTCGTGCTG TGCTGAGTTT AGAAGTCTTC CTTATAGAAG TCTTCCGTAT
AGAACTCTTC CGGAGGAAGG AGGGAGGACC CCCCCCCTTT GCTCTCCCAG
CATGCATTGT GTCAACGCCA TTGCACTGAG CTGGTCGAAG AAGTAAGCCG
CTAGCTTGCG ACTCTACTCT TATCTTAACT TAGCTCGGCT TCCTGCTGGT
ACCCTTTGTG CC
ATG TCT GAT AAC AAG AAA CCA GAC AAA GCC CAC AGT GGC TCA
GGT GGT GAC GGT GAT GGG AAT AGG TGC AAT TTA TTG CAC CGG
TAC TCC CTG GAA GAA ATT CTG CCT TAT CTA GGG TGG CTG GTC
TTC GCT GTT GTC ACA ACA AGT TTT CTG GCG CTC CAG ATG TTC
ATA GAC GCC CTT TAT GAG GAG CAG TAT GAA AGG GAT GTG GCC
TGG ATA GCC AGG CAA AGC AAG CGC ATG TCC TCT GTC GAT GAG
GAT GAA GAC GAT GAG GAT GAT GAG GAT GAC TAC TAC GAC GAC
GAG GAC GAC GAC GAC GAT GCC TTC TAT GAT GAT GAG GAT GAT
GAG GAA GAA GAA TTG GAG AAC CTG ATG GAT GAT GAA TCA GAA
GAT GAG GCC GAA GAA GAG ATG AGC GTG GAA ATG GGT GCC GGA
GCT GAG GAA ATG GGT GCT GGC GCT AAC TGT GCC TGT GTT CCT
GGC CAT CAT TTA AGG AAG AAT GAA GTG AAG TGT AGG ATG ATT
TAT TTC TTC CAC GAC CCT AAT TTC CTG GTG TCT ATA CCA GTG
AAC CCT AAG GAA CAA ATG GAG TGT AGG TGT GAA AAT GCT GAT
GAA GAG GTT GCA ATG GAA GAG GAA GAA GAA GAA GAG GAG GAG
GAG GAG GAA GAG GAA ATG GGA AAC CCG GAT GGC TTC TCA CCT
TAG
GCATGCAGTT GCAAAGCCCA GAAGAAAGAA ATGGACAGCG GAAGAAGTGG
TTGTTTTTTT TTCCCCTTCA TTAATTTTCT AGTTTTTAGT AATCCAGAAA
ATTTGATTTT GTTCTAAAGT TCATTATGCA AAGATGTCAC CAACAGACTT
CTGACTGCAT GGTGAACTTT CATATGATAC ATAGGATTAC ACTTGTACCT
GTTAAAAATA AAAGTTTGAC TTGCATAC

Fig. 6D

ACCACAGGAG AATGAAAAGA ACCCGGGACT CCCAAAGACG CTAGATGTGT
GAAGATCCTG ATCACTCATT GGGTGTCTGA GTTCTGCGAT ATTCATCCCT
CAGCCAATGA GCTTACTGTT CTCGTGGGGG GTTTGTGAGC CTTGGGTAGG
AAGTTTTGCA AGTTCCGCCT ACAGCTCTAG CTTGTGAATT TGTACCCTTT
CACGTAAAAA AGTAGTCCAG AGTTTACTAC ACCCTCCCTC CCCCCTCCCA
CCTCGTGCTG TGCTGAGTTT AGAAGTCTTC CTTATAGAAG TCTTCCGTAT
AGAACTCTTC CGGAGGAAGG AGGGAGGACC CCCCCCCTTT GCTCTCCCAG
CATGCATTGT GTCAACGCCA TTGCACTGAG CTGGTCGAAG AAGTAAGCCG
CTAGCTTGCG ACTCTACTCT TATCTTAACT TAGCTCGGCT TCCTGCTGGT
ACCCTTTGTG CC

ATG TCT GAT AAC AAG AAA CCA GAC AAA GCC CAC AGT GGC TCA
GGT GGT GAC GGT GAT GGG AAT AGG TGC AAT TTA TTG CAC CGG
TAC TCC CTG GAA GAA ATT CTG CCT TAT CTA GGG TGG CTG GTC
TTC GCT GTT GTC ACA ACA AGT TTT CTG GCG CTC CAG ATG TTC
ATA GAC GCC CTT TAT GAG GAG CAG TAT GAA AGG GAT GTG GCC
TGG ATA GCC AGG CAA AGC AAG CGC ATG TCC TCT GTC GAT GAG
GAT GAA GAC GAT GAG GAT GAT GAG GAT GAC TAC TAC GAC GAC
GAG GAC GAC GAC GAC GAT GCC TTC TAT GAT GAT GAG GAT GAT
GAG GAA GAA GAA TTG GAG AAC CTG ATG GAT GAT GAA TCA GAA
GAT GAG GCC GAA GAA GAG ATG AGC GTG GAA ATG GGT GCC GGA
GCT GAG GAA ATG GGT GCT GGC GCT AAC TGT GCC T

GTGAGTAACC CGTGGTCTTT ACTCTAGATT CAGGTGGGGT GCATTCTTTA
CTCTTGCCCA CATCTGTAGT AAAGACCACA TTTTGGTTGG GGGTCATTGC
TGGAGCCATT CCTGGCTCTC CTGTCCACGC CTATCCCCGC TCCTCCCATC
CCCCACTCCT TGCTCCGCTC TCTTTCCTTT TCCCACCTTG CCTCTGGAGC
TTCAGTCCAT CCTGCTCTGC TCCCTTTCCC CTTTGCTCTC CTTGCTCCCC
TCCCCCTCGG CTCAACTTTT CGTGCCTTCT GCTCTCTGAT CCCCACCCTC
TTCAGGCTTC CCCATTTGCT CCTCTCCCGA AACCCTCCCC TTCCTGTTCC
CCTTTTCGCG CCTTTTCTTT CCTGCTCCCC TCCCCCTCCC TATTTACCTT
TCACCAGCTT TGCTCTCCCT GCTCCCCTCC CCCTTTTGCA CCTTTTCTTT
TCCTGCTCCC CTCCCCCTCC CCTCCCTGTT TACCCTTCAC CGCTTTTCCT
CTACCTGCTT CCCTCCCCCT TGCTGCTCCC TCCCTATTTG CATTTTCGGG
TGCTCCTCCC TCCCCCTCCC CCTCCCTCCC TATTTGCATT TTCGGGTGCT
CCTCCCTCCC CCTCCCCAGG CCTTTTTTTT TTTTTTTTTT TTTTTTTTTT
TTGGTTTTTC GAGACAGGGT TTCTCTTTGT ATCCCTGGCT GTCCTGGCAC
TCACTCTGTA GACCAGGCTG GCCTCAAACT CAGAAATCTG CCTGCCTCTG
CCTCCCAAAT GCTGGGATTA AAGGCTTGCA CCAGGACTGC CCCAGTGCAG
GCCTTTCTTT TTTCTCCTCT CTGGTCTCCC TAATCCCTTT TCTGCATGTT
AACTCCCCTT TTGGCACCTT TCCTTTACAG GACCCCCTCC CCCTCCCTGT
TTCCCTTCCG GCACCCTTCC TAGCCCTGCT CTGTTCCCTC TCCCTGCTCC
CCTCCCCCTC TTTGCTCGAC TTTTAGCAGC CTTACCTCTC CCTGCTTTCT
GCCCCGTTCC CCTTTTTTGT GCCTTTCCTC CTGGCTCCCC TCCACCTTCC
AGCTCACCTT TTTGTTTGTT TGGTTGTTTG GTTGTTTGGT TTGCTTTTTT
TTTTTTTTTT GCACCTTGTT TTCCAAGATC CCCCTCCCCC TCCGGCTTCC
CCTCTGTGTG CCTTTCCTGT TCCCTCCCCC TCGCTGGCTC CCCCTCCCTT
TCTGCCTTTC CTGTCCCTGC TCCCTTCTCT GCTAACCTTT TAATGCCTTT
CTTTTCTAGA CTCCCCCCTC CAGGCTTGCT GTTTGCTTCT GTGCACTTTT

Fig. 9A

CCTGACCCTG CTCCCCTTCC CCTCCCAGCT CCCCCCTCTT TTCCCACCTC
CCTTTCTCCA GCCTGTCACC CCTCCTTCTC TCCTCTCTGT TTCTCCCACT
TCCTGCTTCC TTTACCCCTT CCCTCTCCCT ACTCTCCTCC CTGCCTGCTG
GACTTCCTCT CCAGCCGCCC AGTTCCCTGC AGTCCTGGAG TCTTTCCTGC
CTCTCTGTCC ATCACTTCCC CCTAGTTTCA CTTCCCTTTC ACTCTCCCCT
ATGTGTCTCT CTTCCTATCT ATCCCTTCCT TTCTGTCCCC TCTCCTCTGT
CCATCACCTC TCTCCTCCCT TCCCTTTCCT CTCTCTTCCA TTTTCTTCCA
CCTGCTTCTT TACCCTGCCT CTCCCATTGC CCTCTTACCT TTATGCCCAT
TCCATGTCCC CTCTCAATTC CCTGTCCCAT TGTGCTCCCT CACATCTTCC
ATTTCCCTCT TTCTCCCTTA GCCTCTTCTT CCTCTTCTCT TGTATCTCCC
TTCCCTTTGC TTCTCCCTCC TCCTTTCCCC TTCCCCTATG CCCTCTACTC
TACTTGATCT TCTCTCCTCT CCACATACCC TTTTTCCTTT CCACCCTGCC
CTTTGTCCCC AGACCCTACA GTATCCTGTG CACAGGAAGT GGGAGGTGCC
ATCAACAACA AGGAGGCAAG AAACAGAGCA AAATCCCAAA ATCAGCAGGA
AAGGCTGGAT GAAAATAAGG CCAGGTTCTG AGGACAGCTG GAATCTAGCC
AAGTGGCTCC TATAACCCTA AGTACCAAGG GAGAAAGTGA TGGTGAAGTT
CTTGATCCTT GCTGCTTCTT TTACATATGT TGGCACATCT TTCTCAAATG
CAGGCCATGC TCCATGCTTG GCGCTTGCTC AGCGTGGTTA AGTAATGGGA
GAATCTGAAA ACTAGGGGCC AGTGGTTTGT TTTGGGGACA AATTAGCACG
TAGTGATATT TCCCCCTAAA AATTATAACA AACAGATTCA TGATTTGAGA
TCCTTCTACA GGTGAGAAGT GGAAAAATTG TCACTATGAA GTTCTTTTTA
GGCTAAAGAT ACTTGGAACC ATAGAAGCGT TGTTAAAATA CTGCTTTCTT
TTGCTAAAAT ATTCTTTCTC ACATATTCAT ATTCTCCAG
GT GTT CCT GGC CAT CAT TTA AGG AAG AAT GAA GTG AAG TGT
AGG ATG ATT TAT TTC TTC CAC GAC CCT AAT TTC CTG GTG TCT
ATA CCA GTG AAC CCT AAG GAA CAA ATG GAG TGT AGG TGT GAA
AAT GCT GAT GAA GAG GTT GCA ATG GAA GAG GAA GAA GAA GAA
GAG GAG GAG GAG GAG GAA GAG GAA ATG GGA AAC CCG GAT GGC
TTC TCA CCT TAG
GCATGCAGGT ACTGGCTTCA CTAACCAACC ATTCCTAACA TATGCCTGTA
GCTAAGAGCA TCTTTTTAAA AAATATTATT GGTAAACTAA ACAATTGTTA
TCTTTTTACA TTAATAAGTA TTAAATTAAT CCAGTATACA GTTTTAAGAA
CCCTAAGTTA AACAGAAGTC AATGATGTCT AGATGCCTGT TCTTTAGATT
GTAGTGAGAC TACTTACTAC AGATGAGAAG TTGTTAGACT CGGGAGTAGA
GACCAGTAAA AGATCATGCA GTGAAATGTG GCCATGGAAA TCGCATATTG
TTCTTATAGT ACCTTTGAGA CAGCTGATAA CAGCTGACAA AAATAAGTGT
TTCAAGAAAG ATCACACGCC ATGGTTCACA TGCAAATTAT TATTTTGTCG
TTCTGATTTT TTTCATTTCT AGACCTGTGG TTTTAAAGAG ATGAAAATCT
CTTAAAATTT CCTTCATCTT TAATTTTCCT TAACTTTAGT TTTTTTCACT
TAGAATTCAA TTCAAATTCT TAATTCAATC TTAATTTTTA GATTTCTTAA
AATGTTTTTT AAAAAAAATG CAAATCTCAT TTTTAAGAGA TGAAAGCAGA
GTAACTGGGG GGCTTAGGGA ATCTGTAGGG TTGCGGTATA GCAATAGGGA
GTTCTGGTCT CTGAGAAGCA GTCAGAGAGA ATGGAAAACC AGGCCCTTGC
CAGTAGGTTA GTGAGGTTGA TATGATCAGA TTATGGACAC TCTCCAAATC
ATAAATACTC TAACAGCTAA GGATCTCTGA GGGAAACACA ACAGGGAAAT
ATTTTAGTTT CTCCTTGAGA AACAATGACA AGACATAAAA TTGGCAAGAA
AGTCAGGAGT GTATTCTAAT AAGTGTTGCT TATCTCTTAT TTTCTTCTAC
AGTTGCAAAG CCCAGAAGAA AGAAATGGAC AGCGGAAGAA GTGGTTGTTT
TTTTTTCCCC TTCATTAATT TTCTAGTTTT TAGTAATCCA GAAAATTTGA
TTTTGTTCTA AAGTTCATTA TGCAAAGATG TCACCAACAG ACTTCTGACT
GCATGGTGAA CTTTCATATG ATACATAGGA TTACACTTGT ACCTGTTAAA
AATAAAAGTT TGACTTGCAT AC

Fig. 9B

Leu-Pro-Tyr-Leu-Gly-Trp-Leu

FIG. 12

```
MAGE-3 III  CCTCCCCAGAGTCCTCAGGGAGCCTCCagCcTcCCCACTACCATgAACTaCcCTCtctgGAGcCAAtCCtaTGAGGacTCCAGCAaCCaaGAAGAGGAGG
                                                                          <------------ CHO-3
MAGE-2 II   CCTCCCCAcAGTCCTCAGGGAGCCTCCagCTTctCgACTACCATCAACTaCACTCtttgGAGaCAAtCCgaTGAGGGcTCCAGCAaCCaaGAAGAGGAGG
                                                                          <------------ CHO-2
MAGE-1 I    CCTCCCCAGAGTCCTCAGGGAGCCTCCGCCTTTCCCACTACCATCAACTTCACTCGACAGAGGCAACCCAGTGAGGGTTCCAGCAGCCGTGAAGAGGAGG
            225  CHO-8 ---------->

III         GGCCAAGCACCTtcccTgaCC-TGGAGTCCgaGTTCCaAGCAGcAcTCAgTAgGAAGGTGGCcGAgTTGGTTcaTTTTCTGCTCCTCAAgTATCGAGCCA
II          GGCCAAGaAtgTtTcccgaCCtTGGAGTCCGAGTTCCaAGCAGcAATCAgTAgGAAGaTGGtTGAgTTGGTTcaTTTTCTGCTCCTCAAgTATCGAGCCA
I           GGCCAAGCACCTCTTGTATCC-TGGAGTCCTTGTTCCGAGCAGTAATCACTAAGAAGGTGGCTGATTTGGTTGGTTTTCTGCTCCTCAAATATCGAGCCA
            325

III         GGGAGCCgGTCACAAAGGCAGAAATGCTGGgGAGTGTCgTCggAAATTggcAGtAtTtcTTTCCTGtGATCTTCaGCAAAGCtTCcagtTCCTTGCAGCT
II          GGGAGCCgGTCACAAAGGCAGAAATGCTGGAGAGTGTCcTCAgAAATTgCcAGgACTtcTTTCCcGtGATCTTCaGCAAAGCCTCcGAGTaCTTGCAGCT
I           GGGAGCCAGTCACAAAGGCAGAAATGCTGGAGAGTGTCATCAAAAATTACAAGCACTGTTTTCCTGAGATCTTCGGCAAAGCCTCTGAGTCCTTGCAGCT
            425                                                                <------------ SEQ-4

III         GGTCTTTGGCATcGAgcTGAtGGAAGtgGACCCCAtCGGCCACTtgTAcaTCtTTGcCACCTGCCTgGGcCTCTCCTAcGATGGCCTGCTGGGTGAcAAT
II          GGTCTTTGGCATcGAgGTGgtGGAAGtgGtCCCCAtCaGCCACTtgTAcaTCCTTGTCACCTGCCTgGGcCTCTCCTAcGATGGCCTGCTGGGcGAcAAT
I           GGTCTTTGGCATTGACGTGAAGGAAGCAGACCCCACCGGCCACTCCTATGTCCTTGTCACCTGCCTAGGTCTCTCCTATGATGGCCTGCTGGGTGATAAT
            525

III         CAGATCATGCCCAAGgCAGGCcTCCTGATAATcGTCCTGGcCATaATcGCAAgaGAGGGCGaCtgTGCcCCTGAGGAGaAAATCTGGGAGGAGCTGAGTG
II          CAGgTCATGCCCAAGACAGGCcTCCTGATAATcGTC-TGGcCATaATcGCAATaGAGGGCGaCtgTGCcCCTGAGGAGaAAATCTGGGAGGAGCTGAGTa
I           CAGATCATGCCCAAGACAGGCTTCCTGATAATTGTCCTGGTCATGATTGCAATGGAGGGCGGCCATGCTCCTGAGGAGGAAATCTGGGAGGAGCTGAGTG
            625                                                                                <------------ CHO-9
```

FIG. 14A

| | | EXPRSSION OF MAGE GENE FAMILY | | | | RECOGNITIN BY ANI-E CTL tested by: | | |
|---|---|---|---|---|---|---|---|---|
| | | Northern blot probed with cross-reactive MAGE-1 probe* | cDNA-PCR product probed with oligonucleotide specific for: MAGE-1 | MAGE-2 | MAGE-3† | TNF release‡ | Lysis§ | Expression of antigen MZ2-E after transfection** |
| Cells of patient MZ2 | melanoma cell line MZ2-MEL.3.0 | + | ++++ | ++++ | ++++ | + | + | |
| | tumor sample MZ2 (1982) | + | +++ | +++ | +++ | | | |
| | antigen-loss variant MZ2-MEL.2.2 | + | – | +++ | +++ | – | – | |
| | CTL clone MZ2-CTL.82/30 | – | – | – | – | | | |
| | PHA-activated blood lymphocytes | – | – | – | – | | | |
| Normal tissues | Liver | – | – | – | – | | | |
| | Muscle | – | – | – | – | | | |
| | Skin | – | – | – | – | | | |
| | Lung | – | – | – | – | | | |
| | Brain | – | – | – | – | | | |
| | Kidney | – | – | – | – | | | |
| Melanoma cell lines of HLA-A1 patients | LB34-MEL | + | ++ | ++++ | ++++ | + | +– | |
| | MI665/2-MEL | – | – | – | – | – | – | + |
| | MI10221-MEL | + | – | ++ | +++ | – | – | + |
| | MI13443-MEL | + | +++ | ++++ | ++++ | + | + | |
| | SK33-MEL | + | – | ++++ | ++++ | – | – | – |
| | SK23-MEL | + | – | ++++ | ++++ | – | – | + |

* Data obtained in the conditions of figure 5.
† Data obtained as described in figure 6.
‡ TNF release by CTL 82/30 after stimulation with the tumor cells as described in (11).
§ Lysis of 51 Cr labelled target by CTL 82/30 in the conditions of figure 1.
** Cells transfected with the 2.4 kb fragment of gene MAGE-1 were tested for their ability fo stimulate TNF release by CTL 82/30

FIG. 14B

| | | EXPRSSION OF MAGE GENE FAMILY | | | | RECOGNITIN BY ANI-E CTL tested by: | | |
|---|---|---|---|---|---|---|---|---|
| | | Northern blot probed with cross-reactive MAGE-1 probe* | cDNA-PCR product probed with oligonucleotide specific for: MAGE-1 | MAGE-2 | MAGE-3† | TNF release‡ | Lysis§ | Expression of antigen MZ2-E after transfection** |
| Melanoma cell lines of other patients | LB17-MEL | + | + | ++++ | ++++ | – | – | – |
| | LB33-MEL | + | – | +++ | +++ | – | – | – |
| | LB4-MEL | – | – | – | – | – | – | |
| | LB41-MEL | – | – | – | – | – | – | |
| | MI4024-MEL | + | +++ | ++++ | ++++ | – | – | |
| | SK29-MEL | – | – | – | – | – | – | |
| | MZ3-MEL | + | + | ++++ | ++++ | – | – | |
| | MZ5-MEL | + | – | ++++ | ++++ | – | – | |
| Melanoma tumor sample | BB5-MEL | + | +++ | ++ | +++ | | | |
| Other tumor cell lines | small cell lung cancer H209 | + | – | ++++ | ++++ | | | |
| | small cell lung cancer H345 | + | – | ++++ | ++++ | | | |
| | small cell lung cancer H510 | + | – | ++++ | ++++ | | | |
| | small cell lung cancer LB11 | + | + | ++++ | ++++ | | | |
| | bronchial squamous cell carcinoma LB37 | + | – | – | +++ | | | |
| | thyroid medullary carcinoma TT | + | ++++ | +++ | ++++ | | | |
| | colon carcinoma LB31 | + | – | +++ | ++++ | | | |
| | colon carcinoma LS411 | – | – | – | – | – | | |
| Other tumor samples | chronic myeloid leukemia LLC5 | – | – | – | – | | | |
| | acute myeloid leukemia TA | – | – | – | – | | | |

* Data obtained in the conditions of figure 5.
† Data obtained as described in figure 6.
‡ TNF release by CTL 82/30 after stimulation with the tumor cells as described in (11).
§ Lysis of 51 Cr labelled target by CTL 82/30 in the conditions of figure 1.
** Cells transfected with the 2.4 kb fragment of gene MAGE-1 were tested for their ability fo stimulate TNF release by CTL 82/30

FIG. 17A

CCCGGGGCAC CACTGGCATC CCTCCCCCTA CCACCCCCAA TCCCTCCCTT
TACGCCACCC ATCCAAACAT CTTCACGCTC ACCCCCAGCC CAAGCCAGGC
AGAATCCGGT TCCACCCCTG CTCTCAACCC AGGGAAGCCC AGGTGCCCAG
ATGTGACGCC ACTGACTTGA GCATTAGTGG TTAGAGAGAA GCGAGGTTTT
CGGTCTGAGG GGCGGCTTGA GATCGGTGGA GGGAAGCGGG CCCAGCTCTG
TAAGGAGGCA AGGTGACATG CTGAGGGAGG ACTGAGGACC CACTTACCCC
AGATAGAGGA CCCCAAATAA TCCCTTCATG CCAGTCCTGG ACCATCTGGT
GGTGGACTTC TCAGGCTGGG CCACCCCCAG CCCCCTTGCT GCTTAAACCA
CTGGGGACTC GAAGTCAGAG CTCCGTGTGA TCAGGGAAGG GCTGCTTAGG
AGAGGGCAGC GTCCAGGCTC TGCCAGACAT CATGCTCAGG ATTCTCAAGG
AGGGCTGAGG GTCCCTAAGA CCCCACTCCC GTGACCCAAC CCCCACTCCA
ATGCTCACTC CCGTGACCCA ACCCCCTCTT CATTGTCATT CCAACCCCCA
CCCCACATCC CCCACCCCAT CCCTCAACCC TGATGCCCAT CCGCCCAGCC
ATTCCACCCT CACCCCCACC CCCACCCCCA CGCCCACTCC CACCCCCACC
CAGGCAGGAT CCGGTTCCCG CCAGGAAACA TCCGGGTGCC CGGATGTGAC
GCCACTGACT TGCGCATTGT GGGGCAGAGA GAAGCGAGGT TTCCATTCTG
AGGGACGGCG TAGAGTTCGG CCGAAGGAAC CTGACCCAGG CTCTGTGAGG
AGGCAAGGTG AGAGGCTGAG GGAGGACTGA GGACCCCGCC ACTCCAAATA
GAGAGCCCCA AATATTCCAG CCCCGCCCTT GCTGCCAGCC CTGGCCCACC
CGCGGGAAGA CGTCTCAGCC TGGGCTGCCC CCAGACCCCT GCTCCAAAAG
CCTTGAGAGA CACCAGGTTC TTCTCCCCAA GCTCTGGAAT CAGAGGTTGC
TGTGACCAGG GCAGGACTGG TTAGGAGAGG GCAGGGCACA GGCTCTGCCA
GGCATCAAGA TCAGCACCCA AGAGGGAGGG CTGTGGGCCC CCAAGACTGC
ACTCCAATCC CCACTCCCAC CCCATTCGCA TTCCCATTCC CCACCCAACC
CCCATCTCCT CAGCTACACC TCCACCCCCA TCCCTACTCC TACTCCGTCA
CCTGACCACC ACCCTCCAGC CCCAGCACCA GCCCCAACCC TTCTGCCACC
TCACCCTCAC TGCCCCCAAC CCCACCCTCA TCTCTCTCAT GTGCCCCACT
CCCATCGCCT CCCCCATTCT GGCAGAATCC GGTTTGCCCC TGCTCTCAAC
CCAGGGAAGC CCTGGTAGGC CCGATGTGAA ACCACTGACT TGAACCTCAC
AGATCTGAGA GAAGCCAGGT TCATTTAATG GTTCTGAGGG GCGGCTTGAG
ATCCACTGAG GGGAGTGGTT TTAGGCTCTG TGAGGAGGCA AGGTGAGATG
CTGAGGGAGG ACTGAGGAGG CACACACCCC AGGTAGATGG CCCCAAAATG
ATCCAGTACC ACCCCTGCTG CCAGCCCTGG ACCACCCGGC CAGGACAGAT
GTCTCAGCTG GACCACCCCC CGTCCCGTCC CACTGCCACT TAACCCACAG
GGCAATCTGT AGTCATAGCT TATGTGACCG GGGCAGGGTT GGTCAGGAGA
GGCAGGGCCC AGGCATCAAG GTCCAGCATC CGCCCGGCAT TAGGGTCAGG
ACCCTGGGAG GGAACTGAGG GTTCCCCACC CACACCTGTC TCCTCATCTC
CACCGCCACC CCACTCACAT TCCCATACCT ACCCCCTACC CCCAACCTCA
TCTTGTCAGA ATCCCTGCTG TCAACCCACG GAAGCCACGG GAATGGCGGC
CAGGCACTCG GATCTTGACG TCCCCATCCA GGGTCTGATG GAGGGAAGGG
GCTTGAACAG GGCCTCAGGG GAGCAGAGGG AGGGCCCTAC TGCGAGATGA
GGGAGGCCTC AGAGGACCCA GCACCCTAGG ACACCGCACC CCTGTCTGAG
ACTGAGGCTG CCACTTCTGG CCTCAAGAAT CAGAACGATG GGGACTCAGA
TTGCATGGGG GTGGGACCCA GGCCTGCAAG GCTTACGCGG AGGAAGAGGA
GGGAGGACTC AGGGGACCTT GGAATCCAGA TCAGTGTGGA CCTCGGCCCT
GAGAGGTCCA GGGCACGGTG GCCACATATG GCCCATATTT CCTGCATCTT
TGAGGTGACA GGACAGAGCT GTGGTCTGAG AAGTGGGGCC TCAGGTCAAC
AGAGGGAGGA GTTCCAGGAT CCATATGGCC CAAGATGTGC CCCCTTCATG

FIG. 17B

AGGACTGGGG ATATCCCCGG CTCAGAAAGA AGGGACTCCA CACAGTCTGG
CTGTCCCCTT TTAGTAGCTC TAGGGGGACC AGATCAGGGA TGGCGGTATG
TTCCATTCTC ACTTGTACCA CAGGCAGGAA GTTGGGGGGC CCTCAGGGAG
ATGGGGTCTT GGGGTAAAGG GGGGATGTCT ACTCATGTCA GGGAATTGGG
GGTTGAGGAA GCACAGGCGC TGGCAGGAAT AAAGATGAGT GAGACAGACA
AGGCTATTGG AATCCACACC CCAGAACCAA AGGGGTCAGC CCTGGACACC
TCACCCAGGA TGTGGCTTCT TTTTCACTCC TGTTTCCAGA TCTGGGGCAG
GTGAGGACCT CATTCTCAGA GGGTGACTCA GGTCAACGTA GGGACCCCCA
TCTGGTCTAA AGACAGAGCG GTCCCAGGAT CTGCCATGCG TTCGGGTGAG
GAACATGAGG GAGGACTGAG GGTACCCCAG GACCAGAACA CTGAGGGAGA
CTGCACAGAA ATCAGCCCTG CCCCTGCTGT CACCCCAGAG AGCATGGGCT
GGGCCGTCTG CCGAGGTCCT TCCGTTATCC TGGGATCATT GATGTCAGGG
ACGGGGAGGC CTTGGTCTGA GAAGGCTGCG CTCAGGTCAG TAGAGGGAGC
GTCCCAGGCC CTGCCAGGAG TCAAGGTGAG GACCAAGCGG GCACCTCACC
CAGGACACAT TAATTCCAAT GAATTTTGAT ATCTCTTGCT GCCCTTCCCC
AAGGACCTAG GCACGTGTGG CCAGATGTTT GTCCCCTCCT GTCCTTCCAT
TCCTTATCAT GGATGTGAAC TCTTGATTTG GATTTCTCAG ACCAGCAAAA
GGGCAGGATC CAGGCCCTGC CAGGAAAAAT ATAAGGGCCC TGCGTGAGAA
CAGAGGGGGT CATCCACTGC ATGAGAGTGG GGATGTCACA GAGTCCAGCC
CACCCTCCTG GTAGCACTGA GAAGCCAGGG CTGTGCTTGC GGTCTGCACC
CTGAGGGCCC GTGGATTCCT CTTCCTGGAG CTCCAGGAAC CAGGCAGTGA
GGCCTTGGTC TGAGACAGTA TCCTCAGGTC ACAGAGCAGA GGATGCACAG
GGTGTGCCAG CAGTGAATGT TTGCCCTGAA TGCACACCAA GGGCCCCACC
TGCCACAGGA CACATAGGAC TCCACAGAGT CTGGCCTCAC CTCCCTACTG
TCAGTCCTGT AGAATCGACC TCTGCTGGCC GGCTGTACCC TGAGTACCCT
CTCACTTCCT CCTTCAGGTT TTCAGGGGAC AGGCCAACCC AGAGGACAGG
ATTCCCTGGA GGCCACAGAG GAGCACCAAG GAGAAGATCT GTAAGTAGGC
CTTTGTTAGA GTCTCCAAGG TTCAGTTCTC AGCTGAGGCC TCTCACACAC
TCCCTCTCTC CCCAGGCCTG TGGGTCTTCA TTGCCCAGCT CCTGCCCACA
CTCCTGCCTG CTGCCCTGAC GAGAGTCATC

ATG TCT CTT GAG CAG AGG AGT CTG CAC TGC AAG CCT GAG GAA
GCC CTT GAG GCC CAA CAA GAG GCC CTG GGC CTG GTG TGT GTG
CAG GCT GCC ACC TCC TCC TCC TCT CCT CTG GTC CTG GGC ACC
CTG GAG GAG GTG CCC ACT GCT GGG TCA ACA GAT CCT CCC CAG
AGT CCT CAG GGA GCC TCC GCC TTT CCC ACT ACC ATC AAC TTC
ACT CGA CAG AGG CAA CCC AGT GAG GGT TCC AGC AGC CGT GAA
GAG GAG GGG CCA AGC ACC TCT TGT ATC CTG GAG TCC TTG TTC
CGA GCA GTA ATC ACT AAG AAG GTG GCT GAT TTG GTT GGT TTT
CTG CTC CTC AAA TAT CGA GCC AGG GAG CCA GTC ACA AAG GCA
GAA ATG CTG GAG AGT GTC ATC AAA AAT TAC AAG CAC TGT TTT
CCT GAG ATC TTC GGC AAA GCC TCT GAG TCC TTG CAG CTG GTC
TTT GGC ATT GAC GTG AAG GAA GCA GAC CCC ACC GGC CAC TCC
TAT GTC CTT GTC ACC TGC CTA GGT CTC TCC TAT GAT GGC CTG
CTG GGT GAT AAT CAG ATC ATG CCC AAG ACA GGC TTC CTG ATA
ATT GTC CTG GTC ATG ATT GCA ATG GAG GGC GGC CAT GCT CCT
GAG GAG GAA ATC TGG GAG GAG CTG AGT GTG ATG GAG GTG TAT
GAT GGG AGG GAG CAC AGT GCC TAT GGG GAG CCC AGG AAG CTG
CTC ACC CAA GAT TTG GTG CAG GAA AAG TAC CTG GAG TAC CGG
CAG GTG CCG GAC AGT GAT CCC GCA CGC TAT GAG TTC CTG TGG
GGT CCA AGG GCC CTC GCT GAA ACC AGC TAT GTG

FIG. 17C

GCATGAGTTG CAGCCAAGGC CAGTGGGAGG GGGACTGGGC CAGTGCACCT
TCCAGGGCCG CGTCCAGCAG CTTCCCCTGC CTCGTGTGAC ATGAGGCCCA
TTCTTCACTC TGAAGAGAGC GGTCAGTGTT CTCAGTAGTA GGTTTCTGTT
CTATTGGGTG ACTTGGAGAT TTATCTTTGT TCTCTTTTGG AATTGTTCAA
ATGTTTTTTT TTAAGGGATG GTTGAATGAA CTTCAGCATC CAAGTTTATG
AATGACAGCA GTCACACAGT TCTGTGTATA TAGTTTAAGG GTAAGAGTCT
TGTGTTTTAT TCAGATTGGG AAATCCATTC TATTTTGTGA ATTGGGATAA
TAACAGCAGT GGAATAAGTA CTTAGAAATG TGAAAAATGA GCAGTAAAAT
AGATGAGATA AAGAACTAAA GAAATTAAGA GATAGTCAAT TCTTGCCTTA
TACCTCAGTC TATTCTGTAA AATTTTTAAA GATATATGCA TACCTGGATT
TCCTTGGCTT CTTTGAGAAT GTAAGAGAAA TTAAATCTGA ATAAAGAATT
CTTCCTGTTC ACTGGCTCTT TTCTTCTCCA TGCACTGAGC ATCTGCTTTT
TGGAAGGCCC TGGGTTAGTA GTGGAGATGC TAAGGTAAGC CAGACTCATA
CCCACCCATA GGGTCGTAGA GTCTAGGAGC TGCAGTCACG TAATCGAGGT
GGCAAGATGT CCTCTAAAGA TGTAGGGAAA AGTGAGAGAG GGGTGAGGGT
GTGGGGCTCC GGGTGAGAGT GGTGGAGTGT CAATGCCCTG AGCTGGGGCA
TTTTGGGCTT TGGGAAACTG CAGTTCCTTC TGGGGGAGCT GATTGTAATG
ATCTTGGGTG GATCC

CCCATCCAGA TCCCCATCCG GGCAGAATCC GGTTCCACCC TTGCCGTGAA
CCCAGGGAAG TCACGGGCCC GGATGTGACG CCACTGACTT GCACATTGGA
GGTCAGAGGA CAGCGAGATT CTCGCCCTGA GCAACGGCCT GACGTCGGCG
GAGGGAAGCA GGCGCAGGCT CCGTGAGGAG GCAAGGTAAG ACGCCGAGGG
AGGACTGAGG CGGGCCTCAC CCCAGACAGA GGGCCCCCAA TTAATCCAGC
GCTGCCTCTG CTGCCGGGCC TGGACCACCC TGCAGGGGAA GACTTCTCAG
GCTCAGTCGC CACCACCTCA CCCCGCCACC CCCCGCCGCT TTAACCGCAG
GGAACTCTGG CGTAAGAGCT TTGTGTGACC AGGGCAGGGC TGGTTAGAAG
TGCTCAGGGC CCAGACTCAG CCAGGAATCA AGGTCAGGAC CCCAAGAGGG
GACTGAGGGC AACCCACCCC CTACCCTCAC TACCAATCCC ATCCCCCAAC
ACCAACCCCA CCCCCATCCC TCAAACACCA ACCCCACCCC CAAACCCCAT
TCCCATCTCC TCCCCCACCA CCATCCTGGC AGAATCCGGC TTTGCCCCTG
CAATCAACCC ACGGAAGCTC CGGGAATGGC GGCCAAGCAC GCGGATCCTG
ACGTTCACAT GTACGGCTAA GGGAGGGAAG GGGTTGGGTC TCGTGAGTAT
GGCCTTTGGG ATGCAGAGGA AGGGCCCAGG CCTCCTGGAA GACAGTGGAG
TCCTTAGGGG ACCCAGCATG CCAGGACAGG GGGCCCACTG TACCCCTGTC
TCAAACTGAG CCACCTTTTC ATTCAGCCGA GGGAATCCTA GGGATGCAGA
CCCACTTCAG GGGGTTGGGG CCCAGCCTGC GAGGAGTCAA GGGGAGGAAG
AAGAGGGAGG ACTGAGGGGA CCTTGGAGTC CAGATCAGTG GCAACCTTGG
GCTGGGGGAT CCTGGGCACA GTGGCCGAAT GTGCCCCGTG CTCATTGCAC
CTTCAGGGTG ACAGAGAGTT GAGGGCTGTG GTCTGAGGGC TGGGACTTCA
GGTCAGCAGA GGGAGGAATC CCAGGATCTG CCGGACCCAA GGTGTGCCCC
CTTCATGAGG ACTCCCCATA CCCCCGGCCC AGAAAGAAGG GATGCCACAG
AGTCTGGAAG TAAATTGTTC TTAGCTCTGG GGGAACCTGA TCAGGGATGG
CCCTAAGTGA CAATCTCATT TGTACCACAG GCAGGAGGTT GGGGAACCCT
CAGGGAGATA AGGTGTTGGT GTAAAGAGGA GCTGTCTGCT CATTTCAGGG
GGTTCCCCCT TGAGAAAGGG CAGTCCCTGG CAGGAGTAAA GATGAGTAAC
CCACAGGAGG CCATCATAAC GTTCACCCTA GAACCAAAGG GGTCAGCCCT
GGACAACGCA CGTGGGGTAA CAGGATGTGG CCCCTCCTCA CTTGTCTTTC
CAGATCTCAG GGAGTTGATG ACCTTGTTTT CAGAAGGTGA CTCAGTCAAC
ACAGGGGCCC CTCTGGTCGA CAGATGCAGT GGTTCTAGGA TCTGCCAAGC
ATCCAGGTGG AGAGCCTGAG GTAGGATTGA GGGTACCCCT GGGCCAGAAT
GCAGCAAGGG GGCCCCATAG AAATCTGCCC TGCCCCTGCG GTTACTTCAG
AGACCCTGGG CAGGGCTGTC AGCTGAAGTC CCTCCATTAT CTGGGATCTT
TGATGTCAGG GAAGGGGAGG CCTTGGTCTG AAGGGGCTGG AGTCAGGTCA
GTAGAGGGAG GGTCTCAGGC CCTGCCAGGA GTGGACGTGA GGACCAAGCG
GACTCGTCAC CCAGGACACC TGGACTCCAA TGAATTTGAC ATCTCTCGTT
GTCCTTCGCG GAGGACCTGG TCACGTATGG CCAGATGTGG GTCCCCTCTA
TCTCCTTCTG TACCATATCA GGGATGTGAG TTCTTGACAT GAGAGATTCT
CAAGCCAGCA AAAGGGTGGG ATTAGGCCCT ACAAGGAGAA AGGTGAGGGC
CCTGAGTGAG CACAGAGGGG ACCCTCCACC CAAGTAGAGT GGGGACCTCA
CGGAGTCTGG CCAACCCTGC TGAGACTTCT GGGAATCCGT GGCTGTGCTT
GCAGTCTGCA CACTGAAGGC CCGTGCATTC CTCTCCCAGG AATCAGGAGC
TCCAGGAACC AGGCAGTGAG GCCTTGGTCT GAGTCAGTGC CTCAGGTCAC
AGAGCAGAGG GGACGCAGAC AGTGCCAACA CTGAAGGTTT GCCTGGAATG

Fig. 18A

CACACCAAGG GCCCCACCCG CCCAGAACAA ATGGGACTCC AGAGGGCCTG
GCCTCACCCT CCCTATTCTC AGTCCTGCAG CCTGAGCATG TGCTGGCCGG
CTGTACCCTG AGGTGCCCTC CCACTTCCTC CTTCAGGTTC TGAGGGGGAC
AGGCTGACAA GTAGGACCCG AGGCACTGGA GGAGCATTGA AGGAGAAGAT
CTGTAAGTAA GCCTTTGTCA GAGCCTCCAA GGTTCAGTTC AGTTCTCACC
TAAGGCCTCA CACACGCTCC TTCTCTCCCC AGGCCTGTGG GTCTTCATTG
CCCAGCTCCT GCCCGCACTC CTGCCTGCTG CCCTGACCAG AGTCATC
ATG CCT CTT GAG CAG AGG AGT CAG CAC TGC AAG CCT GAA GAA
GGC CTT GAG GCC CGA GGA GAG GCC CTG GGC CTG GTG GGT GCG
CAG GCT CCT GCT ACT GAG GAG CAG CAG ACC GCT TCT TCC TCT
TCT ACT CTA GTG GAA GTT ACC CTG GGG GAG GTG CCT GCT GCC
GAC TCA CCG AGT CCT CCC CAC AGT CCT CAG GGA GCC TCC AGC
TTC TCG ACT ACC ATC AAC TAC ACT CTT TGG AGA CAA TCC GAT
GAG GGC TCC AGC AAC CAA GAA GAG GAG GGG CCA AGA ATG TTT
CCC GAC CTG GAG TCC GAG TTC CAA GCA GCA ATC AGT AGG AAG
ATG GTT GAG TTG GTT CAT TTT CTG CTC CTC AAG TAT CGA GCC
AGG GAG CCG GTC ACA AAG GCA GAA ATG CTG GAG AGT GTC CTC
AGA AAT TGC CAG GAC TTC TTT CCC GTG ATC TTC AGC AAA GCC
TCC GAG TAC TTG CAG CTG GTC TTT GGC ATC GAG GTG GTG GAA
GTG GTC CCC ATC AGC CAC TTG TAC ATC CTT GTC ACC TGC CTG
GGC CTC TCC TAC GAT GGC CTG CTG GGC GAC AAT CAG GTC ATG
CCC AAG ACA GGC CTC CTG ATA ATC GTC CTG GCC ATA ATC GCA
ATA GAG GGC GAC TGT GCC CCT GAG GAG AAA ATC TGG GAG GAG
CTG AGT ATG TTG GAG GTG TTT GAG GGG AGG GAG GAC AGT GTC
TTC GCA CAT CCC AGG AAG CTG CTC ATG CAA GAT CTG GTG CAG
GAA AAC TAC CTG GAG TAC CGG CAG GTG CCC GGC AGT GAT CCT
GCA TGC TAC GAG TTC CTG TGG GGT CCA AGG GCC CTC ATT GAA
ACC AGC TAT GTG AAA GTC CTG CAC CAT ACA CTA AAG ATC GGT
GGA GAA CCT CAC ATT TCC TAC CCA CCC CTG CAT GAA CGG GCT
TTG AGA GAG GGA GAA GAG TGA
GTCTCAGCAC ATGTTGCAGC CAGGGCCAGT GGGAGGGGGT CTGGGCCAGT
GCACCTTCCA GGGCCCCATC CATTAGCTTC CACTGCCTCG TGTGATATGA
GGCCCATTCC TGCCTCTTTG AAGAGAGCAG TCAGCATTCT TAGCAGTGAG
TTTCTGTTCT GTTGGATGAC TTTGAGATTT ATCTTTCTTT CCTGTTGGAA
TTGTTCAAAT GTTCCTTTTA ACAAATGGTT GGATGAACTT CAGCATCCAA
GTTTATGAAT GACAGTAGTC ACACATAGTG CTGTTTATAT AGTTTAGGGG
TAAGAGTCCT GTTTTTTATT CAGATTGGGA AATCCATTCC ATTTTGTGAG
TTGTCACATA ATAACAGCAG TGGAATATGT ATTTGCCTAT ATTGTGAACG
AATTAGCAGT AAAATACATG ATACAAGGAA CTCAAAAGAT AGTTAATTCT
TGCCTTATAC CTCAGTCTAT TATGTAAAAT TAAAAATATG TGTATGTTTT
TGCTTCTTTG AGAATGCAAA AGAAATTAAA TCTGAATAAA TTCTTCCTGT
TCACTGGCTC ATTTCTTTAC CATTCACTCA GCATCTGCTC TGTGGAAGGC
CCTGGTAGTA GTGGG

Fig. 18B

GGATCCCCAT GGATCCAGGA AGAATCCAGT TCCACCCCTG CTGTGAACCC
AGGGAAGTCA CGGGGCCGGA TGTGACGCCA CTGACTTGCG CGTTGGAGGT
CAGAGAACAG CGAGATTCTC GCCCTGAGCA ACGGCCTGAC GTCGGCGGAG
GGAAGCAGGC GCAGGCTCCG TGAGGAGGCA AGGTAAGATG CCGAGGGAGG
ACTGAGGCGG GCCTCACCCC AGACAGAGGG CCCCCAATAA TCCAGCGCTG
CCTCTGCTGC CAGGCCTGGA CCACCCTGCA GGGGAAGACT TCTCAGGCTC
AGTCGCCACC ACCTCACCCC GCCACCCCCC GCCGCTTTAA CCGCAGGGAA
CTCTGGTGTA AGAGCTTTGT GTGACCAGGG CAGGGCTGGT TAGAAGTGCT
CAGGGCCCAG ACTCAGCCAG GAATCAAGGT CAGGACCCCA AGAGGGGACT
GAGGGTAACC CCCCCGCACC CCCACCACCA TTCCCATCCC CCAACACCAA
CCCCACCCCC ATCCCCCAAC ACCAAACCCA CCACCATCGC TCAAACATCA
ACGGCACCCC CAAACCCCGA TTCCCATCCC CACCCATCCT GGCAGAATCG
GAGCTTTGCC CCTGCAATCA ACCCACGGAA GCTCCGGGAA TGGCGGCCAA
GCACGCGGAT CC

Fig. 19

GCCGCGAGGG AAGCCGGCCC AGGCTCGGTG AGGAGGCAAG GTTCTGAGGG
GACAGGCTGA CCTGGAGGAC CAGAGGCCCC CGGAGGAGCA CTGAAGGAGA
AGATCTGCCA GTGGGTCTCC ATTGCCCAGC TCCTGCCCAC ACTCCCGCCT
GTTGCCCTGA CCAGAGTCAT C
ATG CCT CTT GAG CAG AGG AGT CAG CAC TGC AAG CCT GAA GAA
GGC CTT GAG GCC CGA GGA GAG GCC CTG GGC CTG GTG GGT GCG
CAG GCT CCT GCT ACT GAG GAG CAG GAG GCT GCC TCC TCC TCT
TCT ACT CTA GTT GAA GTC ACC CTG GGG GAG GTG CCT GCT GCC
GAG TCA CCA GAT CCT CCC CAG AGT CCT CAG GGA GCC TCC AGC
CTC CCC ACT ACC ATG AAC TAC CCT CTC TGG AGC CAA TCC TAT
GAG GAC TCC AGC AAC CAA GAA GAG GAG GGG CCA AGC ACC TTC
CCT GAC CTG GAG TCC GAG TTC CAA GCA GCA CTC AGT AGG AAG
GTG GCC GAG TTG GTT CAT TTT CTG CTC CTC AAG TAT CGA GCC
AGG GAG CCG GTC ACA AAG GCA GAA ATG CTG GGG AGT GTC GTC
GGA AAT TGG CAG TAT TTC TTT CCT GTG ATC TTC AGC AAA GCT
TCC AGT TCC TTG CAG CTG GTC TTT GGC ATC GAG CTG ATG GAA
GTG GAC CCC ATC GGC CAC TTG TAC ATC TTT GCC ACC TGC CTG
GGC CTC TCC TAC GAT GGC CTG CTG GGT GAC AAT CAG ATC ATG
CCC AAG GCA GGC CTC CTG ATA ATC GTC CTG GCC ATA ATC GCA
AGA GAG GGC GAC TGT GCC CCT GAG GAG AAA ATC TGG GAG GAG
CTG AGT GTG TTA GAG GTG TTT GAG GGG AGG GAA GAC AGT ATG
TTG GGG GAT CCC AAG AAG CTG CTC ACC CAA CAT TTC GTG CAG
GAA AAC TAC CTG GAG TAC CGG CAG GTC CCC GGC AGT GAT CCT
GCA TGT TAT GAA TTC CTG TGG GGT CCA AGG GCC CTC GTT GAA
ACC AGC TAT GTG AAA GTC CTG CAC CAT ATG GTA AAG ATC AGT
GGA GGA CCT CAC ATT TCC TAC CCA CCC CTG CAT GAG TGG GTT
TTG AGA GAG GGG GAA GAG TGA
GTCTGAGCAC GAGTTGCAGC CAGGGCCAGT GGGAGGGGGT CTGGGCCAGT
GCACCTTCCG GGGCCGCATC CCTTAGTTTC CACTGCCTCC TGTGACGTGA
GGCCCATTCT TCACTCTTTG AAGCGAGCAG TCAGCATTCT TAGTAGTGGG
TTTCTGTTCT GTTGGATGAC TTTGAGATTA TTCTTTGTTT CCTGTTGGAG
TTGTTCAAAT GTTCCTTTTA ACGGATGGTT GAATGAGCGT CAGCATCCAG
GTTTATGAAT GACAGTAGTC ACACATAGTG CTGTTTATAT AGTTTAGGAG
TAAGAGTCTT GttTTTTACT CAAATTgGGA AATCCATTCC ATTTTGTGAA
TTGTGACATA ATAATAGCAG TGGTAAAAGT ATTTGCTTAA AATTGTGAGC
GAATTAGCAA TAACATACAT GAGATAACTC AAGAAATCAA AAGATAGTTG
ATTCTTGCCT TGTACCTCAA TCTATTCTGT AAAATTAAAC AAATATGCAA
ACCAGGATTT CCTTGACTTC TTTG

Fig. 20

GGATCCTCCA CCCCAGTAGA GTGGGGACCT CACAGAGTCT GGCCAACCCT
CCTGACAGTT CTGGGAATCC GTGGCTGCGT TTGCTGTCTG CACATTGGGG
GCCCGTGGAT TCCTCTCCCA GGAATCAGGA GCTCCAGGAA CAAGGCAGTG
AGGACTTGGT CTGAGGCAGT GTCCTCAGGT CACAGAGTAG AGGGGgCTCA
GATAGTGCCA ACGGTGAAGG TTTGCCTTGG ATTCAAACCA AGGGCCCCAC
CTGCCCCAGA ACACATGGAC TCCAGAGCGC CTGGCCTCAC CCTCAATACT
TTCAGTCCTG CAGCCTCAGC ATGCGCTGGC CGGATGTACC CTGAGGTGCC
CTCTCACTTC CTCCTTCAGG TTCTGAGGGG ACAGGCTGAC CTGGAGGACC
AGAGGCCCCC GGAGGAGCAC TGAAGGAGAA GATCTGTAAG TAAGCCTTTG
TTAGAGCCTC CAAGGTTCCA TTCAGTACTC AGCTGAGGTC TCTCACATGC
TCCCTCTCTC CCCAGGCCAG TGGGTCTCCA TTGCCCAGCT CCTGCCCACA
CTCCCGCCTG TTGCCCTGAC CAGAGTCATC
ATG CCT CTT GAG CAG AGG AGT CAG CAC TGC AAG CCT GAA GAA
GGC CTT GAG GCC CGA GGA GAg GCC CTG GGC CTG GTG GGT GCG
CAG GCT CCT GCT ACT GAG GAG CAG GAG GCT GCC TCC TCC TCT
TCT AGT GTA GTT GAA GTC ACC CTG GGG GAG GTG CCT GCT GCC
GAG TCA CCA GAT CCT CCC CAG AGT CCT CAG GGA GCC TCC AGC
CTC CCC ACT ACC ATG AAC TAC CCT CTC TGG AGC CAA TCC TAT
GAG GAC TCC AGC AAC CAA GAA GAG GAG GGG CCA AGC ACC TTC
CCT GAC CTG GAG TCT GAG TTC CAA GCA GCA CTC AGT AGG AAG
GTG GCC AAG TTG GTT CAT TTT CTG CTC

Fig. 21

G GGG CCA AGC ACC TCG CCT GAC GCA GAG TCC TTG TTC CGA
GAA GCA CTC AGT AAC AAG GTG GAT GAG TTG GCT CAT TTT CTG
CTC CGC AAG TAT CGA GCC AAG GAG CTG GTC ACA AAG GCA GAA
ATG CTG GAG AGA GTC ATC AAA AAT TAC AAG CGC TGC TTT CCT
GTG ATC TTC GGC AAA GCC TCC GAG TCC CTG AAG ATG ATC TTT
GGC ATT GAC GTG AAG GAA GTG GAC CCC GCC AGC AAC ACC TAC
ACC CTT GTC ACC TGC CTG GGC CTT TCC TAT GAT GGC CTG CTG
GGT AAT AAT CAG ATC TTT CCC AAG ACA GGC CTT CTG ATA ATC
GTC CTG GGC ACA ATT GCA ATG GAG GGC GAC AGC GCC TCT GAG
GAG GAA ATC TGG GAG GAG CTG GGT GTG ATG GGG GTG TAT GAT
GGG AGG GAG CAC ACT GTC TAT GGG GAG CCC AGG AAA CTG CTC
ACC CAA GAT TGG GTG CAG GAA AAC TAC CTG GAG TAC CGG CAG
GTA CCC GGC AGT AAT CCT GCG CGC TAT GAG TTC CTG TGG GGT
CCA AGG GCT CTG GCT GAA ACC AGC TAT GTG AAA GTC CTG GAG
CAT GTG GTC AGG GTC AAT GCA AGA GTT CGC ATT GCC TAC CCA
TCC CTG CGT GAA GCA GCT TTG TTA GAG GAG GAA GAG GGA GTC
TGAGCATGAG TTGCAGCCAG GGCTGTGGGG AAGGGGCAGG GCTGGGCCAG
TGCATCTAAC AGCCCTGTGC AGCAGCTTCC CTTGCCTCGT GTAACATGAG
GCCCATTCTT CACTCTGTTT GAAGAAAATA GTCAGTGTTC TTAGTAGTGG
GTTTCTATTT TGTTGGATGA CTTGGAGATT TATCTCTGTT TCCTTTTACA
ATTGTTGAAA TGTTCCTTTT AATGGATGGT TGAATTAACT TCAGCATCCA
AGTTTATGAA TCGTAGTTAA CGTATATTGC TGTTAATATA GTTTAGGAGT
AAGAGTCTTG TTTTTTATTC AGATTGGGAA ATCCGTTCTA TTTTGTGAAT
TTGGGACATA ATAACAGCAG TGGAGTAAGT ATTTAGAAGT GTGAATTC

Fig. 22

GGATCCCCAG GAGGCCCTAG AGGAGCACCA AAGGAGAAGA TCTGTAAGTA
AGCCTTTGTT AGAGCCTCCA AGGTTCAGTT TTTAGCTGAG GCTTCTCACA
TGCTCCCTCT CTCTCCAGGC CAGTGGGTCT CCATTGCCCA GCTCCTGCCC
ACACTCCTGC CTGTTGCGGT GACCAGAGTC GTC
ATG TCT CTT GAG CAG AAG AGT CAG CAC TGC AAG CCT GAG GAA
GGC CTT GAC ACC CAA GAA GAG GCC CTG GGC TGG TGG GTG TGC
AGG CTG CCA CTA CTG AGG AGC AGG AGG CTG TGT CCT CCT CCT
CTC CTC TGG TCC AGG CAC CCT

Fig. 23

TAT TTC TTT CCT GTG ATC TTC AGC AAA GCT TCC GAT TCC TTG
CAG CTG GTC TTT GGC ATC GAG CTG ATG GAA GTG GAC CCC ATC
GGC CAC GTG TAC ATC TTT GCC ACC TGC CTG GGC CTC TCC TAC
GAT GGC CTG CTG GGT GAC AAT CAG ATC ATG CCC AGG ACA GGC
TTC CTG ATA ATC ATC CTG GCC ATA ATC GCA AGA GAG GGC GAC
TGT GCC CCT GAG GAG

Fig. 24

AGA AGC ACT AGT TTC CTT GTG ATC TAT GGC AAA GCC TCA GAG
TGC ATG CAG GTG ATG TTT GGC ATT GAC ATG AAG GAA GTG GAC
CCC GCG GCC ACT CCT ACG TCT TGT ACC TGC TTG GGC CTC TCC
TAC AAT GGT CTG CTG GGT GAT GAT CAG AGC ATG CCC GAG A

Fig. 25

NUCLEIC ACID MOLECULES ENCODING THE MAGE-1 TUMOR REJECTION ANTIGEN PRECURSOR

Matter enclosed in heavy brackets [ ] appears in the original patent but forms no part of this reissue specification; matter printed in italics indicates the additions made by reissue.

This application is a *reissue of Ser. No. 07/807,043, U.S. Pat. No. 5,342,774, which is a* continuation-in-part of Ser. No. [764,364]*764,365*, filed Sep. 23, 1991, abandoned, which is a continuation-in-part of Ser. No. 728,838, filed Jul. 9, 1991, abandoned, which is a continuation-in-part of Ser. No. 705,702, filed May 23, 1991, and all now abandoned.

FIELD OF THE INVENTION

This invention relates in general to the field of immunogenetics as applied to the study of oncology. More specifically, it relates to the study and analysis of mechanisms by which tumors are recognized by the organism's immune system such as through the presentation of so-called tumor rejection antigens, and the expression of what will be referred to herein as "tumor rejection antigen precursors".

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18:769-778 (1957); Klein et al., Cancer Res. 20:1561-1572 (1960); Gross, Cancer Res. 3: 326-333 (1943), Basombrio, Cancer Res. 30:2458-2462 (1970) for general teachings on inducing tumors with chemical carcinogens and differences in cell surface antigens. This class of antigens has come to be known as "tumor specific transplantation antigens" or "TSTAs". Following the observation of presentation such antigens when induced by chemical carcinogens, similar results were obtained when tumors were induced in vitro via ultraviolet radiation. See Kripke, J. Natl, Canc. Inst. 53: 333-1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241-259 (1976).

The family of tum$^-$ antigen presenting cell lines are immunogenic variants obtained by mutagenesis of mouse tumor cells or cell lines, as described by Boon et al., J. Exp. Med. 152: 1184-1193 (1980), the disclosure of which is incorporated by reference. To elaborate, tum$^-$ antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum$^-$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43:125 (1983).

It appears that tum$^-$ variants fail to form progressive tumors because they elicit an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl, Acad. Sci. USA 76:5282-5285 (1979); and the observation that intraperitoneally injected tum$^-$ cells of mastocytoma P815 multiply exponentially for 12-15 days, and then are eliminated in only a few days in the midst of an influx of lymphocytes and macrophages (Uyttenhove et al., J. Exp. Med. 152: 1175-1183 (1980)). Further evidence includes the observation that mice acquire an immune memory which permits them to resist subsequent challenge to the same tum$^-$ variant, even when immunosuppressive amounts of radiation are administered with the following challenge of cells (Boon et al., Proc. Natl, Acad. Sci. USA 74:272-275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157:1992-2001 (1983). Thus, it has been shown that it is possible to elicit presentation of a so-called "tumor rejection antigen" in a tumor which is a target for syngeneic rejection response. Similar results have been obtained when foreign genes have been transfected into spontaneous tumors. See Fearson et al., Cancer Res. 48: 2975-1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1-59 (1977); Boon et al., J. Exp. Med. 152: 1184-1193 (1980); Brunner et al., J. Immunol. 124: 1627-1634 (1980); Maryanski et al., Eur. J. Immunol. 124:1627-1634 (1980); Maryanski et al., Eur. J. Immunol. 12:406-412 (1982); Palladino et al., Canc. Res. 47: 5074-5079 (1987). This type of analysis is required for other types of antigens recognized by CTLs, including minor histocompatibility antigens, the male specific H-Y antigens, and a class of antigens, referred to as "tum$^-$" antigens, and discussed herein.

A tumor exemplary of the subject matter described supra is known as P815. See DePlaen et al., Proc. Natl. Acad. Sci. USA 85: 2274-2278 (1988); Szikora et al., EMBO J 9:1041-1050 (1990), and Sibille et al., J. Exp. Med. 172:35-45 (1990), the disclosures of which are incorporated by reference. The P815 tumor is a mastocytoma, induced in a DBA/2 mouse with methylcholanthrene and cultured as both an in vitro tumor and as a cell line. The P815 line has generated many tum$^-$ variants following mutagenesis, including variants referred to as P91A (DePlaen, supra), 35B (Szikora, supra), and P198 (Sibille, supra). In contrast to tumor rejection antigens—and this is a key distinction—the tum$^-$ antigens are only present after the tumor cells are mutagenized. Tumor rejection antigens are present on cells of a given tumor without mutagenesis. Hence, with reference to the literature, a cell line can be tum$^+$ such as the line referred to as "P1" and can be provoked to produce tum$^-$ variants. Since the tum$^-$ phenotype differs from that of the parent cell line, one expects a difference in the DNA of tum$^-$ cell lines as compared to their tum$^+$ parental lines, and this difference can be exploited to locate the gene of interest in tum$^-$ cells. As a result, it was found that genes of tum$^-$ variants such as P91A, 35B and P198 differ from their normal alleles by point mutations in the coding regions of the gene. See Szikora and Sibille, supra, and Lurquin et al., Cell 58:293-303 (1989). This has proved not to be the case with the TRAs of this invention. These papers also demonstrated that peptides derived from the tum$^-$ antigen are presented by the $L^d$ molecule for recognition by CTLs.

It has now been found that the genes which code for the molecules which are processed to form the presentation tumor rejection antigens (referred to as "tumor rejection antigen precursors", "precursor molecules" or "TRAPs" hereafter), are found in normal and tumorigenic cells, but are only expressed in tumor cells. Genes which code for the TRAPs have now been isolated and cloned, and represent a portion of the invention disclosed herein.

The gene is useful as a source for the isolated and purified tumor rejection antigen precursors and the TRA themselves, either of which can be used as an agent for treating the cancer for which the antigen is a "marker", as well as in various diagnostic and surveillance approaches to oncology, discussed infra. It is known, for example, that tum$^-$ cells can be used to generate CTLs which lyse cells presenting different tum$^-$ antigens as well as tum$^+$ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transformed by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8:385-389 (1987)). This response has been particularly well studied for melanomas, and MLTC have been carried out either with peripheral blood cells or with tumor infiltrating lymphocytes. Examples of the literature in this area including Knuth et al., Proc. Natl. Acad. Sci. USA 86:2804-2802 (1984); Mukherji et al., J. Exp. Med. 158: 240 (1983); Hérin et all, Int. J. Canc. 39: 390-396 (1987); Topalian et al, J. Clin. Oncol 6:839-853 (1988). Stable cytotoxic T cell clones ("CTLs" hereafter) have been derived from MLTC responder cells, and these clones are specific for the tumor cells. See Mukherji et al., supra, Hérin et al., supra, Knuth et al., supra. The antigens recognized on tumor cells by these autologous CTLs do not appear to represent a cultural artifact, since they are found on fresh tumor cells. Topalian et al., supra; Degiovanni et al., Eur. J. Immunol. 20: 1865-1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, which ramifications that are described infra. These isolated nucleic acid sequences for human tumor rejection antigen precursors and applications thereof, as described infra, are also the subject of this invention.

These and various other aspects of the invention are elaborated upon in the disclosure which follows.

BRIEF DESCRIPTION OF THE FIGURES

FIGS. 6a, 6b, 6c and 6d present the nucleotide and amino acid sequence for the three exons and 5' region of gene P1A. This information is also presented in sequence id no: 1, sequence id no: 2, and sequence id no: 3. The full cDNA for the sequence is available from EMBL/GenBank (accession number M36387). The complete sequence between 0.7 and 5 of FIG. 5 is also deposited with EMBL/GenBank (accession number M36386).

FIGS. 9A and 9B present the entire sequence of P1A gene, with exons presented in capital letters. (*SEQ ID NOS: 1, 2, and 3*).

FIG. 12 shows homology of sections of exon 3 from genes mage 1, 2 and 3.

FIGS. 14A and 14B present the data of FIG. 13 in table form.

FIG. 17 presents a genomic nucleic acid sequence for mage-1 (*SEQ ID NO: 8*).

FIG. 18 sets forth a genomic nucleic acid sequence for mage-2 (*SEQ ID NO: 9*).

FIG. 19 is a partial sequence for a variant of mage-2, referred to as mage-21 (*SEQ ID NO: 10*).

FIG. 20 presents partial sequence for cDNA of mage-3 (*SEQ ID NO: 11*).

FIG. 21 shows a partial sequence for variant mage-31 (*SEQ ID NO: 12*).

FIG. 22 is a partial sequence for cDNA for mage-4 (*SEQ ID NO: 13*).

FIG. 23 is a partial sequence of genomic DNA for mage-5 (*SEQ ID NO: 14*).

FIG. 24 is a partial sequence of genomic DNA for mage-6 (*SEQ ID NO: 15*).

FIG. 25 is a partial sequence of genomic DNA for mage-7 (*SEQ ID NO: 16*).

DETAILED DESCRIPTION OF PREFERRED EMBODIMENTS

EXAMPLE 1

Figure 1:
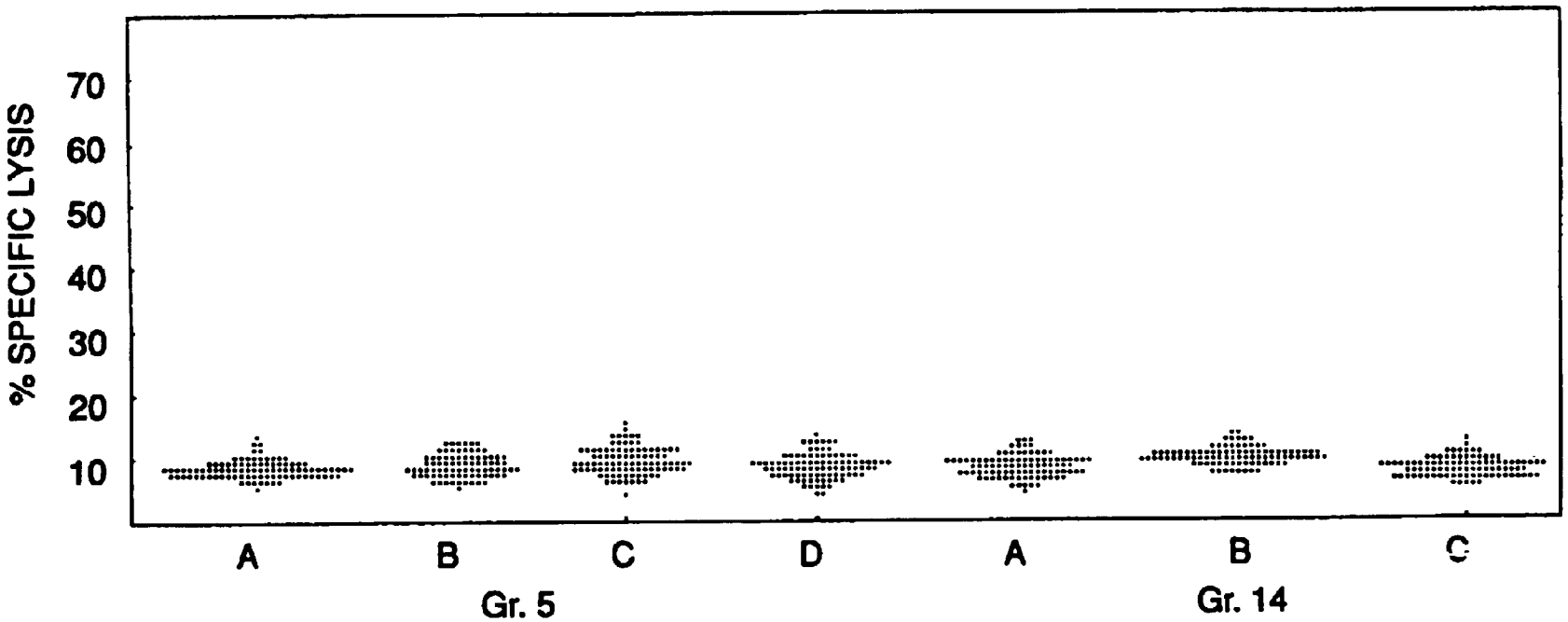
FIG. 1 depicts detection of transfectants expressing antigen P815A.

In order to identify and isolate the gene coding for antigen PS15A, gene transfection was used. This approach requires both a source of the gene, and a recipient cell line. Highly transfectable cell line P1.HTR was the starting material for the recipient, but it could not be used without further treatment, as it presents "antigen A", one of four recognized P815 tumor antigens. See Van Pel et al., Molecular Genetics 11: 467-475 (1985). Thus, screening experiments were carried out to isolate cell lines which did not express the antigen and which nonetheless possessed P1.HTR's desirable qualities.

To do this, P1.HTR was screened with CTLs which were specific for each of tumor antigens A, B, C and D. Such CTLs are described by Uyttenhove et al., J. Exp. Med. 157:1040-1052 (1983).

To carry out the screening, the CTLs were incubated with 2000 $^{51}$Cr labelled cells at various ratios of effector/target cells, in 96 well conical microplates in final volume of 200 μl. After 4 hours of incubation at 37° C. chromium release was measured Additional information on the CTL assay and screening protocol, in general may be found in Boon et al., J. Exp. Med. 152: 1184-1193 (1980), and Maryanski et al., Eur. J. Immunol. 12: 406-412 (1982), the disclosure of which are incorporated by reference.

When these screenings were carried out, a cell line variant was found which expressed neither antigen A or B. Additional screenings then yielded a variant which also lacked antigen C. Please see FIG. 2 for a summary of the results of these screenings. The variant PO.HTR is negative for antigens A, B and C, and was therefore chosen for the transfection experiments.

The cell line PO.HTR has been deposited in accordance with the Budapest Treaty at the Institute Pasteur Collection Nationale De Cultures De Microorganismes, 28, Rue de Docteur Roux, 75724 Paris France, and has accession number 1-1117.

This methodology is adaptable to secure other cell lines which are variants of a cell type which normally presents at least one of the four recognized P815 tumor antigens, i.e., antigens A, B, C and D, where the variants present none of antigens A, B and C. P1.HTR is a mastocytoma cell line, so it will be seen that the protocol enables the isolation of biologically pure mastocytoma cell lines which express none of P815 antigens A, B and C, but which are highly transfectable. Other tumor types may also be screened in this fashion to secure desired, biologically pure cell lines. The resulting cell lines should be at least as transfectable with foreign DNA as is P1.HTR, and should not express a specific antigen.

EXAMPLE 2

Previous work reported by DePlaen et al., Proc. Natl. Acad. Sci. USA 85: 2274-2278 (1988) the disclosure of which is incorporated by reference herein had shown the efficacy of using cosmid library transfection to recover genes coding for tum$^-$ antigens.

The entire plasmid and genomic DNA of P1.HTR was prepared, following Wölfel et al., Immunogenetics 26: 178-187 (1987). The transfection procedure followed Corsaro et al., Somatic Cell Molec. Genet 7:603-616 (1981), with some modification. Briefly, 60 μg of cellular DNA and 3 μg of DNA of plasmid pHMR272, described by Bernard et al., Exp. Cell. Biol. 158:237-243 (1985) were mixed. This plasmid confers hygromycin resistance upon recipient cells, and therefore provides a convenient way to screen for transfectants. The mixed DNA was combined with 940 ul of 1 mM Tris-HCl (pH 7.5), 0.1mMEDTA; and 310 ul 1M $CaCl_2$. The solution was added slowly, and under constant agitation to 1.25 ml of 50 mM Hepes, 280 mMNaCl, 1.5 $mMNa_2HPO_4$, adjusted to pH 7.1 with NaOH. Calcium phosphate—DNA precipitates were allowed to form for 30-45 minutes at room temperature. Following this, fifteen groups of PO.HTR cells ($5\times10^6$) per group were centrifuged for 10 minutes at 400 g. Supernatants were removed, and pellets were resuspened directly into the medium containing the DNA precipitates. This mixture was incubated for 20 minutes at 37° C., after which it was added to an 80 $cm^2$ tissue culture flask containing 22.5 ml DMEM, supplemented with 10% fetal calf serum. After 24 hours, medium was replaced. Forty-eight hours after transfection, cells were collected and counted. Transfected cells were selected in mass culture using culture medium supplemented with hygromycin B (350 ug/ml). This treatment selected cells for hygromycin resistance.

For each group, two flasks were prepared, each containing $8\times10^6$ cells in 40 ml of medium. In order to estimate the number of transfectants, $1\times10^6$ cells from each group were plated in 5 ml DMEM with 10% fetal calf serum (FCS), 0.4% bactoagar, and 300 ug/ml hygromycin B. The colonies were then counted 12 days later. Two independent determinations were carried out and the average taken. This was multiplied by 5 to estimate the number of transfectants in the corresponding group. Correction had to be made for the cloning efficiency of P815 cells, known to be about 0.3.

EXAMPLE 3

Eight days after transfection as described in example 2, supra, antibiotic resistant transfectants were separated from dead cells, using density configuration with Ficoll-Paque. These cells were maintained in non-selective medium for 1 or 2 days. The cells were plated in 96 well microplates (round bottom), at 30 cells/microwell in 200 ul of culture medium. Anywhere from 100-400 microwells were prepared, depending on the number of transfectants prepared. Agar colony tests gave estimates of 500-3000. After 5 days, the wells contained about $6\times10^4$ cells and replicate plates were prepared by transferring 1/10 of the wells to microplates which were then incubated at 30° C. One day later, master plates were centrifuged, medium removed, and 750 CTLs against P815 antigen A (CTL-Pi:5) were added to each well together with $10^6$ irradiated syngeneic feeder spleen cells in CTL culture medium containing 40 U/ml recombinant human IL-2, and HAT medium to kill stimulator cells. Six days later, plates were examined visually to identify wells where CTLs had proliferated. Where plates showed proliferating microcultures, aliquots of 100 ul of the wells were transferred to another plate containing $^{51}Cr$ labeled P1.HTR target cells ($2\times10^3$–$4\times10^3$ per well), and chromium release was measured after 4 hours. Replicate microcultures corresponding to those showing high CTL activity were expanded and cloned by limited dilution in DMEM with 10% FCS. Five days later, about 200 clones were collected and screened with the CTL.Pi:5 cell line, described Supra, in a visual lysis assay. See FIG. 1A for these results.

In these experiments, three of the fifteen groups of transfectants yielded a few positive microcultures. These microcultures were tested for lytic activity against P1.HTR, as described supra. Most of the microcultures where proliferation was observed showed lytic activity. This activity was well above background, as shown in FIG. 1B. This figure summarizes data wherein two groups of cells (groups "5" or "14"), 400 and 300 microwells were seeded with 30 hygromycin resistant transfected cells. Amplification and duplication of the microcultures was followed by addition of anti-A CTL Pl:5. Six days later, lytic activity against P1.HTR was tested. In the figure, each point represents lytic activity of a single microculture.

Duplicate microcultures corresponding to several positive wells were subcloned, and more than 1% of the subclones were found to be lysed by anti-A CTL. Thus, three independent transfectants expressing P815A were obtained from 33,000 hygromycin resistant transfectants. One of these lines, referred to hereafter as P1A.T2 was tested further.

Figure 2:
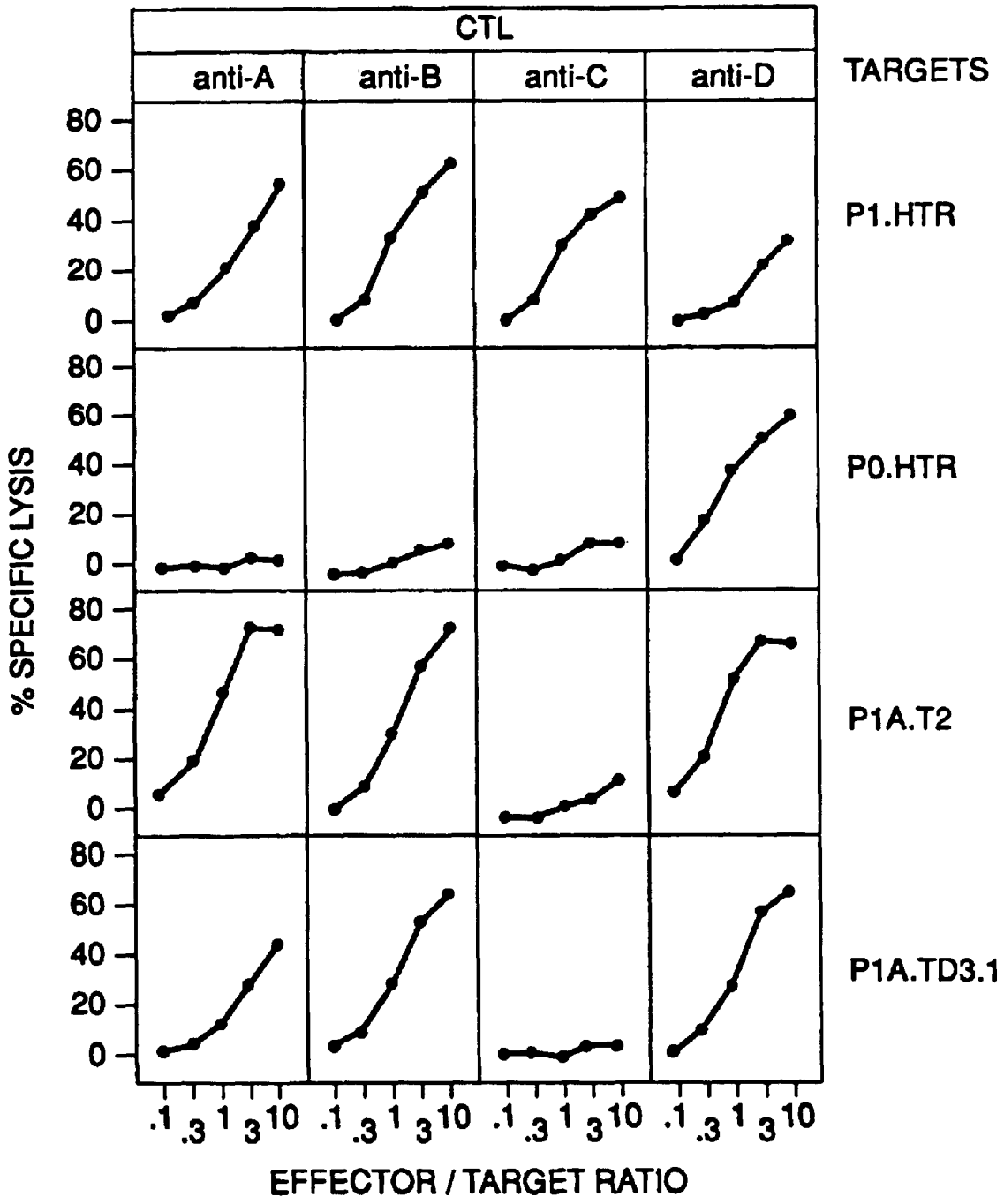
FIG. 2 shows the sensitivity of clones P1.HTR, PO.HTR, genomic transfectant P1A.T2 and cosmid transfectant P1A.TC3.1 to lysis by various CTLs, as determined by chromium release assays.

The relevant antigen profile of P1A.T2 is shown in FIG. 2, this being obtained via anti-CTL assays of the type described supra.

EXAMPLE 4

The CTL assays carried out for P1A.T2 demonstrated that it presented antigen A ("P815A"), and therefore had received the gene from P1.HTR. To that end, this cell line was used as a source for the gene for the antigen precursor in the following experiments.

Prior work had shown that genes coding for tum⁻ antigens could be recovered directly from transfectants obtained with a cosmid library. See DePlaen et al., Proc. Natl. Acad. Sci. USA 85: 2274-2278 (1988). This procedure was followed for recovery of the P815 gene.

Total genomic DNA of P1A.T2 was partially digested with restriction endonuclease Sau 3A1, and fractionated by NaCl density gradient ultracentriguation to enrich for 35-50 kb DNA fragments, following Grosveld et al., Gene 10: 6715-6732 (1982). These fragments were ligated to cosmid arms of C2RB, described by Bates et al., Gene 26: 137-146 (1983), the disclosure of which is incorporated by reference. These cosmid arms had been obtained by cleavage with SmaI and treatment with calf intestinal phosphatase, followed by digestion with BamHI. Ligated DNA was packaged into lambda phage components, and titrated on E. coli ED 8767, following Grosveld et al., supra. Approximately $9\times10^5$ ampicillin resistant colonies were obtained per microgram of DNA insert.

The cosmid groups were amplified by mixing 30,000 independent cosmids with 2 ml of ED 8767 in 10 mM$MgCl_2$, incubated 20 minutes at 37° C., diluted with 20 ml of Luria Bertani ("LB") medium, followed by incubation for one hour. This suspension was titrated and used to inoculate 1 liter of LB medium in the presence of ampicillin (50 ug/ml). At a bacterial concentration of $2\times10^8$ cells/ml ($OD_{600}$=0.8), a 10 ml aliquot was frozen, and 200 ug/ml chloramphenicol was added to the culture for overnight incubation. Total cosmid DNA was isolated by alkaline lysis procedure, and purified on CsCl gradient.

In these experiments, a library of 650,000 cosmids was prepared. The amplification protocol involved the use of 21 groups of approximately 30,000 cosmids.

EXAMPLE 5

Using the twenty-one groups of cosmids alluded to supra, (60 ug) and 4 ug of pHMR272, described supra, groups of $5\times10^6$ PO.HTR cells were used as transfectant hosts. Transfection was carried out in the same manner as described in the preceding experiments. An average of 3000 transfectants per group were tested for antigen presentation, again using CTL assays as described. One group of cosmids repeatedly yielded positive transfectants, at a frequency of about 1/5,000 drug resistant transfectants. The transfectants, as with P1A.T2, also showed expression of both antigen A and B. The pattern of expression of transfectant p1A.TC3.1 is shown in FIG. 2.

EXAMPLE 6

As indicated in Example 5, supra, three independent cosmid transfected cells presented P815A antigen. The DNA of these transfectants was isolated and packaged directly with lambda phage extracts, following DePlaen et al., Proc. Natl. Acad. Sci. USA 85: 2274-2278 (1988). The resulting product was titrated on E. coli ED 8767 with ampicillin selection, as in Example 5. Similarly, transfection and amplification of the cosmids followed example 5, again using PO.HTR.

High frequencies of transfection were observed, as described in Table 1, which follows:

TABLE 1

Transfer of the expression of antigen P815A by cosmids by direct packaging

| Transfectant obtained with the cosmid library | No. of cosmids obtained by direct packaging of 0.5 μg of DNA | No. of transfectants expressing P815A/no. of $HmB^r$ transfectants |
|---|---|---|
| TC3.1 | 32 | 87/192 |
| TC3.2 | 32000 | 49/384 |
| TC3.3 | 44 | 25/72 |

The cosmids were analyzed with restriction enzymes and it was found that directly packaged transfectant P1A.TC3.1 contained 32 cosmids, 7 of which were different. Each of these 7 cosmids was transfected into PO.HTR, in the manner described supra, and again, following the protocols described above, transfectants were studied for presentation of P815A. Four of the cosmid transfectants showed P815A presentation and, as with all experiments described herein, P815B was co-expressed.

Of the four cosmids showing presentation of the two antigens, cosmid C1A.3.1 was only 16.7 kilobases long, and was selected for further analysis as described infra.

Figure 3:
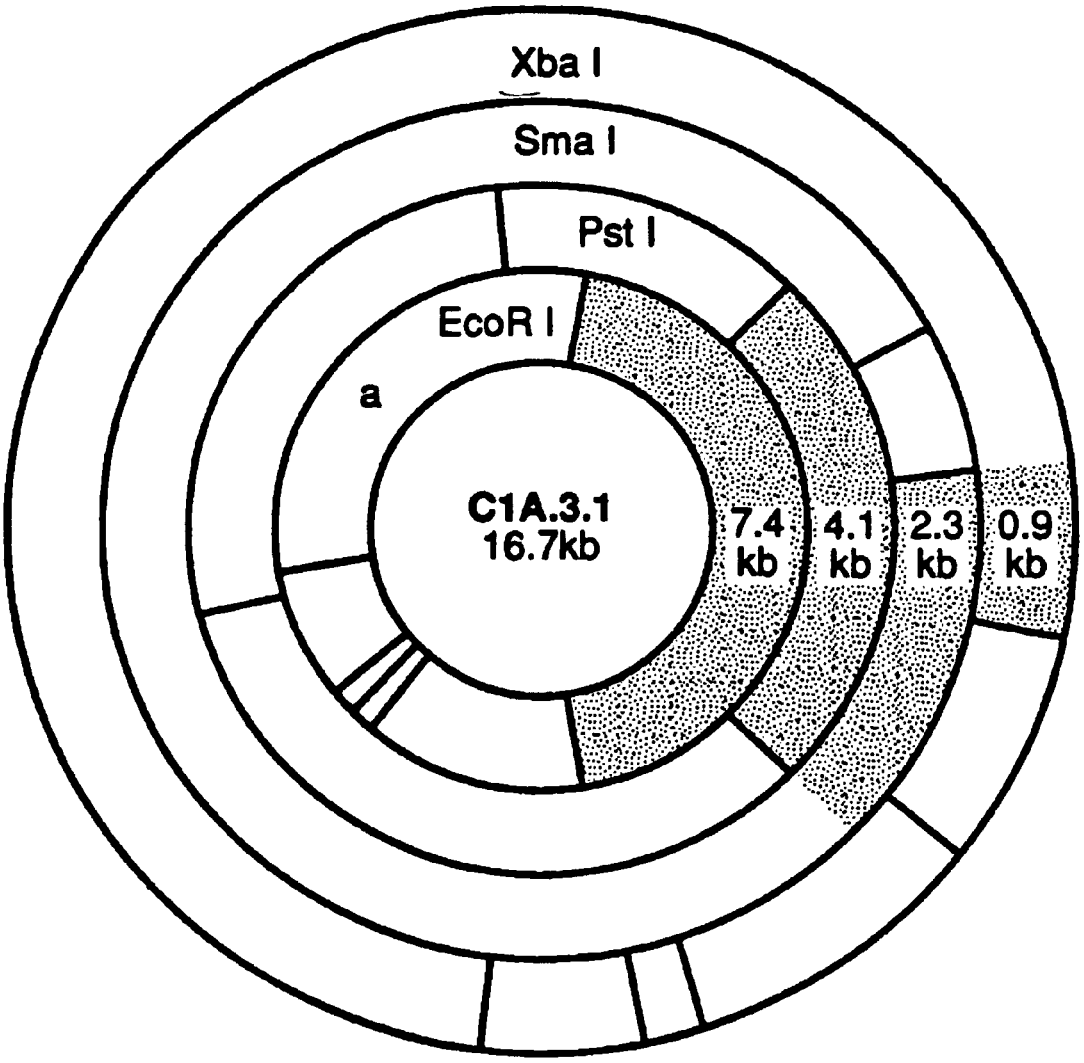
FIG. 3 is a restriction map of cosmid C1A.3.1.

The cosmid C1A.3.1 was subjected to restriction endonuclease analysis, yielding the map shown in FIG. 3.

All EcoRI fragments were transfected, again using the above described protocols, and only the 7.4 kilobase fragment produced a transfectant that anti-A CTLs could lyse. Similar experiments were carried out on the PstI fragments, and only a 4.1 kb fragment fully contained within the 7.4 kb EcoRI fragment produced lysable transfectants.

This fragment (i.e., the 4.1 kb PstI fragment), was digested with SmaI, giving a 2.3 kb fragment which also yielded host cells presenting antigens A and B after transfection. Finally, a fragment 900 bases long, secured with SmaI/XbaI, also transferred expression of the precursors of these two antigens, i.e., the transfected host cell presented both antigen A and antigen B.

EXAMPLE 7

The 900 base fragment described above was used as a probe to detect the expression of the P815A gene in parent cell line P1.HTR. To accomplish this, total cellular RNA was first isolated using the guanidine-isothiocyanate procedure of Davis et al., Basic Methods In Molecular Biology (Elseview Science Publishing Co, New York) (1986). The same reference was the source of the method used to isolate and purify polyA$^+$ mRNA using oligodT on cellulose column chromatography.

Samples were then subjected to Northern Blot analysis. RNA samples were fractionated on 1% agarose gels containing 0.66M formaldehyde. The gels were treated with 10×SSC (SSC: 0.15 M NaCl; 0.015 M sodium citrate, pH 7.0) for 30 minutes before overnight blotting on nitrocellulose membranes. These were baked for two hours at 80° C., after which the membranes were prehybridized for 15 minutes at 60° C. in a solution containing 10% dextran sulfate, 1% SDS and 1M NaCl. Hybridization was then carried out using denatured probe (the 900 base fragment), together with 100 ug/ml salmon sperm DNA.

Figure 4:
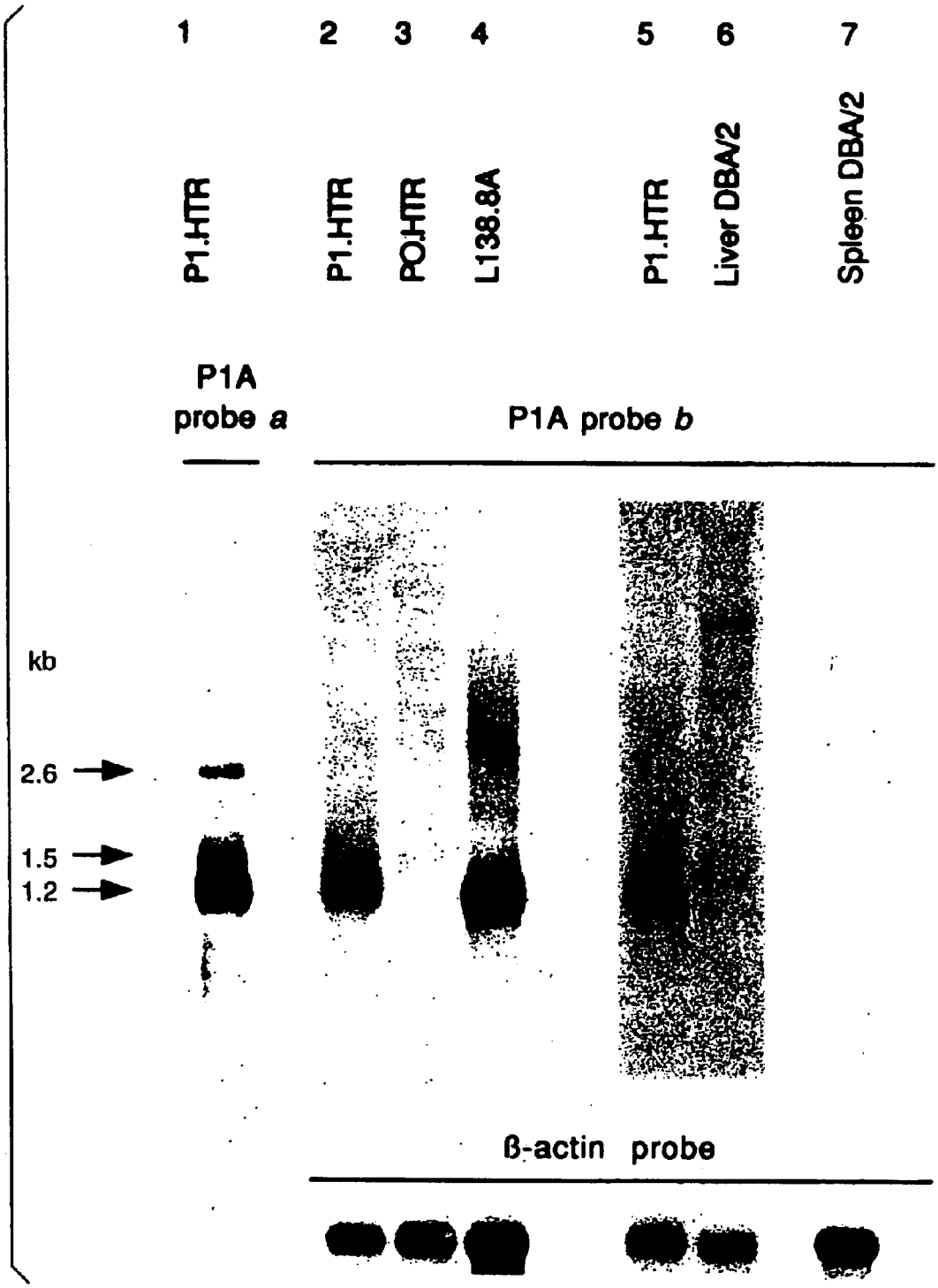
FIG. 4 shows Northern Blot analysis of expression of gene P1A.

When this protocol was carried out using P1.HTR poly A$^+$ RNA, a band of 1.2 kb and two fainter bands were identified, as shown in FIG. 4, lane 1 (6 ug of the RNA).

The same probe was used to screen cDNA of P1A, prepared from poly-A$^+$ RNA from the cell line. This yielded a 1 kb insert, suggesting a missing 5' end. The Northern blots for the cDNA are not shown.

Hybridization experiments in each case were carried out overnight at 60° C. The blots were washed twice at room temperature with 2×SSC and twice at 60° C. with 2×SSC supplemented with 1% SDS.

The foregoing experiments delineated the DNA expressing the P815A antigen precursor sufficiently to allow sequencing, using the well known Sanger dideoxy chain termination method. In order to do this, clones were generated using a variety of restriction endonucleases and synthetic oligonucleotide primers. The results for exons of the gene are set forth in FIG. 6 and sequence id no: 1, with corresponding amino acids presented below the nucleic acid sequence.

EXAMPLE 8

Given the sequencing information described supra, it was possible to further study the cDNA hybridization fragment (1 kb) to determine if the hypothesis that a 5' fragment had been lost was correct. To do this, a primer corresponding to positions 320-303 was used. Amplification was carried out using a 3' primer corresponding to positions 286-266 and 5' primers described by Frohman et al. Proc Natl. Acad. Sci. USA 85:8998-9002 (1988). A band of expected size (270 bases), was found, which hybridized to the probe described supra when Southern blotting was carried out, proving the assertion was correct. Following cloning into M13 tg 130 and tg 131, the small, 270 base pair band was sequenced.

The Northern analysis described supra suggested that the 5' end of the cDNA was missing. To obtain this sequence, cDNA was prepared from P1.HTRRNA using a primer corresponding to positions 320-303. The sequence was then amplified using the polymerase chain reaction using a 3' primer corresponding to positions 286-266 5' primer described by Frohman et al., Proc. Natl. Acad. Sci. USA 85:8998-9002 (1988). A band of the expected size (270 bases) was found, which hybridized to the 900 bp SmaI/XbaJ fragment described supra on a Southern blot. Following cloning into m13tg 130 A tg 131, the small, 270 bp fragment was sequenced.

EXAMPLE 9

Following the procurement of the sequences described in Examples 7 and 8 and depicted in FIG. 6, a 5.7 kb region of cosmid CLA.3.1 was sequenced. This fragment was know to contain the 900 base fragment which expressed P815A in transfectants. This experiment permitted delineation of introns and exons, since the cosmid is genomic in origin.

Figure 5:
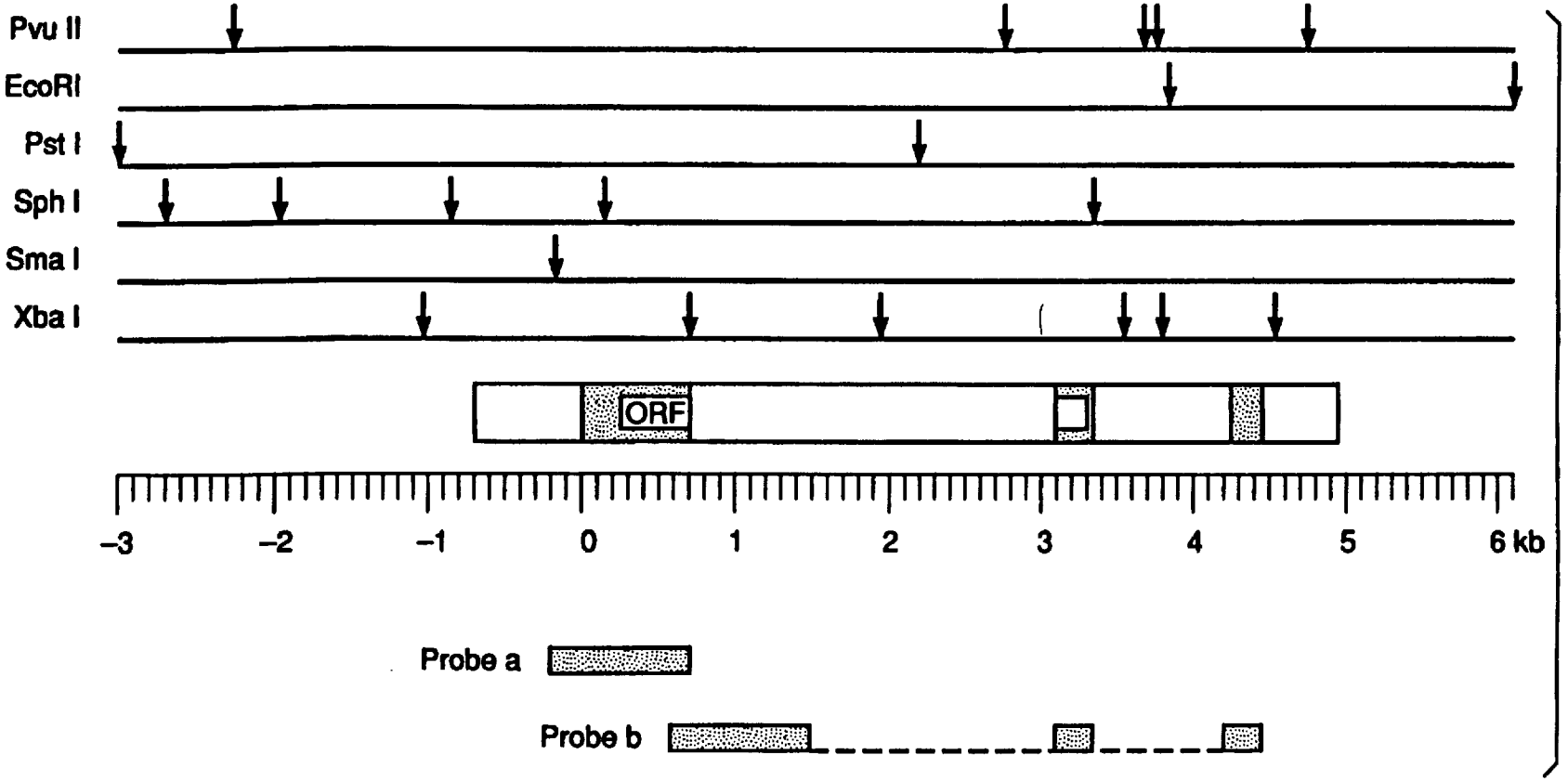
FIG. 5 sets forth the structure of gene P1A with its restriction sites.

The delineated structure of the gene is shown in FIG. 5. Together with FIG. 6, these data show that the gene for the antigen precursor, referred to as "PIA" hereafter, is approximately 5 kilobases long and contains 3 exons. An ORF for a protein of 224 amino acids starts in exon 1, ending in exon 2. The 900 base pair fragment which transfers expression of precursors for antigens A and B only contains exon 1. The promoter region contains a CAAT box, as indicated in FIG. 6a, and an enhancer sequence. This latter feature has been observed in promoters of most MHC class I genes, as observed by Geraghty et al., J. Exp. Med 171: 1-18 (1990); Kimura et al., Cell 44:261-272 (1986).

A computer homology search was carried out, using program FASTA with K-tuple parameters of 3 and 6, as suggested by Lipman et al., Science 227:1435-1441 (1985), and using Genbank database release 65 (October 1990). No homolgoy was found except for a stretch of 95 bases corresponding to part of an acid region coded by exon 1 (positions 524-618), which is similar to sequences coding of acidic regions in mouse nucleolar protein NO38/B23, as described by Bourbon et al., Mol. Biol. 200:627-638 (1988), and Schmidt-Zachmann et al., Chromosoma 96:417-426 (1988). Fifty six of 95 bases were identical. In order to to set whether these homologies were the reason for cross hybridizing, experiments were carried out using a mouse spleen cDNA library screened with the 900 base fragment. eDNA clones corresponding closely to the sizes of the cross hybridizing bands were obtained. These were partially sequenced, and the 2.6 kb cDNA was found to correspond exactly to reported cDNA sequence of mouse nucleolin, while the 1.5 kb cDNA corresponded to mouse nucleolar protein NO38/B23.

Analysis of the nucleotide sequence of the gene, referred to as "P1A" hereafter, suggests that its coded product has a molecular mass of 25 kd. Analysis of the sequence of FIG. 6 and sequence id no: 1 shows a potential nuclear targeting signal at residues 5-9 (Dingwall et al., Ann. Rev. Cell Biol. 2:367-390 (1986)), as well as a large acidic domain at positions 83-118. As indicated Supra, this contains the region of hornology between P1A and the two nucleolar proteins. A putative phosphorylation site can be found at position 125 (serine). Also, a second acidic domain is found close to the C-terminus, and uninterrupted stretch of 14 glutamate residues. A similar C-terminal structure has been found by Kessel et al. Proc. Natl. Acad. Sci. USA 84:5306-5310 (1987), in a murine heterodomain protein having nuclear localization.

In studies comparing the sequence of gene P1A to the sequences for P91A, 35B and P198, no similarities were found, showing that P1A is indicative of a different class of genes and antigens.

EXAMPLE 10

With the P1A probe and sequence in hand, investigations were carried out to determine whether the gene present in normal tissue was identical to that expressed by the tumor. To do this, phage libraries were prepared, using lambda gt 10 and genomic DNA of DBA12 murine kidney cells. P1A was used as a probe. Hybridization conditions were as described Supra, and a hybridizing clone was found. The clone contained exons one and two of the P1A gene, and corresponded to positions −0.7 to 3.8 of FIG. 5. Following localization of this sequence, PCR amplification was carried out to obtain the sequence corresponding to 3.8 to 4.5 of FIG. 5.

Sequence analysis was carried out, and no differences were found between the gene from normal kidneys and the P1A gene as obtained from the P815 tumor cells.

Figure 7:
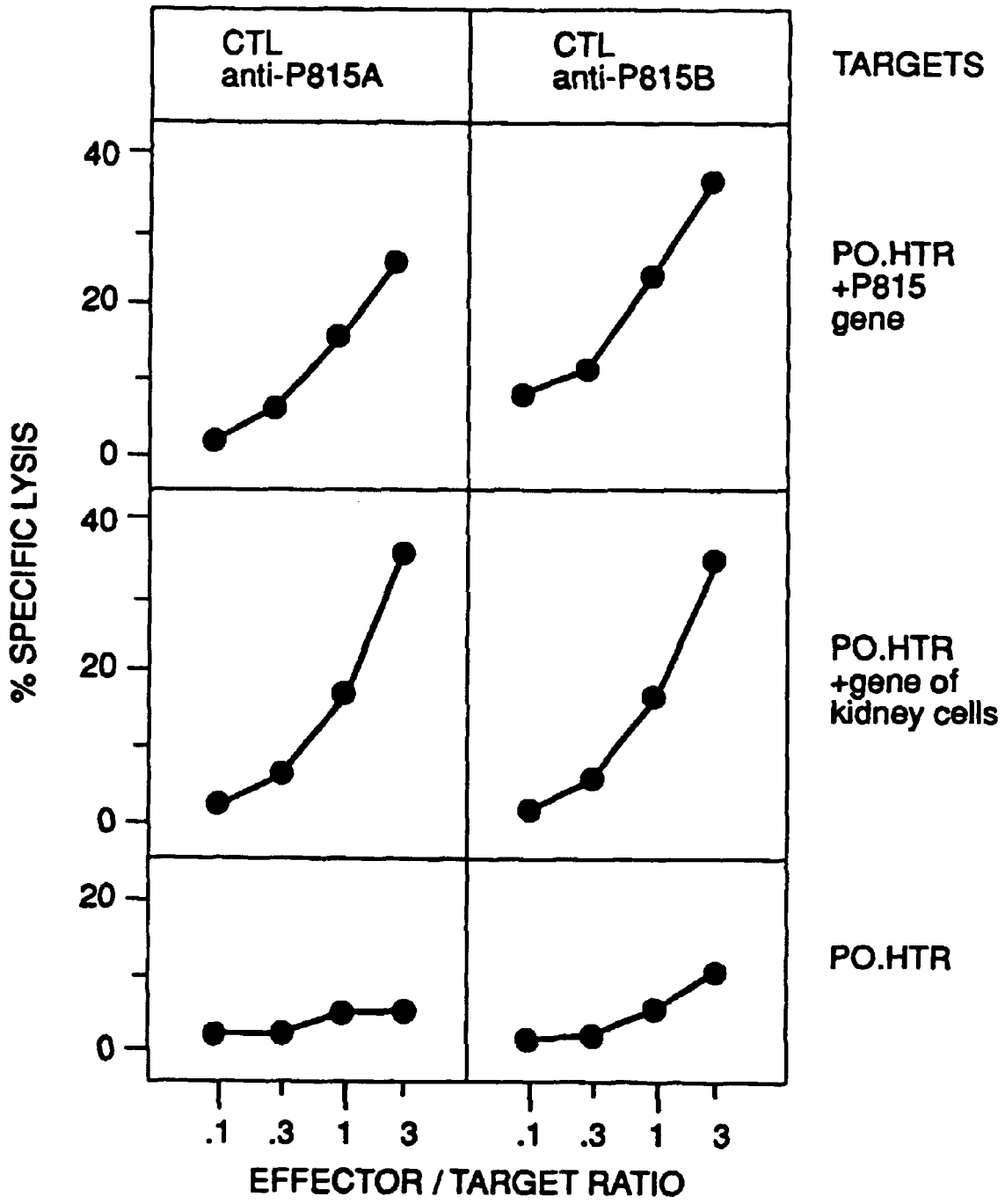
FIG. 7 shows the results obtained when cells were transfected with the gene from P1A, either isolated from P815 or normal cells and then tested with CTL lysis.

In further experiments, the gene as found in DBA/2 kidney cells was transfected into PO.HTR, as described supra. These experiments, presented pictorially in FIG. 7, showed that antigens A and B were expressed as efficiently by the kidney gene isolated as with the P815 gene isolated from normal kidney cells from the P815 tumor cells.

These experiments lead to the conclusion that the gene coding for the tumor rejection antigen precursor is a gene that does not result from a mutation; rather, it would appear that the gene is the same as one present in normal cells, but is not expressed therein. The ramification of this finding are important, and are discussed infra.

In studies not elaborated upon herein, it was found that variants of the gene were available. Some cells were "$P1A^{-}B^{+}$", rather than the normal "P1A". The only difference between these is a point mutation in exon 1, with the 18th triplet coding for Ala in the variant instead of Val.

EXAMPLE 11

Additional experiments were carried out with other cell types. Following the protocols described for Northern blot hybridizations supra, RNA of normal liver and spleen cells was tested to determine if a transcript of the P1A gene could be found. The Northern blot data are presented in FIG. 4 and, as can be seen, there is no evidence of expression.

The murine P815 cell line from which P1A was isolated is a mastocytoma. Therefore, mast cell lines were studied to determine if they expressed the gene. Mast cell line MC/9, described by Nabel et al., Cell 23: 19-28 (1981), and short term cultures of bone marrow derived mast cells were tested in the manner described supra (Northern blotting), but no transcript was found. In contact when a Balb/C derived IL-3 dependent cell line L138.SA (Hültner et al., J. Immunol. 142:3440-3446 (1989)) was tested, a strong signal was found. The mast cell work is shown in FIG. 4.

Figure 8:
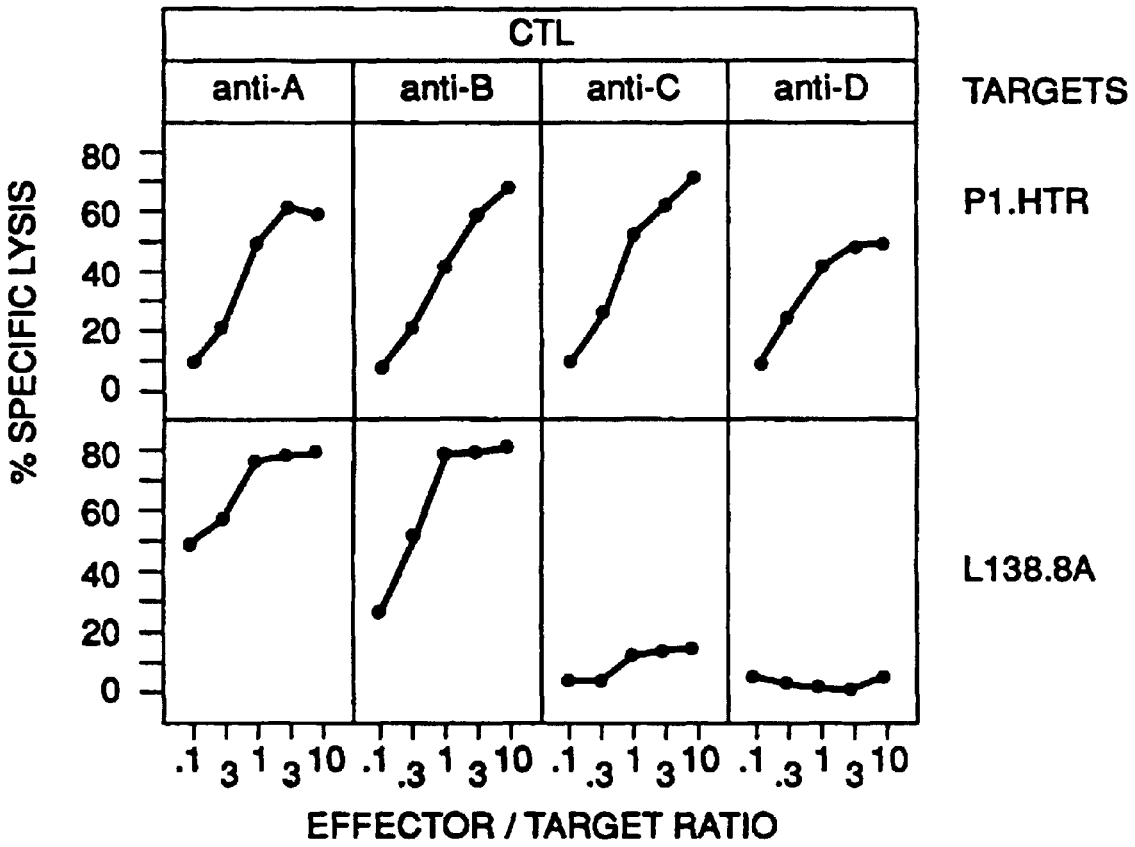
FIG. 8 shows lytic studies using mast cell line L138.8A.

It is known that both BALB/C and DBA/2 mice share $H\text{-}2^{d}$ haplotype, and thus it was possible to test sensitivity to lysis using the CLTs described supra. FIG. 8 shows these results, which essentially prove that anti-A and anti-B CTLs lysed the cells strongly, whereas anti-C and anti-D lines did not.

Further tests were carried out on other murine tumor cell lines, i.e., teratocarcinoma cell line PCC4 (Boon et al., Proc. Natl. Acad. Sci. USA 74: 272-275 (1977), and leukemias LEC and WEH1-3B. Expression could not be detected in any of these samples.

EXAMPLE 12

The actual presentation of the P1A antigen by MHC molecules was of interest. To test this, cosmid C1A.3.1 was transfected into fibroblast cell line DAP, which shows phenotype $H\text{-}2^{k}$. The cell lines were transfected with genes expressing one of the $K^{d}$, $D^{d}$, and $L^{d}$ antigen. Following transfection with both the cosmid and the MHC gene, lysis with CTLs was studied, again as described supra. These studies, summarized in Table 2, show that $L^{d}$ is required for presentation of the P1A antigens A and B.

TABLE 2

H-2-restriction of antigens P815A and P815B

| | No. of clones lysed by the CTL/no. of $HmB^{r}$ clones | |
|---|---|---|
| Recipient cell* | CTL anti-A | CTL anti-B |
| DAP + ($H\text{-}2^{k}$) | 0/208 | 0/194 |
| DAP + $K^{d}$ | 0/165 | 0/162 |
| DAP + $D^{d}$ | 0/157 | 0/129 |
| DAP + $L^{d}$ | 25/33 | 15/20 |

*Cosmid C1A.3.1 containing the entire P1A gene was transfected in DAP cells previously transfected with $H\text{-}2^{d}$ class 1 genes as indicated. Independent drug-resistant colonies were tested for lysis by anti-A or anti-B CTL in a visual assay.

The observation that one may associate presentation of a tumor rejection antigen with a particular MHC molecule was confirmed in experiments with human cells and HLA molecules, as elaborated upon infra.

EXAMPLE 13

Using the sequence of the P1A gene as weel as the amino acid sequence derivable therefrom, antigenic peptides which were $A^{+}B^{+}$ (i.e., characteristic of cells which express both the A and B antigens), and those which are $A^{-}B^{+}$ were identified. The peptide is presented in FIG. 10. This peptide when administered to samples of P815 cells in the presence of CTL cell lines specific to cells presenting it, led to lysis of the P815 cells, lending support to the view that peptides based on the product expressed by the gene can be used as vaccines.

EXAMPLE 14

The human melanoma cell line referred to hereafter as MZ2-MEL is not a clonal cell line. It expresses four stable antigens recognized by autologous CTLs, known as antigens "D, E F, and A". In addition, two other antigens "B" and "C" are expressed by some sublines of the tumor. CTL clones specific for these six antigens are described by Van den Eynde et al., Int. J. Canc. 44: 634-640 (1989). Among the recognized subclones of MZ2-MEL are MEL.43, MEL3.0 and MEL3.1. (Van den Eynde et al., supra). Cell line MEL3.1 expresses antigen E, as determined by CTL studies as described for P815 variants, supra, so it was chosen as a source for the nucleic acid sequence expressing the antigen precursor.

In isolating the pertinent nucleic acid sequence for a tumor rejection antigen precursor, the techniques developed supra, showed that a recipient cell is needed which fulfills two criteria: (i) the recipient cell must not express the TRAP of interest under normal conditions, and (ii) it must express the relevant class I HLA molecule. Also, the recipient ell must have a high transfection frequency, i.e., it must be a "goo" recipient.

In order to secure such a cell line, the clonal subline ME3.1 was subjected to repeated selection with anti-E CTL 82/30 as described by Van den Eynde, supra. The repeated cycles of selection led to isolation of subclone MZ2-MEL-2.2 isc $E^-$. This subclone is also HPRT', (i.e., sensitive to HAT medium: $10^{-4}$ M hypoxanthine, $3.8\times10^{-7}$ aminopterine, $1.6\times10^{-5}$ M 2-deoxythymidine). The subclone is referred to as "MEL-2.2" for simplicity hereafter.

EXAMPLE 15

The genomic DNA of MEL3.0 was prepared following W öfel et al., Immunogenetics 26:178-187 (1987), the disclosure of which is incorporated by reference. The plasmid pSVtkneoβ, as described by Nicolas et al., Cold Spring Harb., Conf. Cell Prolif. 10:469-485 (1983) confers geneticin resistance, so it can be used as a marker for cotransfection, as it was in this experiment.

Following a procedure similar but not identical to that of Corsao et al., Somatic Cell Molec. Genet 7:603-616 (1981), total genomic DNA and the plasmid were cotransfected. The genomic DNA (60 μg) and plasmid DNA (6 μg) were mixed in 940 μl of 1 mM Tris.HCl (pH 7.5), 0.1mM EDTA, after which 310 μl of 1M $CaCl_2$ was added. This solution was slowly added, under constant agitation, to 1.25 ml of 2×HBS (50 mMHEPES, 280 mMNaCl1.5 mM $Na_2HPO_4$, adjusted to pH 7.1 with NaOH). the calcium phosphate DNA precipitates were allowed to form for 30-45 minutes at room temperature, after which they were applied to 80 $cm^2$ tissue culture flasks which had been seeded 24 hours previously with $3\times10^6$ MEL2.2 cells, in 22.5 ml of melanoma culture medium (Dulbecco's Modified Eagle's Medium) supplemented with 10% fetal calf serum. After 24 hours, the medium was replaced. Forty eight hours after transfection, the cells were harvested and seeded at $4\times10^6$ cells per 80 $cm^2$ flask in melanoma culture medium supplemented with 2 mg/ml of geneticin. The geneticin serves as a selection marker.

EXAMPLE 16

Thirteen days after transfection, geneticin-resistant colonies were counted, harvested, and cultured in non-selective medium for 2 or 3 days. Transfected cells were then plated in 96-well microplates at 200 cells/well in 200 ul of culture medium with 20% fetal calf serum (FCS) in order to obtain approximately 30 growing colonies per well. The number of microcultures was aimed at achieving redundancy, i.e., such that every independent transfectant should be represented at least four times.

After 10 days, wells contained approximately $6\times10^4$ cells. These cells were detached, and ⅓ of each microculture was transferred to a duplicate plate. After 6 hours, i.e., after readherence, medium was removed and 1500 anti-E CTL (CTL 82/30), were added to each well in 100 μl of CTL culture medium with 35 U/ml of IL-2. One day later, the supernatant (50 μl) was harvested and examined for TNF concentration, for reasons set forth in the following example.

EXAMPLE 17

The size of the mammalian genome is $6\times10^6$ kb. As the average amount of DNA integrated in each drug-resistant transfectant was expected to be about 200 kb, a minimum of 30,000 transfectants would need to be examined to ascertain whether antigen E had been transfected. Prior work with murine cells had shown that when a CTL stimulation assay was used, groups containing only 3% of cells expressing the antigen of interested could be identified. This should reduce the number of assays by a actor of 30. While an anti-E CTL assay, as described supra, in mixed $E^+/E^-$ cells was helpful, it was not sufficient in that consistent results could not be obtained.

As a result, an alternative test was devised. Stimulation of CTLs was studied by release of tumor necrosis factor ("TNF") using well known methodologies which need to be repeated here. As described in Example 15, 1500 CTL 82/30 cells had been added per well of transfectants. These cells were collected 6 days after stimulation, and were then restimualted for 24 hours in a mixture of 40,000 $E^+$ and $E^-$ cells in mixed culture. As indicated supra, after ⅓ of the cells in each well had been removed and the remaining ⅔ ($4\times10^4$) had readhered, the CTLs and IL-2 were added thereto. The 50 μl of supernatant was removed and transferred to a microplate containing $3\times10^4$ W13 (WEHI-164 clone 13) cells in 50 μl of W13 culture medium (RPMI-1640, supplemented with L-arginine (116 mg/l), L-asparagine (36 mg/l), L-glutamine (216 mg/l), and 10% (FCS) supplemented with 2 μg of actinomycin D at 37% in an 8% $CO_2$ atmosphere. The cell line W13 is a mouse fibrosarcoma cell line sensitive to TNF. Dilutions of recombinant TNF-β in RPMI 1640 were added to target cell controls.

The W13 cultures were evaluated after 20 hours of incubation, and dead cell percentage was measured using an adaptation of the colorimetric assay of Hansen et al., J. Immunol. Meth. 119: 203-210 (1989). This involved adding 50 ml of (3-(4,5-dimethylthiazol-2-yl)-2,5-diphenyl tetrazolium bromide at 2.5 mg/ml in PBS, followed by two hours of incubation at 37° C. Dark blue formazan crystals were dissolved by adding 100 μl of lysis solution (1 volume N,N dimethyl formamide mixed at 37° C. with two volumes of water containing 30% (w/v) sodium dodecyl sulphate, at pH 4.7 from 1.6% acetic acid and 2.5% 1N HCl). Plates were incubated at 37° C. overnight, and ODs were taken at 570 nm using 650 nm as control. Dead cell percentage was determined via the formula:

$$100\times\left[1-\frac{100-(\mathrm{OD}_{570}\ \text{sample well})}{\mathrm{OD}_{570}\ \text{well}+\text{medium}}\right]$$

following Espevik et al., J. Immunol. Meth. 95:99-105 (1986). The results showed that even when the ratio of $E^+/E^-$ cells was as low as 1/45, significant production of TNF was observed, thus showing active CTLs. This led to the decision to test the drug resistant transfectants in groups of 30.

EXAMPLE 18

Cells were tested for TNF production as discussed in Example 17, supra. A total of 100 groups of $E^-$ cells ($4\times10^6$ cells/group) were tested following transfection, and $7\times10^4$ independent geneticin resistant transfectants were obtained, for an average of 700 per group. Only one group of transfected cells led to a microculture which caused anti-E antigen CTL clone 82/30 to produce TNF. Of 300 clones tested, 8 were positive. These clones were then tested for lysis by anti-E CTL, using the standard $^{51}Cr$ release assay, and were found to be lysed as efficiently as the original $E^+$ cell line. The transfectant E.T1, discussed herein, had the same lysis pattern as did MEL2.2 for CTLs against antigens B,C,D and F.

The fact that only one transfectant presented the antigen out of 70,000 geneticin resistance transfectants may at first seem very low, but it is not. The work described supra for P815 showed an average frequency of 1/13,000. Human DNA recipient MEL2.2 appears to integrate 5 times less DNA than P1.HTR.

EXAMPLE 19

Once transfectant E.T1 was found, analysis had to address several questions including whether an $E^+$ contaminant of the cell population was the cause. The analysis of antigert presentation, described supra, shows that E.T1 is $B^-$ and $C^-$, just like the recipient cell MEL2.2. It was also found to be $HPRT^-$, using standard selection procedures. All $E^+$ cells used in the work described herein, however, were $HPRT^{30}$ .

It was also possible that an $E^+$ revertant of MEL2.2 was the source for E.T1. To test this, the observation by Perucho et al., Cell 22:309-317 (1980), that cotransfected sequences usually integrate together at a single location of recipient genome was employed. If antigen E in a transfectant results from cotransfection with pSVtkneoβ, then sequences should be linked and deletion of the antigen might also delete the neighboring pSVtkneoβ sequences. Wölfel et al., supra, has shown this to be true. If a normally $E^-$ cell is transfected with pSVtkneoβ, then sequences should be linked and deletion of the antigen might also delete the neighboring pSVtkneoβ sequences. If a normally $E^+$ cell transfected with pSVtkneoβ is E.T1, however, "co-deletion" should not take place. To test this, the transfectant E.T1 was subjected to immunoselection with 82/30, as described supra. Two antigen loss variants were obtained, which resisted lysis by this CTL. Neither of these had lost geneticin resistance; however, Southern blot analysis showed loss of several $neo^r$ sequences in the variants, showing close linkage between the E gene and $neo^r$ gene in E.T1, leading to the conclusion that E.T1 was a transfectant.

EXAMPLE 20

The transfectant E.T1 was used as a source of DNA for preparation of a cosmid library. This library of nearly 50,000 cosmids was transfected into MZ2-MEL 2.2 cells, following the cosmid transfection protocols described supra. One cosmid, referred to as B3, was recovered from this experiment, and subjected to restriction endonuclease digestion via SmaI, or by BamHI digestion of a large, 12 kb SmaI transfected fragment. The fragments were cloned into vector pTZ 18, and then into MEL2.2. Again, TNF production was the measure by which successful transfection was determined. The experiments led to the determination of a gene sequence capable of transfecting antigen E on the 12 kb SmaI fragment, and then on the 2.4 kb fragment of BamHI digestion of the 12 kb segment.

Figure 15:
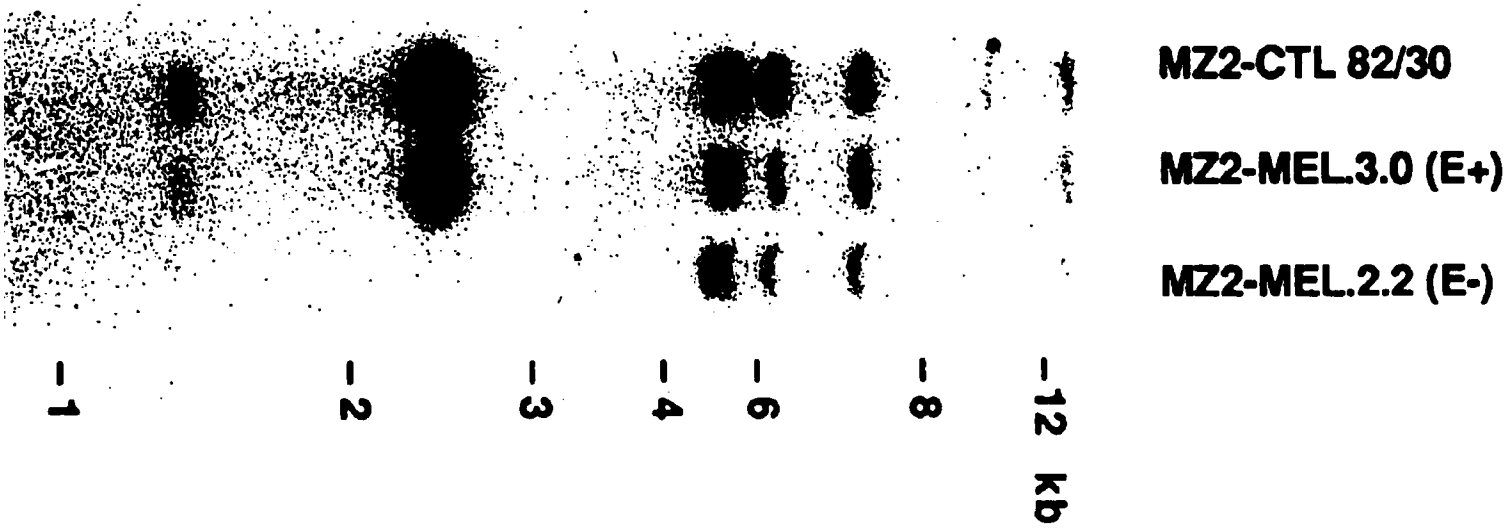
FIG. 15 shows Southern Blot experiments using the various human melanoma cell lines employed in this application.
Figure 16:
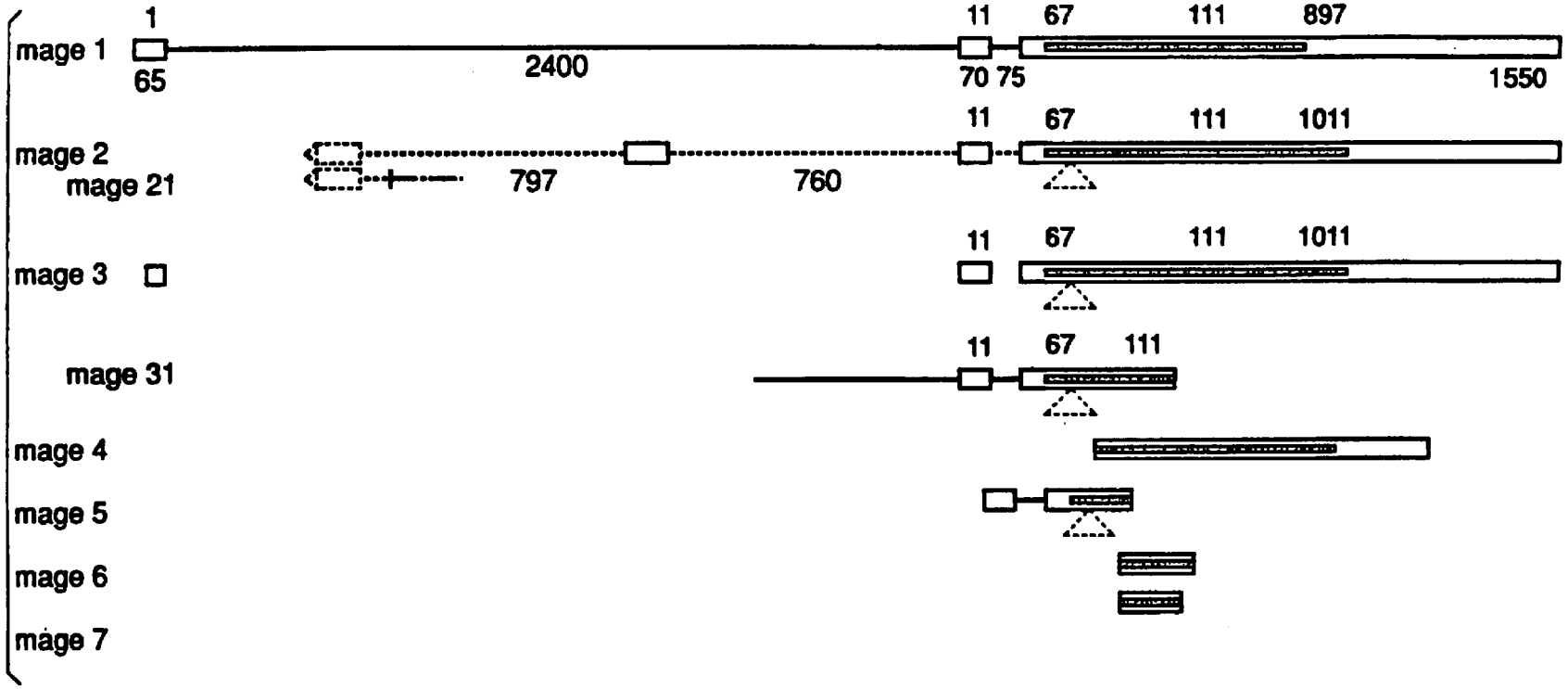
FIG. 16 is a generalized schematic of the location of sections of MAGE genes.

The 2.4 kb fragment hybridizes with a 2.4 kb fragment from MZ2-MEL and with a T cell clone of patient MZ-2, as determined by Southern Blot (BamHI/SmaI digested DNA). The band is absent from E' antigen loss variants of MZ2-MEL, as seen in FIG. 15.

The sequence for the E antigen precursor gene has been determined, and is presented herein:

```
          |   10       |   20       |   30       |   40       |   50       |   60
   1 GGATCCAGGC CCTGCCAGGA AAAATATAAG GGCCCTGCGT GAGAACAGAG GGGGTCATCC    60
  61 ACTGCATGAG AGTGGGGATG TCACAGAGTC CAGCCCACCC TCCTGGTACG ACTGAGAAGC   120
 121 CAGGGCTGTG CTTGCGGTCT GCACCCTGAG GGCCCGTGGA TTCCTCTTCC TGGAGCTCCA   180
 181 GGAACCAGGC AGTGAGGCCT TGGTCTGAGA CAGTATCCTC AGGTCACAGA GCAGAGGATG   240
 241 CACAGGGTGT GCCAGCAGTG AATGTTTGCC CTGAATGCAC ACCAAGGGCC CCACCTGCCA   300
 301 CAGGACACAT AGGACTCCAC AGAGTCTGGC CTCACCTCCC TACTGTCAGT CCTGTACAAT   360
 361 CGACCTCTGC TGGCCGGCTG TACCCTGAGT ACCCTCTCAC TTCCTCCTTC AGGTTTTCAG   420
 421 GGGACAGGCC AACCCAGAGG ACAGGATTCC CTGGAGGCCA CAGAGGAGCA CCAAGGAGAA   480
 481 GATCTGTAAG TAGGCCTTTG TTAGAGTCTC CAAGGTTCAG TTCTCAGCTG AGGCCTCTCA   540
 541 CACACTCCCT CTCTCCCCAG GCCTGTGGGT CTTCATTGCC CAGCTCCTGC CCACACTCCT   600
 601 GCCTGCTGCC CTGACGAGAG TCATCATGTC TCTTGAGCAG AGGAGTCTGC ACTGCAAGCC   660
 661 TGAGGAAGCC CTTGAGGCCC AACAAGAGGC CCTGGGCTGG TGTGTGTGCA GGCTGCCACC   720
 721 TCCTCCTCCT CTCCTCTGGT CCTGGGCACC CTGGAGGAGG TGCCCACTGC TGGGTCAACA   780
 781 GATCCTCCCC AGAGTCCTCA GGGAGCCTCC GCCTTTCCCA CTACCATCAA CTTCACTCGA   840
 841 CAGAGGCAAC CCAGTGAGGG TTCCAGCAGC CGTGAAGAGG AGGGGCCAAG CACCTCTTGT   900
 901 ATCCTGGAGT CCTTGTTCCG AGCAGTAATC ACTAAGAAGG TGGCTGATTT GGTTGGTTTT   960
 961 CTGCTCCTCA AATATCGAGC CAGGGAGCCA GTCACAAAGG CAGAAATGCT GGAGAGTGTC  1020
1021 ATCAAAAATT ACAAGCACTG TTTTCCTGAG ATCTTCGGCA AAGCCTCTGA GTCCTTGCAG  1080
1081 CTGGTCTTTG GCATTGACGT GAAGGAAGCA GACCCCACCG GCCACTCCTA TGTCCTTGTC  1140
1141 ACCTGCCTAG GTCTCTCCTA TGATGGCCTG CTGGGTGATA ATCAGATCAT GCCCAAGACA  1200
```

-continued

```
1201 GGCTTCCTGA TAATTGTCCT GGTCATGATT GCAATGGAGG GCGGCCATGC TCCTGAGGAG 1260
1261 GAAATCTGGG AGGAGCTGAG TGTGATGGAG GTGTATGATG GGAGGGAGCA CAGTGCCTAT 1320
1321 GGGGAGCCCA GGAAGCTGCT CACCCAAGAT TTGGTGCAGG AAAAGTACCT GGAGTACGGC 1380
1381 AGGTGCCGGA CAGTGATCCC GCACGCTATG AGTTCCTGTG GGGTCCAAGG GCCCTCGCTG 1440
1441 AAACCAGCTA TGTGAAAGTC CTTGAGTATG TGATCAAGGT CAGTGCAAGA GTTCGCTTTT 1500
1501 TCTTCCCATC CCTGCGTGAA GCAGCTTTGA GAGAGGAGGA AGAGGGAGTC TGAGCATGAG 1560
1561 TTGCAGCCAA GGCCAGTGGG AGGGGGACTG GGCCAGTGCA CCTTCCAGGG CCGCGTCCAG 1620
1621 CAGCTTCCCC TGCCTCGTGT GACATGAGGC CCATTCTTCA CTCTGAAGAG AGCGGTCAGT 1680
1681 GTTCTCAGTA GTAGGTTTCT GTTCTATTGG GTGACTTGGA GATTTATCTT TGTTCTCTTT 1740
1741 TGGAATTGTT CAAATGTTTT TTTTTAAGGG ATGGTTGAAT GAACTTCAGC ATCCAAGTTT 1800
1801 ATGAATGACA GCAGTCACAC AGTTCTGTGT ATATAGTTTA AGGGTAAGAG TCTTGTGTTT 1860
1861 TATTCAGATT GGGAAATCCA TTCTATTTTG TGAATTGGGA TAATAACAGC AGTGGAATAA 1920
1921 GTACTTAGAA ATGTGAAAAA TGAGCAGTAA AATAGATGAG ATAAAGAACT AAAGAAATTA 1980
1981 AGAGATAGTC AATTCTTGCC TTATACCTCA GTCTATTCTG TAAAATTTTT AAAGATATAT 2040
2041 GCATACCTGG ATTTCCTTGG CTTCTTTGAG AATGTAAGAG AAATTAAATC TGAATAAAGA 2100
2101 ATTCTTCCTG TTCACTGGCT CTTTTCTTCT CCATGCACTG AGCATCTGCT TTTTGGAAGG 2160
2161 CCCTGGGTTA GTAGTGGAGA TGCTAAGGTA AGCCAGACTC ATACCCACCC ATAGGGTCGT 2220
2221 AGAGTCTAGG AGCTGCAGTC ACGTAATCGA GGTGGCAAGA TGTCCTCTAA AGATCTAGGG 2280
2281 AAAAGTGAGA GAGGGGTGAG GGTGTGGGGC TCCGGGTGAG AGTGGTGGAG TGTCAATGCC 2340
2341 CTGAGCTGGG GCATTTTGGG CTTTGGGAAA CTGCAGTTCC TTCTGGGGGA GCTGATTGTA 2400
2401 ATGATCTTGG GTGGATCC                                                2418
         |   10      |   20      |   30      |   40      |   50      |   60
```

EXAMPLE 21

Figures 10, 11:
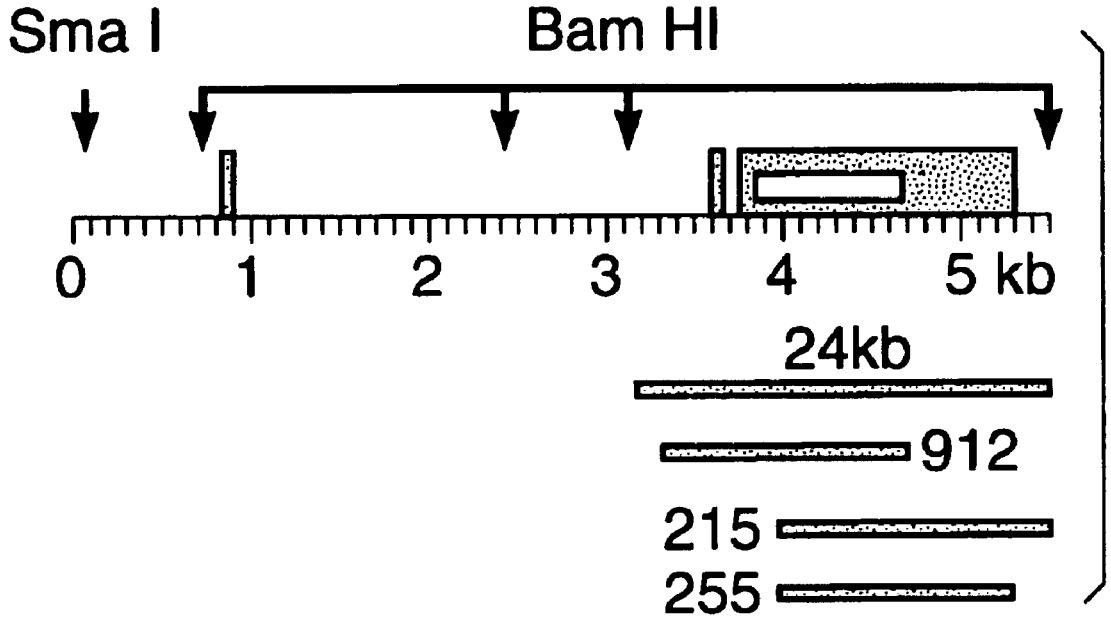
FIG. 10 sets forth the amino acid sequence of antigenic peptides for the P1A TRA (*the amino acids presented at positions 35-41 of SEQ ID NO: 2, and SEQ ID NO: 7*). The sequence is for cells which are $A^+$, $B^+$, i.e., express both the A and B antigens. The peptide corresponding to phenotype $A^-B^+$ is identical, except for a change from valine to alanine at position 18.
FIG. 11 is a map of subfragments of the 2.4 kb antigen E fragment sequence which also express the antigen.

After the 2.4 kb genomic segment had been identified, studies were carried out to determine if an "$E^+$" subline expressed any homologous DNA. Cell line MZ2-MEL 3.0 was used as a source, and a cDNA library was prepared from its mRNA, using art known techniques. The 2.4 kb segment was used as a probe, and mRNA of about 1.8 kb was identified as homologous, using Northern blot analysis. When cDNA was screened, clones were obtained showing almost complete identity to parts of the 2.4 kb fragment. Two exons were thus identified. An additional exon was located upstream of these, via sequencing segments of cosmid B3 located in front of the 2.4 kb BamHI fragment. The gene extends over about 4.5 kb, as shown in FIG. 11. The starting point of the transcribed region was confirmed using PCR for the 5' end of the cDNA. The three exons comprise 65, 73, and 1551 base pairs. An ATG is located at position 66 of exon3, followed by an 828 base pair reading frame.

EXAMPLE 22

To determine if smaller segments of the 2.4 kb fragment could transfer the expression of antigen E, smaller pieces corresponding to the larger gene were prepared, using art recognized techniques, and transferred into $E^-$ cells. FIG. 11 shows the boundaries of the three segments.

Transfer of antigen expression in this manner indicates that the gene codes for the antigen precursor, rather than coding for a protein which activates the antigen.

EXAMPLE 23

The probing of cDNA described Supra revealed, surprisingly, two different but closely related cDNAs. These cDNAs, when tested, did not transfer expression of antigen E, but hey do show substantial homology to the first cDNA segment. The three segments, appear to indicate a newly recognized family of genes, referred to as "MAGE" for "melanoma antigen". In FIG. 12, "mage-1" directs expression of the antigen from MZ2 cells. Portions of the third exon of each gene are presented in FIG. 12. The second and third sequences are more closely related to each other than the first (18.1 and 18.9% difference compared to the first; 12% with each other). Out of 9 cDNA clones obtained, three of each type were obtained, suggesting equal expression. "MAGE" as used hereafter refers to a family of molecules, and the nucleic acids coding for them. These nucleic acids share a certain degree of homology and are expressed in tumor cells including several types of human tumor cells as well as in human tumors. The family is referred to as "MAGE" because the first members were identified in human melanoma cells. As the experiments which follow indicate, however, the members of the MAGE family are not at all restricted to melanoma tumors; rather, MAGE refers to a family of tumor rejection antigen precursors and the nucleic acid sequences coding therefore. The antigens resulting therefrom are referred to herein as "MAGE TRAs" or "melanoma antigen tumor rejection antigens".

EXAMPLE 24

Experiments with mouse tumors have demonstrated that new antigens recognized by T cells can result from point mutations that modify active genes in a region that codes for the new antigenic peptide. New antigens can also arise from the activation of genes that are not expressed in most normal cells. To clarify this issue for antigen MZ2-E, the mage-1 gene present in the melanoma cells was compared to that present in normal cells of patient MZ2. Amplification by polymerase chain reaction (PCR) DNA of phytohemagglutinin-activated blood lymphocytes using primers surrounding a 1300 bp stretch covering the first half of the 2.4 kb fragment was carried out. As expected, a PCR product was obtained whereas none was obtained with the DNA of the $E^-$ variant. The sequence of this PCR product proved identical to the corresponding sequence of the gene carried by the $E^+$ melanoma cells. Moreover, it was found that antigen MZ2-E was expressed by cells transfected with the cloned PCR product. This result suggests that the activation of a gene normally silent is responsible for the appearance of tumor rejection antigen MZ2-E.

EXAMPLE 25

Figure 13:
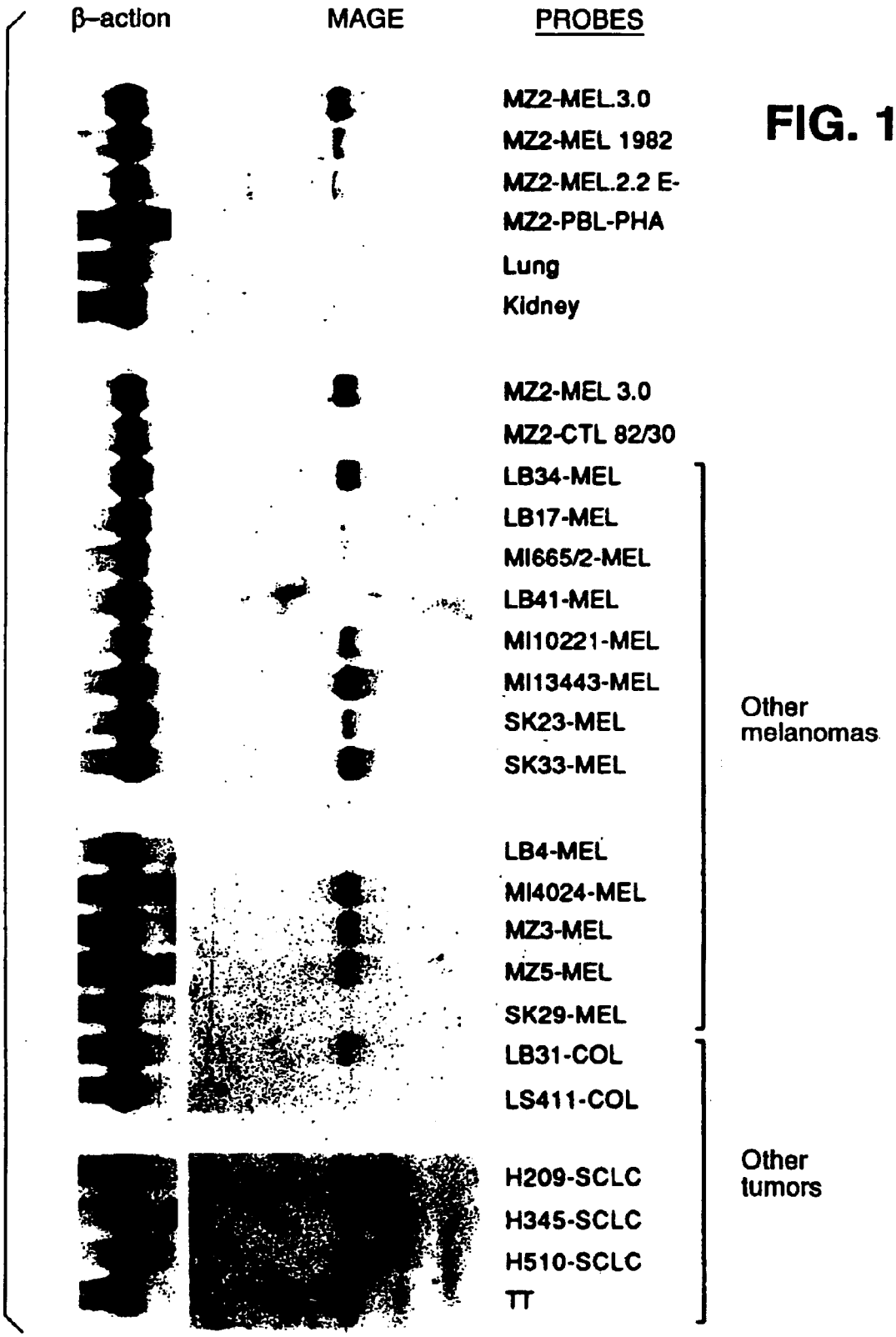
FIG. 13 shows the result of Northern blots for MAGE genes on various tissues.

In order to evaluate the expression of gene mage-1 by various normal and tumor cells, Northern blots were hybridized with a probe covering most of the third exon. In contrast with the result observed with human tumor cell line MZ2-MEL 3.0, no band was observed with RNA isolated from a CTL clone of patient MZ2 and phytohemagglutinin-activated blood lymphocytes of the same patient. Also negative were several normal tissues of other individuals (FIG. 13 and FIG. 14). Fourteen melanoma cell lines of other patients were tested. Eleven were positive with bands of varying intensities. In addition to these culture cell lines, four samples of melanoma tumor tissue were analyzed. Two samples, including a metastasis of patient MZ2 proved positive, excluding the possibility that expression of the gene represented a tissue culture artefact. A few tumors of other histological types, including lung tumors were tested. Most of these tumors were positive (FIGS. 13 and 14). These results idiated that the MAGE gene family is expressed by many melanomas and also by other tumors. However, they provided no clear indication as to which of genes mage-1, 2 or 3 were expressed by these cells, because the DNA probes corresponding to the three genes cross-hybridized to a considerable extent. To render this analysis more specific, PCR amplification and hybridization with highly specific oligonucleotide probes were used. cDNAs were obtained and amplified by PCR using oligonucleotide primers corresponding to sequences of exon 3 that were identical for the three MAGE genes discussed herein. The PCR products were then tested for their ability to hybridize to three other oligonucleotides that showed complete specificity for one of the three genes (FIG. 12). Control experiments carried out by diluting RNA of melanoma MZ2-MEL 3.0 in RNA from negative cells indicated that under the conditions used herein the intensity of the signal decreased proportionally to the dilution and that positive signals could still be detected at a dilution of 1/300. The normal cells (lymphocytes) that were tested by PCR were confirmed to be negative for the expression of the three MAGE genes, suggesting therefore a level of expression of less than $1/300^{th}$ that of the MZ2 melanoma cell line (FIG. 14). For the panel of melanoma cell lines, the results clearly showed that some melanomas expressed MAGE genes mage 1, 2 and 3 whereas other expressed only mage-2 and 3 (FIGS. 14 and 13 and Table 1). Some of the other tumors also expressed all three genes whereas others expressed only mage-2 and 3 or only mage-3. It is impossible to exclude formally that some positive PCR results do not reflect the expression of one of the three characterized MAGE genes but that of yet another closely related gene that would share the sequence of the priming and hybridizing oligonucleotides. It can be concluded that the MAGE gene family is expressed by a large array of different tumors and that these genes are silent in the normal cells tested to this point.

EXAMPLE 26

The availability of a sequence that transfects at high efficiency and expressed a TRAP very well made it possible to search for the associated major histocompatibility complex (MHC) class I molecule. The class I specificities of patient MZ2 are HLA-A1, A29, B37, B44 and C6. Four other melanomas of patients that had A1 in common with MZ2 were cotransfected with the 2.4 kg fragment and pSVtkneoβ. Three of them yielded $neo^r$ transfectants that stimulated TNF release by anti-E CTL clone 82/30, which is CDS+ (FIG. 13). No E-transfectant was obtained with four other melanomas, some of which shared A29, B44 or C6 with MZ2. This suggests that the presenting molecule for antigen MZ2-E is HLA-A1. In confirmation, it was found that, to of 6 melanoma cell lines derived from tumors of HLA-A1 patients, two simulated TNF release by anti-E CTL clone 82/30 of patient MZ2. One of these tumor cell lines, MI13443-MEL also showed high sensitivity to lysis by these anti-E CTL. These two melanomas were those that expressed mage-1 gene (FIG. 13). Eight melanomas of patients with HLA haplotypes that did not include A1 were examined for their sensitivity to lysis and for their ability to simulate TNF release by the CTL. None was found to be positive. The ability of some human anti-tumor CTL to lyse allergenic tumors sharing an appropriate HLA, specificity with the original tumor has been reported previously (Darrow, et al., J. Immunol. 142:3329 (1989)). It is quite possible that antigenic peptide encoded by genes mage 2 and 3 can also be presented to autologous CTL by HLA-A1 or other class I molecules, especially in view of the similar results found with murine tumors, as elaborated upon supra.

EXAMPLE 27

As indicated supra, melanoma MZ2 expressed antigens F, D and A', in addition to antigen E Following the isolation of the nucleic acid sequence coding for antigen E, similar experiments were carried out to isolate the nucleic acid sequence coding for antigen F.

To do this, cultures of cell line MZ2-MEL2.2, and $E^-$ cell line described supra, were treated with anti-F CTL clone 76/6, in the same manner described for treatment with anti-E CTL clones. This resulted in the isolation of an F antigen loss variant, which was then subjected to several rounds of selection. The resulting cell line, "MZ2-MEL2.2.5" was completely resistant to lysis by anti-F CTLs, yet proved to be lysed by anti-D CTLs.

Again, following the protocols set forth for isolation of antigen-E precursor DNA, the $F^-$ variant was transfected with genomic DNA from $F^+$ cell line MZ2-MEL3.0. The experiments yielded 90,000 drug resistant transfectants. These were tested for MZ2F expression by using pools of 30 cells in the TNF detection assay elaborated upon supra. One pool stimulated TNF release by anti-F CTLs, and was cloned. Five of 145 clones were found to stimulate anti-F CTLs. Lysis assays, also following protocols described supra, confirmed (i) expression of the gene coding for antigen F, and (ii) presentation of antigen F itself.

EXAMPLE 28

Following identification of $F^+$ cell lines, the DNA therefrom was used to transfect cells. To do this, a cosmid library of $F^+$ cell line MZ2-MEL.43 was prepared, again using the protocols described supra. The library was divided into 14 groups of about 50,000 cosmids, and DNA from each group was transfected into MZ2-MEL2.2.5. Transfectants were then tested for their ability to stimulate TNF release from anti-F CTL clone 76/6. Of 14 groups of cosmids, one produced two independent transfectants expressing antigen F; a yield of two positives out of 17,500 geneticin resistant transfectants.

EXAMPLE 29

The existence of a gene family was suggested by the pattern observed on the Southern blot. To do this, the 2.4 kb BamHI fragment, which transferred the expression of antigen M22-E, was labelled with 32p and used as a probe on a Southern Blot of BamHI digested DNA of E+ cloned subclone M22-MEL2.2. Hybridization conditions included 50 μl/cm$^2$ of 3.5×SSC, 1×Denhardt's solution; 25 mM sodium phosphate buffer (pH 7.0), 0.5% SDS, 2mM EDTA, where the 2.4 kb probes had been labelled with [a$^{32}$p]dCTP (2-3000 Ci/mode), at 3×10$^6$ cpm/ml. Hybridization was carried out for 18 hours at 65° C. After this, the membranes were washed at 65° C. four times for one hour each in 2×SSC, 0.1% SDS, and finally for 30 minutes in 0.1×SSC, 0.1% SDS. To identify hybridization, membranes were autoradiographed using Kodak X-AR film and Kodak X-Omatic fine intensifying screens.

In the following examples, whenever "hybridization" is referred to, the stringency conditions used were similar to those described supra. "Stringent conditions" as used herein thus refers to the foregoing conditions; subject to routine, art recognized modification.

EXAMPLE 30

The DNA coding for mage 4 was identified from a sample of human sarcoma cell line LB23-SAR. This cell line was found to not express mage 1, 2 or 3, but the mRNA of the cell line did hybridize to the 2.4 kb sequence for mage 1. To study this further, a cDNA library was prepared from total LB23-SAR mRNA, and was then hybridized to the 2.4 kb fragment. A cDNA sequence was identified as hybridizing to this probe, and is identified hereafter as mage 4.

EXAMPLE 31

Experiments were carried out using PHA-activated lymphocytes from patient "MZ2" the source of the "MZ" cells discussed supra. An oligonucleotide probe which showed homology to mage 1 but not mage 2 or 3 was hybridized with a cosmid library derived from the PHA activated cells. The size of the hybridizing BamHI cosmid fragment, however, was 4.5 kb, thus indicating that the material was not mage 1; however, on the basis of homology to mage 1-4, the fragment can be referred to as "mage 5". A portion of its sequence is presented in the figures.

EXAMPLE 32

Melanoma cell line LB-33-MEL was tested. Total mRNA from the cell line was used to prepare cDNA, which was then amplified with oligos CHO9: (ACTCAGCTCCTCCCAGATTT) (*SEQ ID NO: 17*), and CHO10: (GAAGAGGAGGGGCCAAG) (*SEQ ID NO: 18*). These oligos correspond to regions of exon 3 that are common to previously described mage 1, 2 and 3.

To do this, 1 μg of RNA was diluted to a total volume of 20 μl, using 2 μl of 10×PCR buffer, 2 μl of each of 10 mM dNTP, 1.2 μl of 25 mM $MgCl_2$, 1 μl of an 80 mM solution of CHO9, described supra, 20 units of RNAs in, and 200 units of M-MLV reverse transciptase. This was followed by incubation for 40 minutes at 42° C. PCR amplification followed, using 8 μl of 10×PCR buffer, 4.8 μl of 25 mM $MgCl_2$, 1 μl of CHO10, 2.5 units of Thermus acquaticus ("Taq") polymerase, and water to a total volume of 100 μl. Amplification was then carried out for 30 cycles (1 minute 94° C.; 2 minutes at 52° C., 3 minutes at 72° C.). Ten μl of each reaction were then size fractionated on agarose gel, followed by nitrocellulose blotting. The product was found to hybridize with oligonucleotide probe CHO18 (TCTTGTATCCTGGAGTCC) (*SEQ ID NO: 19*). This probe identified mage 1 but not mage 2 or 3. However, the product did not hybridize to probe SEQ 4 (TTGCCAAGATCTCAGGAA) (*SEQ ID NO: 20*). This probe also binds mage 1 but not 2 and 3. This indicated that the PCR product contained a sequence that differed from mage 1, 2 and 3. Sequencing of this fragment also indicated differences with respect to mage 4 and 5. These results indicate a sequence differing from previously identified mage 1, 2, 3, 4 and 5, and is named mage 6.

EXAMPLE 33

In additional experiments using cosmid libraries from PHA-activated lymphocytes of MZ2, the 2.4 kb mage 1 fragment was used as a probe and isolated a complementary fragment. This clone, however, did not bind to oligonucleotides specific for mage 1, 2, 3 or 4. The sequence obtained shows some homology to exon 3 of mage 1, and differs from mages 1-6. It is referred to as mage 7 hereafter.

EXAMPLE 34

The usefulness of the TRAPs, as well as TRAs derived therefrom, was exemplified by the following.

Exon 3 of mage 1 was shown to transfer expression of antigen E. As a result, it was decided to test whether synthetic peptide derived from this exon 3 could be used to confer sensitivity to anti-E CTL.

To do this, and using standard protocols, cells normally insensitive to anti-E/CTLs were incubated with the synthetic peptide derived from:

Asp-Val-Lys-Glu-Ala-Asp-Pro-Thr-Gly-His-Ser-Tyr-Val-Leu-Val. Using the CTL lytic assays described supra on P815A, and a peptide concentration of 3 mM, the assay showed lysis of 30%, including conferring of sensitivity to the anti-E CTL.

The foregoing disclosure, including the examples, places many tools of extreme value in the hands of the skilled artisan. To begin, the examples identify and provide a methodology for isolating nucleic acid molecules which code for tumor rejection antigen precursors as well as the nucleic acid molecules complementary thereto. It is known that DNA exists in double stranded form, and that each of the two strands is complementary to the other. Nucleic acid hybridization technology had developed to the point where, given a strand of DNA, the skilled artisan can isolate its complement, or synthesize it.

"Nucleic acid molecule" as used herein refers to all species of DNA and RNA which posses the properties discussed supra. Genomic and complementary DNA, or "cDNA" both code for particular proteins, and as the examples directed to isolation of MAGE coding sequences show, this disclosure teaches the artisan how to secure both of these.

Similarly, RNA molecules, such as mRNA can be secured. Again, with reference to the skilled artisan, once one has a coding sequence in hand, mRNA can be isolated or synthesized.

Complementary sequences which do not code for TRAP, such as "antisense DNA" or mRNA are useful, e.g., in probing for the coding sequence as well as in methodologies for blocking its expression.

It will also be clear that the examples show the manufacture of biologically pure cultures of cell lines which have been transfected with nucleic acid sequences which code for or express the TRAP molecules. Such cultures can be used as a source for tumor rejection antigens, e.g., or as therapeutics. This aspect of the invention is discussed infra.

Cells transfected with the TRAP coding sequences may also be transfected with other coding sequences. Examples of other coding sequences include cytokine genes, such as interleukins (e.g., IL-2 or IL-4), or major histocombatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions.

Transfection with an MHC/HLA coding sequence is desirable because certain of the TRAs may be preferentially or specifically presented only by particular MHC/HLA molecules. Thus, where a recipient cell already expresses the MHC/HLA molecule associated with presentation of a TRA, additional transfection is not necessary. On the other hand, it may be desirable to transfect with a second sequence when the recipient cell does not normally express the relevant MHC/HLAmolecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure" but the recitation will establish this fully.

Transfection of cells requires that an appropriate vector be used. Thus, the invention encompasses expression vectors where a coding sequence for the TRAP of interest is operably linked to a promoter. The promoter may be a strong promoter, such as those well known to the art, or a differential promoter, i.e., one which is operative only in specific cell types.

The expression vectors may incorporate several coding sequences, as long as the TRAP sequence is contained therein. The cytokine and/or MHC/HLA genes discussed supra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well know technique, and the artisan in this field is expected to have this technology available for utilization.

As the foregoing discussion makes clear, the sequences code for "tumor rejection antigen precursors" ("TRAPs") which, in turn, are processed into tumor rejection antigens ("TRAs"). Isolated forms of both of these categories are descried herein, including specific examples of each. Perhaps their most noteworthy aspect is as vaccines for treating various cancerous conditions. The evidence points to presentation of TRAs on tumor cells, followed by the development of an immune response and deletion of the cells. The examples show that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, present cells may be used in the same manner, either alone or as combined with ingredients to yield pharmaceutical compositions.

The generation of an immune response, be it T-cell or B-cell related, is characteristic of the effect of the presented tumor rejection antigen. With respect to the B-cell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monclonal, the latter being prepared by any of the well recognized methodologies for their preparation which need not be repeated here. For example, mAbs may be prepared using an animal model, e.g., a Balb/C mouse or in a test tube, using, e.g., EBV transfomants. In addition, antiserum may be isolated from a subject afflicted with a cancerous condition where certain cells present a TRA.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines has already been discussed supra. Similarly, one may develop the specific CTLs in vitro and then administer these to the subject. Antibodies may be administered, either polyclonal or moncolonal, which specifically bind to cells presenting the TRA of interest. These antibodies may be coupled to specific anti tumor agents, including, but not being limited to, methotrexate radioiodinated compounds, toxins such as ricin, and so forth. Thus, "targeted" antibody therapy is included herein, as is the application of deletion of the cancerous cells by the use of CTLs.

The terms and expressions which have been employed are used as terms of description and not of limitation, and thrre is no intensoin in the use of such terms and expressions of excluding any equivalents of the features shown and described or portions thereof, it being recognized that various modifications are possible within the scope of the invention.

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
(A) LENGTH: 462 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 1:

```
ACCACAGGAG AATGAAAAGA ACCCGGGACT CCCAAAGACG CTAGATGTGT GAAGATCCTG     60

ATCACTCATT GGGTGTCTGA GTTCTGCGAT ATTCATCCCT CAGCCAATGA GCTTACTGTT    120

CTCGTGGGGG GTTTGTGAGC CTTGGGTAGG AAGTTTTGCA AGTTCCGCCT ACAGCTCTAG    180

CTTGTGAATT TGTACCCTTT CACGTAAAAA AGTAGTCCAG AGTTTACTAC ACCCTCCCTC    240

CCCCCTCCCA CCTCGTGCTG TGCTGAGTTT AGAAGTCTTC CTTATAGAAG TCTTCCGTAT    300

AGAACTCTTC CGGAGGAAGG AGGGAGGACC CCCCCCCTTT GCTCTCCCAG CATGCATTGT    360

GTCAACGCCA TTGCACTGAG CTGGTCGAAG AAGTAAGCCG CTAGCTTGCG ACTCTACTCT    420

TATCTTAACT TAGCTCGGCT TCCTGCTGGT ACCCTTTGTG CC                       462
```

(2) INFORMATION FOR SEQ ID NO: 2:

(i) SEQUENCE CHARACTERISTICS:
(A) LENGTH: 675 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 2:

```
ATG TCT GAT AAC AAG AAA CCA GAC AAA GCC CAC AGT GGC TCA GGT GGT       48
Met Ser Asp Asn Lys Lys Pro Asp Lys Ala His Ser Gly Ser Gly Gly
                5                   10                  15

GAC GGT GAT GGG AAT AGG TGC AAT TTA TTG CAC CGG TAC TCC CTG GAA       96
Asp Gly Asp Gly Asn Arg Cys Asn Leu Leu His Arg Tyr Ser Leu Glu
            20                  25                  30

GAA ATT CTG CCT TAT CTA GGG TGG CTG GTC TTC GCT GTT GTC ACA ACA      144
Glu Ile Leu Pro Tyr Leu Gly Trp Leu Val Phe Ala Val Val Thr Thr
        35                  40                  45

AGT TTT CTG GCG CTC CAG ATG TTC ATA GAC GCC CTT TAT GAG GAG CAG      192
Ser Phe Leu Ala Leu Gln Met Phe Ile Asp Ala Leu Tyr Glu Glu Gln
    50                  55                  60

TAT GAA AGG GAT GTG GCC TGG ATA GCC AGG CAA AGC AAG CGC ATG TCC      240
Tyr Glu Arg Asp Val Ala Trp Ile Ala Arg Gln Ser Lys Arg Met Ser
65                  70                  75                  80

TCT GTC GAT GAG GAT GAA GAC GAT GAG GAT GAT GAG GAT GAC TAC TAC      288
Ser Val Asp Glu Asp Glu Asp Asp Glu Asp Asp Glu Asp Asp Tyr Tyr
                85                  90                  95

GAC GAC GAG GAC GAC GAC GAC GAT GCC TTC TAT GAT GAT GAG GAT GAT      336
Asp Asp Glu Asp Asp Asp Asp Asp Ala Phe Tyr Asp Asp Glu Asp Asp
            100                 105                 110

GAG GAA GAA GAA TTG GAG AAC CTG ATG GAT GAT GAA TCA GAA GAT GAG      384
Glu Glu Glu Glu Leu Glu Asn Leu Met Asp Asp Glu Ser Glu Asp Glu
```

-continued

```
        115                 120                 125

GCC GAA GAA GAG ATG AGC GTG GAA ATG GGT GCC GGA GCT GAG GAA ATG      432
Ala Glu Glu Glu Met Ser Val Glu Met Gly Ala Gly Ala Glu Glu Met
    130                 135                 140

GGT GCT GGC GCT AAC TGT GCC TGT GTT CCT GGC CAT CAT TTA AGG AAG      480
Gly Ala Gly Ala Asn Cys Ala Cys Val Pro Gly His His Leu Arg Lys
145                 150                 155                 160

AAT GAA GTG AAG TGT AGG ATG ATT TAT TTC TTC CAC GAC CCT AAT TTC      528
Asn Glu Val Lys Cys Arg Met Ile Tyr Phe Phe His Asp Pro Asn Phe
                165                 170                 175

CTG GTG TCT ATA CCA GTG AAC CCT AAG GAA CAA ATG GAG TGT AGG TGT      576
Leu Val Ser Ile Pro Val Asn Pro Lys Glu Gln Met Glu Cys Arg Cys
            180                 185                 190

GAA AAT GCT GAT GAA GAG GTT GCA ATG GAA GAG GAA GAA GAA GAA GAG      624
Glu Asn Ala Asp Glu Glu Val Ala Met Glu Glu Glu Glu Glu Glu Glu
        195                 200             205

GAG GAG GAG GAG GAA GAG GAA ATG GGA AAC CCG GAT GGC TTC TCA CCT      672
Glu Glu Glu Glu Glu Glu Glu Met Gly Asn Pro Asp Gly Phe Ser Pro
210                 215                 220                 225

TAG                                                                  675
```

(2) INFORMATION FOR SEQ ID NO: 3:

(i) SEQUENCE CHARACTERISTICS:
(A) LENGTH: 228 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 3:

```
GCATGCAGTT GCAAAGCCCA GAAGAAAGAA ATGGACAGCG GAAGAAGTGG TTGTTTTTTT     60

TTCCCCTTCA TTAATTTTCT AGTTTTTAGT AATCCAGAAA ATTTGATTTT GTTCTAAAGT    120

TCATTATGCA AAGATGTCAC CAACAGACTT CTGACTGCAT GGTGAACTTT CATATGATAC    180

ATAGGATTAC ACTTGTACCT GTTAAAAATA AAAGTTTGAC TTGCATAC                 228
```

(2) INFORMATION FOR SEQ ID NO: 4:

(i) SEQUENCE CHARACTERISTICS:
(A) LENGTH: 1365 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 4:

```
ACCACAGGAG AATGAAAAGA ACCCGGGACT CCCAAAGACG CTAGATGTGT                50

GAAGATCCTG ATCACTCATT GGGTGTCTGA GTTCTGCGAT ATTCATCCCT               100

CAGCCAATGA GCTTACTGTT CTCGTGGGGG GTTTGTGAGC CTTGGGTAGG               150

AAGTTTTGCA AGTTCCGCCT ACAGCTCTAG CTTGTGAATT TGTACCCTTT               200

CACGTAAAAA AGTAGTCCAG AGTTTACTAC ACCCTCCCTC CCCCCTCCCA               250

CCTCGTGCTG TGCTGAGTTT AGAAGTCTTC CTTATAGAAG TCTTCCGTAT               300

AGAACTCTTC CGGAGGAAGG AGGGAGGACC CCCCCCCTTT GCTCTCCCAG               350

CATGCATTGT GTCAACGCCA TTGCACTGAG CTGGTCGAAG AAGTAAGCCG               400

CTAGCTTGCG ACTCTACTCT TATCTTAACT TAGCTCGGCT TCCTGCTGGT               450
```

-continued

```
ACCCTTTGTG CC                                                    462

ATG TCT GAT AAC AAG AAA CCA GAC AAA GCC CAC AGT GGC TCA          504

GGT GGT GAC GGT GAT GGG AAT AGG TGC AAT TTA TTG CAC CGG          546

TAC TCC CTG GAA GAA ATT CTG CCT TAT CTA GGG TGG CTG GTC          588

TTC GCT GTT GTC ACA ACA AGT TTT CTG GCG CTC CAG ATG TTC          630

ATA GAC GCC CTT TAT GAG GAG CAG TAT GAA AGG GAT GTG GCC          672

TGG ATA GCC AGG CAA AGC AAG CGC ATG TCC TCT GTC GAT GAG          714

GAT GAA GAC GAT GAG GAT GAT GAG GAT GAC TAC TAC GAC GAC          756

GAG GAC GAC GAC GAC GAT GCC TTC TAT GAT GAT GAG GAT GAT          798

GAG GAA GAA GAA TTG GAG AAC CTG ATG GAT GAT GAA TCA GAA          840

GAT GAG GCC GAA GAA GAG ATG AGC GTG GAA ATG GGT GCC GGA          882

GCT GAG GAA ATG GGT GCT GGC GCT AAC TGT GCC TGT GTT CCT          924

GGC CAT CAT TTA AGG AAG AAT GAA GTG AAG TGT AGG ATG ATT          966

TAT TTC TTC CAC GAC CCT AAT TTC CTG GTG TCT ATA CCA GTG         1008

AAC CCT AAG GAA CAA ATG GAG TGT AGG TGT GAA AAT GCT GAT         1050

GAA GAG GTT GCA ATG GAA GAG GAA GAA GAA GAA GAG GAG GAG         1092

GAG GAG GAA GAG GAA ATG GGA AAC CCG GAT GGC TTC TCA CCT         1134

TAG                                                             1137

GCATGCAGTT GCAAAGCCCA GAAGAAAGAA ATGGACAGCG GAAGAAGTGG          1187

TTGTTTTTTT TTCCCCTTCA TTAATTTTCT AGTTTTTAGT AATCCAGAAA          1237

ATTTGATTTT GTTCTAAAGT TCATTATGCA AAGATGTCAC CAACAGACTT          1287

CTGACTGCAT GGTGAACTTT CATATGATAC ATAGGATTAC ACTTGTACCT          1337

GTTAAAAATA AAAGTTTGAC TTGCATAC                                  1365
```

(2) INFORMATION FOR SEQ ID NO: 5:

(i) SEQUENCE CHARACTERISTICS:
(A) LENGTH: 4698 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 5:

```
ACCACAGGAG AATGAAAAGA ACCCGGGACT CCCAAAGACG CTAGATGTGT            50

GAAGATCCTG ATCACTCATT GGGTGTCTGA GTTCTGCGAT ATTCATCCCT           100

CAGCCAATGA GCTTACTGTT CTCGTGGGGG GTTTGTGAGC CTTGGGTAGG           150

AAGTTTTGCA AGTTCCGCCT ACAGCTCTAG CTTGTGAATT TGTACCCTTT           200

CACGTAAAAA AGTAGTCCAG AGTTTACTAC ACCCTCCCTC CCCCCTCCCA           250

CCTCGTGCTG TGCTGAGTTT AGAAGTCTTC CTTATAGAAG TCTTCCGTAT           300

AGAACTCTTC CGGAGGAAGG AGGGAGGACC CCCCCCCTTT GCTCTCCCAG           350

CATGCATTGT GTCAACGCCA TTGCACTGAG CTGGTCGAAG AAGTAAGCCG           400

CTAGCTTGCG ACTCTACTCT TATCTTAACT TAGCTCGGCT TCCTGCTGGT           450

ACCCTTTGTG CC                                                    462
```

-continued

```
ATG TCT GAT AAC AAG AAA CCA GAC AAA GCC CAC AGT GGC TCA          504
GGT GGT GAC GGT GAT GGG AAT AGG TGC AAT TTA TTG CAC CGG          546
TAC TCC CTG GAA GAA ATT CTG CCT TAT CTA GGG TGG CTG GTC          588
TTC GCT GTT GTC ACA ACA AGT TTT CTG GCG CTC CAG ATG TTC          630
ATA GAC GCC CTT TAT GAG GAG CAG TAT GAA AGG GAT GTG GCC          672
TGG ATA GCC AGG CAA AGC AAG CGC ATG TCC TCT GTC GAT GAG          714
GAT GAA GAC GAT GAG GAT GAT GAG GAT GAC TAC TAC GAC GAC          756
GAG GAC GAC GAC GAC GAT GCC TTC TAT GAT GAT GAG GAT GAT          798
GAG GAA GAA GAA TTG GAG AAC CTG ATG GAT GAT GAA TCA GAA          840
GAT GAG GCC GAA GAA GAG ATG AGC GTG GAA ATG GGT GCC GGA          882
GCT GAG GAA ATG GGT GCT GGC GCT AAC TGT GCC T                    916
GTGAGTAACC CGTGGTCTTT ACTCTAGATT CAGGTGGGGT GCATTCTTTA           966
CTCTTGCCCA CATCTGTAGT AAAGACCACA TTTTGGTTGG GGGTCATTGC          1016
TGGAGCCATT CCTGGCTCTC CTGTCCACGC CTATCCCCGC TCCTCCCATC          1066
CCCCACTCCT TGCTCCGCTC TCTTTCCTTT TCCCACCTTG CCTCTGGAGC          1116
TTCAGTCCAT CCTGCTCTGC TCCCTTTCCC CTTTGCTCTC CTTGCTCCCC          1166
TCCCCCTCGG CTCAACTTTT CGTGCCTTCT GCTCTCTGAT CCCCACCCTC          1216
TTCAGGCTTC CCCATTTGCT CCTCTCCCGA AACCCTCCCC TTCCTGTTCC          1266
CCTTTTCGCG CCTTTTCTTT CCTGCTCCCC TCCCCCTCCC TATTTACCTT          1316
TCACCAGCTT TGCTCTCCCT GCTCCCCTCC CCCTTTTGCA CCTTTTCTTT          1366
TCCTGCTCCC CTCCCCCTCC CCTCCCTGTT TACCCTTCAC CGCTTTTCCT          1416
CTACCTGCTT CCCTCCCCCT TGCTGCTCCC TCCCTATTTG CATTTTCGGG          1466
TGCTCCTCCC TCCCCCTCCC CCTCCCTCCC TATTTGCATT TTCGGGTGCT          1516
CCTCCCTCCC CCTCCCCAGG CCTTTTTTTT TTTTTTTTTT TTTTTTTTTT          1566
TTGGTTTTTC GAGACAGGGT TTCTCTTTGT ATCCCTGGCT GTCCTGGCAC          1616
TCACTCTGTA GACCAGGCTG GCCTCAAACT CAGAAATCTG CCTGCCTCTG          1666
CCTCCCAAAT GCTGGGATTA AAGGCTTGCA CCAGGACTGC CCCAGTGCAG          1716
GCCTTTCTTT TTTCTCCTCT CTGGTCTCCC TAATCCCTTT TCTGCATGTT          1766
AACTCCCCTT TTGGCACCTT TCCTTTACAG GACCCCCTCC CCCTCCCTGT          1816
TTCCCTTCCG GCACCCTTCC TAGCCCTGCT CTGTTCCCTC TCCCTGCTCC          1866
CCTCCCCCTC TTTGCTCGAC TTTTAGCAGC CTTACCTCTC CCTGCTTTCT          1916
GCCCCGTTCC CCTTTTTTGT GCCTTTCCTC CTGGCTCCCC TCCACCTTCC          1966
AGCTCACCTT TTTGTTTGTT TGGTTGTTTG GTTGTTTGGT TTGCTTTTTT          2016
TTTTTTTTTT GCACCTTGTT TTCCAAGATC CCCCTCCCCC TCCGGCTTCC          2066
CCTCTGTGTG CCTTTCCTGT TCCCTCCCCC TCGCTGGCTC CCCCTCCCTT          2116
TCTGCCTTTC CTGTCCCTGC TCCCTTCTCT GCTAACCTTT TAATGCCTTT          2166
CTTTTCTAGA CTCCCCCCTC CAGGCTTGCT GTTTGCTTCT GTGCACTTTT          2216
CCTGACCCTG CTCCCCTTCC CCTCCCAGCT CCCCCCTCTT TTCCCACCTC          2266
CCTTTCTCCA GCCTGTCACC CCTCCTTCTC TCCTCTCTGT TTCTCCCACT          2316
```

-continued

```
TCCTGCTTCC TTTACCCCTT CCCTCTCCCT ACTCTCCTCC CTGCCTGCTG    2366
GACTTCCTCT CCAGCCGCCC AGTTCCCTGC AGTCCTGGAG TCTTTCCTGC    2416
CTCTCTGTCC ATCACTTCCC CCTAGTTTCA CTTCCCTTTC ACTCTCCCCT    2466
ATGTGTCTCT CTTCCTATCT ATCCCTTCCT TTCTGTCCCC TCTCCTCTGT    2516
CCATCACCTC TCTCCTCCCT TCCCTTTCCT CTCTCTTCCA TTTTCTTCCA    2566
CCTGCTTCTT TACCCTGCCT CTCCCATTGC CCTCTTACCT TTATGCCCAT    2616
TCCATGTCCC CTCTCAATTC CCTGTCCCAT TGTGCTCCCT CACATCTTCC    2666
ATTTCCCTCT TTCTCCCTTA GCCTCTTCTT CCTCTTCTCT TGTATCTCCC    2716
TTCCCTTTGC TTCTCCCTCC TCCTTTCCCC TTCCCCTATG CCCTCTACTC    2766
TACTTGATCT TCTCTCCTCT CCACATACCC TTTTTCCTTT CCACCCTGCC    2816
CTTTGTCCCC AGACCCTACA GTATCCTGTG CACAGGAAGT GGGAGGTGCC    2866
ATCAACAACA AGGAGGCAAG AAACAGAGCA AAATCCCAAA ATCAGCAGGA    2916
AAGGCTGGAT GAAAATAAGG CCAGGTTCTG AGGACAGCTG GAATCTAGCC    2966
AAGTGGCTCC TATAACCCTA AGTACCAAGG GAGAAAGTGA TGGTGAAGTT    3016
CTTGATCCTT GCTGCTTCTT TTACATATGT TGGCACATCT TTCTCAAATG    3066
CAGGCCATGC TCCATGCTTG GCGCTTGCTC AGCGTGGTTA AGTAATGGGA    3116
GAATCTGAAA ACTAGGGGCC AGTGGTTTGT TTTGGGGACA AATTAGCACG    3166
TAGTGATATT TCCCCCTAAA AATTATAACA AACAGATTCA TGATTTGAGA    3216
TCCTTCTACA GGTGAGAAGT GGAAAAATTG TCACTATGAA GTTCTTTTTA    3266
GGCTAAAGAT ACTTGGAACC ATAGAAGCGT TGTTAAAATA CTGCTTTCTT    3316
TTGCTAAAAT ATTCTTTCTC ACATATTCAT ATTCTCCAG                3355
GT GTT CCT GGC CAT CAT TTA AGG AAG AAT GAA GTG AAG TGT    3396
AGG ATG ATT TAT TTC TTC CAC GAC CCT AAT TTC CTG GTG TCT   3438
ATA CCA GTG AAC CCT AAG GAA CAA ATG GAG TGT AGG TGT GAA   3480
AAT GCT GAT GAA GAG GTT GCA ATG GAA GAG GAA GAA GAA GAA   3522
GAG GAG GAG GAG GAG GAA GAG GAA ATG GGA AAC CCG GAT GGC   3564
TTC TCA CCT TAG                                           3576
GCATGCAGGT ACTGGCTTCA CTAACCAACC ATTCCTAACA TATGCCTGTA    3626
GCTAAGAGCA TCTTTTTAAA AAATATTATT GGTAAACTAA ACAATTGTTA    3676
TCTTTTTACA TTAATAAGTA TTAAATTAAT CCAGTATACA GTTTTAAGAA    3726
CCCTAAGTTA AACAGAAGTC AATGATGTCT AGATGCCTGT TCTTTAGATT    3776
GTAGTGAGAC TACTTACTAC AGATGAGAAG TTGTTAGACT CGGGAGTAGA    3826
GACCAGTAAA AGATCATGCA GTGAAATGTG GCCATGGAAA TCGCATATTG    3876
TTCTTATAGT ACCTTTGAGA CAGCTGATAA CAGCTGACAA AAATAAGTGT    3926
TTCAAGAAAG ATCACACGCC ATGGTTCACA TGCAAATTAT TATTTTGTCG    3976
TTCTGATTTT TTTCATTTCT AGACCTGTGG TTTTAAAGAG ATGAAAATCT    4026
CTTAAAATTT CCTTCATCTT TAATTTTCCT TAACTTTAGT TTTTTTCACT    4076
TAGAATTCAA TTCAAATTCT TAATTCAATC TTAATTTTTA GATTTCTTAA    4126
AATGTTTTTT AAAAAAAATG CAAATCTCAT TTTTAAGAGA TGAAAGCAGA    4176
GTAACTGGGG GGCTTAGGGA ATCTGTAGGG TTGCGGTATA GCAATAGGGA    4226
```

-continued

```
GTTCTGGTCT CTGAGAAGCA GTCAGAGAGA ATGGAAAACC AGGCCCTTGC          4276

CAGTAGGTTA GTGAGGTTGA TATGATCAGA TTATGGACAC TCTCCAAATC          4326

ATAAATACTC TAACAGCTAA GGATCTCTGA GGGAAACACA ACAGGGAAAT          4376

ATTTTAGTTT CTCCTTGAGA AACAATGACA AGACATAAAA TTGGCAAGAA          4426

AGTCAGGAGT GTATTCTAAT AAGTGTTGCT TATCTCTTAT TTTCTTCTAC          4476

AGTTGCAAAG CCCAGAAGAA AGAAATGGAC AGCGGAAGAA GTGGTTGTTT          4526

TTTTTTCCCC TTCATTAATT TTCTAGTTTT TAGTAATCCA GAAAATTTGA          4576

TTTTGTTCTA AAGTTCATTA TGCAAAGATG TCACCAACAG ACTTCTGACT          4626

GCATGGTGAA CTTTCATATG ATACATAGGA TTACACTTGT ACCTGTTAAA          4676

AATAAAAGTT TGACTTGCAT AC                                        4698
```

(2) INFORMATION FOR SEQ ID NO: 6:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 6:

```
Leu Pro Tyr Leu Gly Trp Leu
                5
```

(2) INFORMATION FOR SEQ ID NO: 7:

(i) SEQUENCE CHARACTERISTICS:
(A) LENGTH: 2420 base pairs
(B) TYPE: nucleic acid
(C) STRANDEDNESS: single
(D) TOPOLOGY: linear (ii) MOLECULE TYPE: genomic DNA (xi) SEQUENCE DESCRIPTION: SEQ ID NO: 7:

```
GGATCCAGGC CCTGCCAGGA AAAATATAAG GGCCCTGCGT GAGAACAGAG            50

GGGGTCATCC ACTGCATGAG AGTGGGGATG TCACAGAGTC CAGCCCACCC           100

TCCTGGTAGC ACTGAGAAGC CAGGGCTGTG CTTGCGGTCT GCACCCTGAG           150

GGCCCGTGGA TTCCTCTTCC TGGAGCTCCA GGAACCAGGC AGTGAGGCCT           200

TGGTCTGAGA CAGTATCCTC AGGTCACAGA GCAGAGGATG CACAGGGTGT           250

GCCAGCAGTG AATGTTTGCC CTGAATGCAC ACCAAGGGCC CCACCTGCCA           300

CAGGACACAT AGGACTCCAC AGAGTCTGGC CTCACCTCCC TACTGTCAGT           350

CCTGTAGAAT CGACCTCTGC TGGCCGGCTG TACCCTGAGT ACCCTCTCAC           400

TTCCTCCTTC AGGTTTTCAG GGGACAGGCC AACCCAGAGG ACAGGATTCC           450

CTGGAGGCCA CAGAGGAGCA CCAAGGAGAA GATCTGTAAG TAGGCCTTTG           500

TTAGAGTCTC CAAGGTTCAG TTCTCAGCTG AGGCCTCTCA CACACTCCCT           550

CTCTCCCCAG GCCTGTGGGT CTTCATTGCC CAGCTCCTGC CCACACTCCT           600

GCCTGCTGCC CTGACGAGAG TCATCATGTC TCTTGAGCAG AGGAGTCTGC           650

ACTGCAAGCC TGAGGAAGCC CTTGAGGCCC AACAAGAGGC CCTGGGCCTG           700

GTGTGTGTGC AGGCTGCCAC CTCCTCCTCC TCTCCTCTGG TCCTGGGCAC           750
```

-continued

```
CCTGGAGGAG GTGCCCACTG CTGGGTCAAC AGATCCTCCC CAGAGTCCTC    800
AGGGAGCCTC CGCCTTTCCC ACTACCATCA ACTTCACTCG ACAGAGGCAA    850
CCCAGTGAGG GTTCCAGCAG CCGTGAAGAG GAGGGGCCAA GCACCTCTTG    900
TATCCTGGAG TCCTTGTTCC GAGCAGTAAT CACTAAGAAG GTGGCTGATT    950
TGGTTGGTTT TCTGCTCCTC AAATATCGAG CCAGGGAGCC AGTCACAAAG   1000
GCAGAAATGC TGGAGAGTGT CATCAAAAAT TACAAGCACT GTTTTCCTGA   1050
GATCTTCGGC AAAGCCTCTG AGTCCTTGCA GCTGGTCTTT GGCATTGACG   1100
TGAAGGAAGC AGACCCCACC GGCCACTCCT ATGTCCTTGT CACCTGCCTA   1150
GGTCTCTCCT ATGATGGCCT GCTGGGTGAT AATCAGATCA TGCCCAAGAC   1200
AGGCTTCCTG ATAATTGTCC TGGTCATGAT TGCAATGGAG GGCGGCCATG   1250
CTCCTGAGGA GGAAATCTGG GAGGAGCTGA GTGTGATGGA GGTGTATGAT   1300
GGGAGGGAGC ACAGTGCCTA TGGGGAGCCC AGGAAGCTGC TCACCCAAGA   1350
TTTGGTGCAG GAAAAGTACC TGGAGTACCG GCAGGTGCCG GACAGTGATC   1400
CCGCACGCTA TGAGTTCCTG TGGGGTCCAA GGGCCCTCGC TGAAACCAGC   1450
TATGTGAAAG TCCTTGAGTA TGTGATCAAG GTCAGTGCAA GAGTTCGCTT   1500
TTTCTTCCCA TCCCTGCGTG AAGCAGCTTT GAGAGAGGAG GAAGAGGGAG   1550
TCTGAGCATG AGTTGCAGCC AAGGCCAGTG GGAGGGGGAC TGGGCCAGTG   1600
CACCTTCCAG GGCCGCGTCC AGCAGCTTCC CCTGCCTCGT GTGACATGAG   1650
GCCCATTCTT CACTCTGAAG AGAGCGGTCA GTGTTCTCAG TAGTAGGTTT   1700
CTGTTCTATT GGGTGACTTG GAGATTTATC TTTGTTCTCT TTTGGAATTG   1750
TTCAAATGTT TTTTTTTAAG GGATGGTTGA ATGAACTTCA GCATCCAAGT   1800
TTATGAATGA CAGCAGTCAC ACAGTTCTGT GTATATAGTT TAAGGGTAAG   1850
AGTCTTGTGT TTTATTCAGA TTGGGAAATC CATTCTATTT TGTGAATTGG   1900
GATAATAACA GCAGTGGAAT AAGTACTTAG AAATGTGAAA AATGAGCAGT   1950
AAAATAGATG AGATAAAGAA CTAAAGAAAT TAAGAGATAG TCAATTCTTG   2000
CCTTATACCT CAGTCTATTC TGTAAAATTT TTAAAGATAT ATGCATACCT   2050
GGATTTCCTT GGCTTCTTTG AGAATGTAAG AGAAATTAAA TCTGAATAAA   2100
GAATTCTTCC TGTTCACTGG CTCTTTTCTT CTCCATGCAC TGAGCATCTG   2150
CTTTTTGGAA GGCCCTGGGT TAGTAGTGGA GATGCTAAGG TAAGCCAGAC   2200
TCATACCCAC CCATAGGGTC GTAGAGTCTA GGAGCTGCAG TCACGTAATC   2250
GAGGTGGCAA GATGTCCTCT AAAGATGTAG GGAAAAGTGA GAGAGGGGTG   2300
AGGGTGTGGG GCTCCGGGTG AGAGTGGTGG AGTGTCAATG CCCTGAGCTG   2350
GGGCATTTTG GGCTTTGGGA AACTGCAGTT CCTTCTGGGG GAGCTGATTG   2400
TAATGATCTT GGGTGGATCC                                    2420
```

(2) INFORMATION FOR SEQ ID NO: 8:

(i) SEQUENCE CHARACTERISTICS:
(A) LENGTH: 5675 base pairs
(B) TYPE: nucleic acid
(C) STRANDEDNESS: single
(D) TOPOLOGY: linear (ii) MOLECULE TYPE: genomic DNA -continued (ix) FEATURE:
(A) NAME/KEY:MAGE-1 gene (xi) SEQUENCE DESCRIPTION: SEQ ID NO: 8:

```
CCCGGGGCAC CACTGGCATC CCTCCCCCTA CCACCCCCAA TCCCTCCCTT    50
TACGCCACCC ATCCAAACAT CTTCACGCTC ACCCCCAGCC CAAGCCAGGC   100
AGAATCCGGT TCCACCCCTG CTCTCAACCC AGGGAAGCCC AGGTGCCCAG   150
ATGTGACGCC ACTGACTTGA GCATTAGTGG TTAGAGAGAA GCGAGGTTTT   200
CGGTCTGAGG GGCGGCTTGA GATCGGTGGA GGGAAGCGGG CCCAGCTCTG   250
TAAGGAGGCA AGGTGACATG CTGAGGGAGG ACTGAGGACC CACTTACCCC   300
AGATAGAGGA CCCCAAATAA TCCCTTCATG CCAGTCCTGG ACCATCTGGT   350
GGTGGACTTC TCAGGCTGGG CCACCCCCAG CCCCCTTGCT GCTTAAACCA   400
CTGGGGACTC GAAGTCAGAG CTCCGTGTGA TCAGGGAAGG GCTGCTTAGG   450
AGAGGGCAGC GTCCAGGCTC TGCCAGACAT CATGCTCAGG ATTCTCAAGG   500
AGGGCTGAGG GTCCCTAAGA CCCCACTCCC GTGACCCAAC CCCCACTCCA   550
ATGCTCACTC CCGTGACCCA ACCCCCTCTT CATTGTCATT CCAACCCCCA   600
CCCCACATCC CCCACCCCAT CCCTCAACCC TGATGCCCAT CCGCCCAGCC   650
ATTCCACCCT CACCCCCACC CCCACCCCCA CGCCCACTCC CACCCCCACC   700
CAGGCAGGAT CCGGTTCCCG CCAGGAAACA TCCGGGTGCC CGGATGTGAC   750
GCCACTGACT TGCGCATTGT GGGGCAGAGA GAAGCGAGGT TTCCATTCTG   800
AGGGACGGCG TAGAGTTCGG CCGAAGGAAC CTGACCCAGG CTCTGTGAGG   850
AGGCAAGGTG AGAGGCTGAG GGAGGACTGA GGACCCCGCC ACTCCAAATA   900
GAGAGCCCCA AATATTCCAG CCCCGCCCTT GCTGCCAGCC CTGGCCCACC   950
CGCGGGAAGA CGTCTCAGCC TGGGCTGCCC CCAGACCCCT GCTCCAAAAG  1000
CCTTGAGAGA CACCAGGTTC TTCTCCCCAA GCTCTGGAAT CAGAGGTTGC  1050
TGTGACCAGG GCAGGACTGG TTAGGAGAGG GCAGGGCACA GGCTCTGCCA  1100
GGCATCAAGA TCAGCACCCA AGAGGGAGGG CTGTGGGCCC CCAAGACTGC  1150
ACTCCAATCC CCACTCCCAC CCCATTCGCA TTCCCATTCC CCACCCAACC  1200
CCCATCTCCT CAGCTACACC TCCACCCCCA TCCCTACTCC TACTCCGTCA  1250
CCTGACCACC ACCCTCCAGC CCCAGCACCA GCCCCAACCC TTCTGCCACC  1300
TCACCCTCAC TGCCCCCAAC CCCACCCTCA TCTCTCTCAT GTGCCCCACT  1350
CCCATCGCCT CCCCCATTCT GGCAGAATCC GGTTTGCCCC TGCTCTCAAC  1400
CCAGGGAAGC CCTGGTAGGC CCGATGTGAA ACCACTGACT TGAACCTCAC  1450
AGATCTGAGA GAAGCCAGGT TCATTTAATG GTTCTGAGGG GCGGCTTGAG  1500
ATCCACTGAG GGGAGTGGTT TTAGGCTCTG TGAGGAGGCA AGGTGAGATG  1550
CTGAGGGAGG ACTGAGGAGG CACACACCCC AGGTAGATGG CCCCAAAATG  1600
ATCCAGTACC ACCCCTGCTG CCAGCCCTGG ACCACCCGGC CAGGACAGAT  1650
GTCTCAGCTG GACCACCCCC CGTCCCGTCC CACTGCCACT TAACCCACAG  1700
GGCAATCTGT AGTCATAGCT TATGTGACCG GGGCAGGGTT GGTCAGGAGA  1750
GGCAGGGCCC AGGCATCAAG GTCCAGCATC CGCCCGGCAT TAGGGTCAGG  1800
ACCCTGGGAG GGAACTGAGG GTTCCCCACC CACACCTGTC TCCTCATCTC  1850
```

-continued

```
CACCGCCACC CCACTCACAT TCCCATACCT ACCCCCTACC CCCAACCTCA    1900
TCTTGTCAGA ATCCCTGCTG TCAACCCACG GAAGCCACGG GAATGGCGGC    1950
CAGGCACTCG GATCTTGACG TCCCCATCCA GGGTCTGATG GAGGGAAGGG    2000
GCTTGAACAG GGCCTCAGGG GAGCAGAGGG AGGGCCCTAC TGCGAGATGA    2050
GGGAGGCCTC AGAGGACCCA GCACCCTAGG ACACCGCACC CCTGTCTGAG    2100
ACTGAGGCTG CCACTTCTGG CCTCAAGAAT CAGAACGATG GGGACTCAGA    2150
TTGCATGGGG GTGGGACCCA GGCCTGCAAG GCTTACGCGG AGGAAGAGGA    2200
GGGAGGACTC AGGGGACCTT GGAATCCAGA TCAGTGTGGA CCTCGGCCCT    2250
GAGAGGTCCA GGGCACGGTG GCCACATATG GCCCATATTT CCTGCATCTT    2300
TGAGGTGACA GGACAGAGCT GTGGTCTGAG AAGTGGGGCC TCAGGTCAAC    2350
AGAGGGAGGA GTTCCAGGAT CCATATGGCC CAAGATGTGC CCCCTTCATG    2400
AGGACTGGGG ATATCCCCGG CTCAGAAAGA AGGGACTCCA CACAGTCTGG    2450
CTGTCCCCTT TTAGTAGCTC TAGGGGGACC AGATCAGGGA TGGCGGTATG    2500
TTCCATTCTC ACTTGTACCA CAGGCAGGAA GTTGGGGGGC CCTCAGGGAG    2550
ATGGGGTCTT GGGGTAAAGG GGGGATGTCT ACTCATGTCA GGGAATTGGG    2600
GGTTGAGGAA GCACAGGCGC TGGCAGGAAT AAAGATGAGT GAGACAGACA    2650
AGGCTATTGG AATCCACACC CCAGAACCAA AGGGGTCAGC CCTGGACACC    2700
TCACCCAGGA TGTGGCTTCT TTTTCACTCC TGTTTCCAGA TCTGGGGCAG    2750
GTGAGGACCT CATTCTCAGA GGGTGACTCA GGTCAACGTA GGGACCCCCA    2800
TCTGGTCTAA AGACAGAGCG GTCCCAGGAT CTGCCATGCG TTCGGGTGAG    2850
GAACATGAGG GAGGACTGAG GGTACCCCAG GACCAGAACA CTGAGGGAGA    2900
CTGCACAGAA ATCAGCCCTG CCCCTGCTGT CACCCCAGAG AGCATGGGCT    2950
GGGCCGTCTG CCGAGGTCCT TCCGTTATCC TGGGATCATT GATGTCAGGG    3000
ACGGGGAGGC CTTGGTCTGA GAAGGCTGCG CTCAGGTCAG TAGAGGGAGC    3050
GTCCCAGGCC CTGCCAGGAG TCAAGGTGAG GACCAAGCGG GCACCTCACC    3100
CAGGACACAT TAATTCCAAT GAATTTTGAT ATCTCTTGCT GCCCTTCCCC    3150
AAGGACCTAG GCACGTGTGG CCAGATGTTT GTCCCCTCCT GTCCTTCCAT    3200
TCCTTATCAT GGATGTGAAC TCTTGATTTG GATTTCTCAG ACCAGCAAAA    3250
GGGCAGGATC CAGGCCCTGC CAGGAAAAAT ATAAGGGCCC TGCGTGAGAA    3300
CAGAGGGGGT CATCCACTGC ATGAGAGTGG GGATGTCACA GAGTCCAGCC    3350
CACCCTCCTG GTAGCACTGA GAAGCCAGGG CTGTGCTTGC GGTCTGCACC    3400
CTGAGGGCCC GTGGATTCCT CTTCCTGGAG CTCCAGGAAC CAGGCAGTGA    3450
GGCCTTGGTC TGAGACAGTA TCCTCAGGTC ACAGAGCAGA GGATGCACAG    3500
GGTGTGCCAG CAGTGAATGT TTGCCCTGAA TGCACACCAA GGGCCCCACC    3550
TGCCACAGGA CACATAGGAC TCCACAGAGT CTGGCCTCAC CTCCCTACTG    3600
TCAGTCCTGT AGAATCGACC TCTGCTGGCC GGCTGTACCC TGAGTACCCT    3650
CTCACTTCCT CCTTCAGGTT TTCAGGGGAC AGGCCAACCC AGAGGACAGG    3700
ATTCCCTGGA GGCCACAGAG GAGCACCAAG GAGAAGATCT GTAAGTAGGC    3750
CTTTGTTAGA GTCTCCAAGG TTCAGTTCTC AGCTGAGGCC TCTCACACAC    3800
```

-continued

```
TCCCTCTCTC CCCAGGCCTG TGGGTCTTCA TTGCCCAGCT CCTGCCCACA      3850
CTCCTGCCTG CTGCCCTGAC GAGAGTCATC                            3880
ATG TCT CTT GAG CAG AGG AGT CTG CAC TGC AAG CCT GAG GAA     3922
GCC CTT GAG GCC CAA CAA GAG GCC CTG GGC CTG GTG TGT GTG     3964
CAG GCT GCC ACC TCC TCC TCC TCT CCT CTG GTC CTG GGC ACC     4006
CTG GAG GAG GTG CCC ACT GCT GGG TCA ACA GAT CCT CCC CAG     4048
AGT CCT CAG GGA GCC TCC GCC TTT CCC ACT ACC ATC AAC TTC     4090
ACT CGA CAG AGG CAA CCC AGT GAG GGT TCC AGC AGC CGT GAA     4132
GAG GAG GGG CCA AGC ACC TCT TGT ATC CTG GAG TCC TTG TTC     4174
CGA GCA GTA ATC ACT AAG AAG GTG GCT GAT TTG GTT GGT TTT     4216
CTG CTC CTC AAA TAT CGA GCC AGG GAG CCA GTC ACA AAG GCA     4258
GAA ATG CTG GAG AGT GTC ATC AAA AAT TAC AAG CAC TGT TTT     4300
CCT GAG ATC TTC GGC AAA GCC TCT GAG TCC TTG CAG CTG GTC     4342
TTT GGC ATT GAC GTG AAG GAA GCA GAC CCC ACC GGC CAC TCC     4384
TAT GTC CTT GTC ACC TGC CTA GGT CTC TCC TAT GAT GGC CTG     4426
CTG GGT GAT AAT CAG ATC ATG CCC AAG ACA GGC TTC CTG ATA     4468
ATT GTC CTG GTC ATG ATT GCA ATG GAG GGC GGC CAT GCT CCT     4510
GAG GAG GAA ATC TGG GAG GAG CTG AGT GTG ATG GAG GTG TAT     4552
GAT GGG AGG GAG CAC AGT GCC TAT GGG GAG CCC AGG AAG CTG     4594
CTC ACC CAA GAT TTG GTG CAG GAA AAG TAC CTG GAG TAC CGG     4636
CAG GTG CCG GAC AGT GAT CCC GCA CGC TAT GAG TTC CTG TGG     4678
GGT CCA AGG GCC CTC GCT GAA ACC AGC TAT GTG AAA GTC CTT     4720
GAG TAT GTG ATC AAG GTC AGT GCA AGA GTT CGC TTT TTC TTC     4762
CCA TCC CTG CGT GAA GCA GCT TTG AGA GAG GAG GAA GAG GGA     4804
GTC TGA                                                     4810
GCATGAGTTG CAGCCAAGGC CAGTGGGAGG GGGACTGGGC CAGTGCACCT      4860
TCCAGGGCCG CGTCCAGCAG CTTCCCCTGC CTCGTGTGAC ATGAGGCCCA      4910
TTCTTCACTC TGAAGAGAGC GGTCAGTGTT CTCAGTAGTA GGTTTCTGTT      4960
CTATTGGGTG ACTTGGAGAT TTATCTTTGT TCTCTTTTGG AATTGTTCAA      5010
ATGTTTTTTT TTAAGGGATG GTTGAATGAA CTTCAGCATC CAAGTTTATG      5060
AATGACAGCA GTCACACAGT TCTGTGTATA TAGTTTAAGG GTAAGAGTCT      5110
TGTGTTTTAT TCAGATTGGG AAATCCATTC TATTTTGTGA ATTGGGATAA      5160
TAACAGCAGT GGAATAAGTA CTTAGAAATG TGAAAAATGA GCAGTAAAAT      5210
AGATGAGATA AAGAACTAAA GAAATTAAGA GATAGTCAAT TCTTGCCTTA      5260
TACCTCAGTC TATTCTGTAA AATTTTTAAA GATATATGCA TACCTGGATT      5310
TCCTTGGCTT CTTTGAGAAT GTAAGAGAAA TTAAATCTGA ATAAAGAATT      5360
CTTCCTGTTC ACTGGCTCTT TTCTTCTCCA TGCACTGAGC ATCTGCTTTT      5410
TGGAAGGCCC TGGGTTAGTA GTGGAGATGC TAAGGTAAGC CAGACTCATA      5460
CCCACCCATA GGGTCGTAGA GTCTAGGAGC TGCAGTCACG TAATCGAGGT      5510
GGCAAGATGT CCTCTAAAGA TGTAGGGAAA AGTGAGAGAG GGGTGAGGGT      5560
```

-continued

```
GTGGGGCTCC GGGTGAGAGT GGTGGAGTGT CAATGCCCTG AGCTGGGGCA          5610

TTTTGGGCTT TGGGAAACTG CAGTTCCTTC TGGGGGAGCT GATTGTAATG          5660

ATCTTGGGTG GATCC                                                5675
```

(2) INFORMATION FOR SEQ ID NO: 9:

(i) SEQUENCE CHARACTERISTICS:
(A) LENGTH: 4157 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-2 gene (xi) SEQUENCE DESCRIPTION: SEQ ID NO: 9:

```
CCCATCCAGA TCCCCATCCG GGCAGAATCC GGTTCCACCC TTGCCGTGAA            50

CCCAGGGAAG TCACGGGCCC GGATGTGACG CCACTGACTT GCACATTGGA           100

GGTCAGAGGA CAGCGAGATT CTCGCCCTGA GCAACGGCCT GACGTCGGCG           150

GAGGGAAGCA GGCGCAGGCT CCGTGAGGAG GCAAGGTAAG ACGCCGAGGG           200

AGGACTGAGG CGGGCCTCAC CCCAGACAGA GGGCCCCCAA TTAATCCAGC           250

GCTGCCTCTG CTGCCGGGCC TGGACCACCC TGCAGGGGAA GACTTCTCAG           300

GCTCAGTCGC CACCACCTCA CCCCGCCACC CCCCGCCGCT TTAACCGCAG           350

GGAACTCTGG CGTAAGAGCT TTGTGTGACC AGGGCAGGGC TGGTTAGAAG           400

TGCTCAGGGC CCAGACTCAG CCAGGAATCA AGGTCAGGAC CCCAAGAGGG           450

GACTGAGGGC AACCCACCCC CTACCCTCAC TACCAATCCC ATCCCCCAAC           500

ACCAACCCCA CCCCCATCCC TCAAACACCA ACCCCACCCC CAAACCCCAT           550

TCCCATCTCC TCCCCCACCA CCATCCTGGC AGAATCCGGC TTTGCCCCTG           600

CAATCAACCC ACGGAAGCTC CGGGAATGGC GGCCAAGCAC GCGGATCCTG           650

ACGTTCACAT GTACGGCTAA GGGAGGGAAG GGGTTGGGTC TCGTGAGTAT           700

GGCCTTTGGG ATGCAGAGGA AGGGCCCAGG CCTCCTGGAA GACAGTGGAG           750

TCCTTAGGGG ACCCAGCATG CCAGGACAGG GGGCCCACTG TACCCCTGTC           800

TCAAACTGAG CCACCTTTTC ATTCAGCCGA GGGAATCCTA GGGATGCAGA           850

CCCACTTCAG GGGGTTGGGG CCCAGCCTGC GAGGAGTCAA GGGGAGGAAG           900

AAGAGGGAGG ACTGAGGGGA CCTTGGAGTC CAGATCAGTG GCAACCTTGG           950

GCTGGGGGAT CCTGGGCACA GTGGCCGAAT GTGCCCCGTG CTCATTGCAC          1000

CTTCAGGGTG ACAGAGAGTT GAGGGCTGTG GTCTGAGGGC TGGGACTTCA          1050

GGTCAGCAGA GGGAGGAATC CCAGGATCTG CCGGACCCAA GGTGTGCCCC          1100

CTTCATGAGG ACTCCCCATA CCCCCGGCCC AGAAAGAAGG GATGCCACAG          1150

AGTCTGGAAG TAAATTGTTC TTAGCTCTGG GGGAACCTGA TCAGGGATGG          1200

CCCTAAGTGA CAATCTCATT TGTACCACAG GCAGGAGGTT GGGGAACCCT          1250

CAGGGAGATA AGGTGTTGGT GTAAAGAGGA GCTGTCTGCT CATTTCAGGG          1300

GGTTCCCCCT TGAGAAAGGG CAGTCCCTGG CAGGAGTAAA GATGAGTAAC          1350

CCACAGGAGG CCATCATAAC GTTCACCCTA GAACCAAAGG GGTCAGCCCT          1400
```

-continued

```
GGACAACGCA CGTGGGGTAA CAGGATGTGG CCCCTCCTCA CTTGTCTTTC    1450
CAGATCTCAG GGAGTTGATG ACCTTGTTTT CAGAAGGTGA CTCAGTCAAC    1500
ACAGGGGCCC CTCTGGTCGA CAGATGCAGT GGTTCTAGGA TCTGCCAAGC    1550
ATCCAGGTGG AGAGCCTGAG GTAGGATTGA GGGTACCCCT GGGCCAGAAT    1600
GCAGCAAGGG GGCCCCATAG AAATCTGCCC TGCCCCTGCG GTTACTTCAG    1650
AGACCCTGGG CAGGGCTGTC AGCTGAAGTC CCTCCATTAT CTGGGATCTT    1700
TGATGTCAGG GAAGGGGAGG CCTTGGTCTG AAGGGGCTGG AGTCAGGTCA    1750
GTAGAGGGAG GGTCTCAGGC CCTGCCAGGA GTGGACGTGA GGACCAAGCG    1800
GACTCGTCAC CCAGGACACC TGGACTCCAA TGAATTTGAC ATCTCTCGTT    1850
GTCCTTCGCG GAGGACCTGG TCACGTATGG CCAGATGTGG GTCCCCTCTA    1900
TCTCCTTCTG TACCATATCA GGGATGTGAG TTCTTGACAT GAGAGATTCT    1950
CAAGCCAGCA AAAGGGTGGG ATTAGGCCCT ACAAGGAGAA AGGTGAGGGC    2000
CCTGAGTGAG CACAGAGGGG ACCCTCCACC CAAGTAGAGT GGGGACCTCA    2050
CGGAGTCTGG CCAACCCTGC TGAGACTTCT GGGAATCCGT GGCTGTGCTT    2100
GCAGTCTGCA CACTGAAGGC CCGTGCATTC CTCTCCCAGG AATCAGGAGC    2150
TCCAGGAACC AGGCAGTGAG GCCTTGGTCT GAGTCAGTGC CTCAGGTCAC    2200
AGAGCAGAGG GGACGCAGAC AGTGCCAACA CTGAAGGTTT GCCTGGAATG    2250
CACACCAAGG GCCCCACCCG CCCAGAACAA ATGGGACTCC AGAGGGCCTG    2300
GCCTCACCCT CCCTATTCTC AGTCCTGCAG CCTGAGCATG TGCTGGCCGG    2350
CTGTACCCTG AGGTGCCCTC CCACTTCCTC CTTCAGGTTC TGAGGGGGAC    2400
AGGCTGACAA GTAGGACCCG AGGCACTGGA GGAGCATTGA AGGAGAAGAT    2450
CTGTAAGTAA GCCTTTGTCA GAGCCTCCAA GGTTCAGTTC AGTTCTCACC    2500
TAAGGCCTCA CACACGCTCC TTCTCTCCCC AGGCCTGTGG GTCTTCATTG    2550
CCCAGCTCCT GCCCGCACTC CTGCCTGCTG CCCTGACCAG AGTCATC       2597
ATG CCT CTT GAG CAG AGG AGT CAG CAC TGC AAG CCT GAA GAA   2639
GGC CTT GAG GCC CGA GGA GAG GCC CTG GGC CTG GTG GGT GCG   2681
CAG GCT CCT GCT ACT GAG GAG CAG CAG ACC GCT TCT TCC TCT   2723
TCT ACT CTA GTG GAA GTT ACC CTG GGG GAG GTG CCT GCT GCC   2765
GAC TCA CCG AGT CCT CCC CAC AGT CCT CAG GGA GCC TCC AGC   2807
TTC TCG ACT ACC ATC AAC TAC ACT CTT TGG AGA CAA TCC GAT   2849
GAG GGC TCC AGC AAC CAA GAA GAG GAG GGG CCA AGA ATG TTT   2891
CCC GAC CTG GAG TCC GAG TTC CAA GCA GCA ATC AGT AGG AAG   2933
ATG GTT GAG TTG GTT CAT TTT CTG CTC CTC AAG TAT CGA GCC   2975
AGG GAG CCG GTC ACA AAG GCA GAA ATG CTG GAG AGT GTC CTC   3017
AGA AAT TGC CAG GAC TTC TTT CCC GTG ATC TTC AGC AAA GCC   3059
TCC GAG TAC TTG CAG CTG GTC TTT GGC ATC GAG GTG GTG GAA   3101
GTG GTC CCC ATC AGC CAC TTG TAC ATC CTT GTC ACC TGC CTG   3143
GGC CTC TCC TAC GAT GGC CTG CTG GGC GAC AAT CAG GTC ATG   3185
CCC AAG ACA GGC CTC CTG ATA ATC GTC CTG GCC ATA ATC GCA   3227
ATA GAG GGC GAC TGT GCC CCT GAG GAG AAA ATC TGG GAG GAG   3269
```

-continued

```
CTG AGT ATG TTG GAG GTG TTT GAG GGG AGG GAG GAC AGT GTC          3311

TTC GCA CAT CCC AGG AAG CTG CTC ATG CAA GAT CTG GTG CAG          3353

GAA AAC TAC CTG GAG TAC CGG CAG GTG CCC GGC AGT GAT CCT          3395

GCA TGC TAC GAG TTC CTG TGG GGT CCA AGG GCC CTC ATT GAA          3437

ACC AGC TAT GTG AAA GTC CTG CAC CAT ACA CTA AAG ATC GGT          3479

GGA GAA CCT CAC ATT TCC TAC CCA CCC CTG CAT GAA CGG GCT          3521

TTG AGA GAG GGA GAA GAG TGA                                      3542

GTCTCAGCAC ATGTTGCAGC CAGGGCCAGT GGGAGGGGGT CTGGGCCAGT           3592

GCACCTTCCA GGGCCCCATC CATTAGCTTC CACTGCCTCG TGTGATATGA           3642

GGCCCATTCC TGCCTCTTTG AAGAGAGCAG TCAGCATTCT TAGCAGTGAG           3692

TTTCTGTTCT GTTGGATGAC TTTGAGATTT ATCTTTCTTT CCTGTTGGAA           3742

TTGTTCAAAT GTTCCTTTTA ACAAATGGTT GGATGAACTT CAGCATCCAA           3792

GTTTATGAAT GACAGTAGTC ACACATAGTG CTGTTTATAT AGTTTAGGGG           3842

TAAGAGTCCT GTTTTTTATT CAGATTGGGA AATCCATTCC ATTTTGTGAG           3892

TTGTCACATA ATAACAGCAG TGGAATATGT ATTTGCCTAT ATTGTGAACG           3942

AATTAGCAGT AAAATACATG ATACAAGGAA CTCAAAAGAT AGTTAATTCT           3992

TGCCTTATAC CTCAGTCTAT TATGTAAAAT TAAAAATATG TGTATGTTTT           4042

TGCTTCTTTG AGAATGCAAA AGAAATTAAA TCTGAATAAA TTCTTCCTGT           4092

TCACTGGCTC ATTTCTTTAC CATTCACTCA GCATCTGCTC TGTGGAAGGC           4142

CCTGGTAGTA GTGGG                                                 4157
```

(2) INFORMATION FOR SEQ ID NO: 10:

(i) SEQUENCE CHARACTERISTICS:
(A) LENGTH: 662 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-21 gene (xi) SEQUENCE DESCRIPTION: SEQ ID NO: 10:

```
GGATCCCCAT GGATCCAGGA AGAATCCAGT TCCACCCCTG CTGTGAACCC            50

AGGGAAGTCA CGGGGCCGGA TGTGACGCCA CTGACTTGCG CGTTGGAGGT           100

CAGAGAACAG CGAGATTCTC GCCCTGAGCA ACGGCCTGAC GTCGGCGGAG           150

GGAAGCAGGC GCAGGCTCCG TGAGGAGGCA AGGTAAGATG CCGAGGGAGG           200

ACTGAGGCGG GCCTCACCCC AGACAGAGGG CCCCCAATAA TCCAGCGCTG           250

CCTCTGCTGC CAGGCCTGGA CCACCCTGCA GGGGAAGACT TCTCAGGCTC           300

AGTCGCCACC ACCTCACCCC GCCACCCCCC GCCGCTTTAA CCGCAGGGAA           350

CTCTGGTGTA AGAGCTTTGT GTGACCAGGG CAGGGCTGGT TAGAAGTGCT           400

CAGGGCCCAG ACTCAGCCAG GAATCAAGGT CAGGACCCCA AGAGGGGACT           450

GAGGGTAACC CCCCCGCACC CCCACCACCA TTCCCATCCC CCAACACCAA           500

CCCCACCCCC ATCCCCCAAC ACCAAACCCA CCACCATCGC TCAAACATCA           550
```

-continued

```
ACGGCACCCC CAAACCCCGA TTCCCATCCC CACCCATCCT GGCAGAATCG          600

GAGCTTTGCC CCTGCAATCA ACCCACGGAA GCTCCGGGAA TGGCGGCCAA          650

GCACGCGGAT CC                                                   662
```

(2) INFORMATION FOR SEQ ID NO: 11:

(i) SEQUENCE CHARACTERISTICS:
(A) LENGTH: 1640 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: cDNA MAGE-3

(xi) SEQUENCE DESCRIPTION: SEQ ID NO: 11:

```
GCCGCGAGGG AAGCCGGCCC AGGCTCGGTG AGGAGGCAAG GTTCTGAGGG           50

GACAGGCTGA CCTGGAGGAC CAGAGGCCCC CGGAGGAGCA CTGAAGGAGA          100

AGATCTGCCA GTGGGTCTCC ATTGCCCAGC TCCTGCCCAC ACTCCCGCCT          150

GTTGCCCTGA CCAGAGTCAT C                                         171

ATG CCT CTT GAG CAG AGG AGT CAG CAC TGC AAG CCT GAA GAA         213

GGC CTT GAG GCC CGA GGA GAG GCC CTG GGC CTG GTG GGT GCG         255

CAG GCT CCT GCT ACT GAG GAG CAG GAG GCT GCC TCC TCC TCT         297

TCT ACT CTA GTT GAA GTC ACC CTG GGG GAG GTG CCT GCT GCC         339

GAG TCA CCA GAT CCT CCC CAG AGT CCT CAG GGA GCC TCC AGC         381

CTC CCC ACT ACC ATG AAC TAC CCT CTC TGG AGC CAA TCC TAT         423

GAG GAC TCC AGC AAC CAA GAA GAG GAG GGG CCA AGC ACC TTC         465

CCT GAC CTG GAG TCC GAG TTC CAA GCA GCA CTC AGT AGG AAG         507

GTG GCC GAG TTG GTT CAT TTT CTG CTC CTC AAG TAT CGA GCC         549

AGG GAG CCG GTC ACA AAG GCA GAA ATG CTG GGG AGT GTC GTC         591

GGA AAT TGG CAG TAT TTC TTT CCT GTG ATC TTC AGC AAA GCT         633

TCC AGT TCC TTG CAG CTG GTC TTT GGC ATC GAG CTG ATG GAA         675

GTG GAC CCC ATC GGC CAC TTG TAC ATC TTT GCC ACC TGC CTG         717

GGC CTC TCC TAC GAT GGC CTG CTG GGT GAC AAT CAG ATC ATG         759

CCC AAG GCA GGC CTC CTG ATA ATC GTC CTG GCC ATA ATC GCA         801

AGA GAG GGC GAC TGT GCC CCT GAG GAG AAA ATC TGG GAG GAG         843

CTG AGT GTG TTA GAG GTG TTT GAG GGG AGG GAA GAC AGT ATG         885

TTG GGG GAT CCC AAG AAG CTG CTC ACC CAA CAT TTC GTG CAG         927

GAA AAC TAC CTG GAG TAC CGG CAG GTC CCC GGC AGT GAT CCT         969

GCA TGT TAT GAA TTC CTG TGG GGT CCA AGG GCC CTC GTT GAA        1011

ACC AGC TAT GTG AAA GTC CTG CAC CAT ATG GTA AAG ATC AGT        1053

GGA GGA CCT CAC ATT TCC TAC CCA CCC CTG CAT GAG TGG GTT        1095

TTG AGA GAG GGG GAA GAG TGA                                    1116

GTCTGAGCAC GAGTTGCAGC CAGGGCCAGT GGGAGGGGGT CTGGGCCAGT         1166

GCACCTTCCG GGGCCGCATC CCTTAGTTTC CACTGCCTCC TGTGACGTGA         1216
```

-continued

```
GGCCCATTCT TCACTCTTTG AAGCGAGCAG TCAGCATTCT TAGTAGTGGG          1266

TTTCTGTTCT GTTGGATGAC TTTGAGATTA TTCTTTGTTT CCTGTTGGAG          1316

TTGTTCAAAT GTTCCTTTTA ACGGATGGTT GAATGAGCGT CAGCATCCAG          1366

GTTTATGAAT GACAGTAGTC ACACATAGTG CTGTTTATAT AGTTTAGGAG          1416

TAAGAGTCTT GTTTTTTACT CAAATTGGGA AATCCATTCC ATTTTGTGAA          1466

TTGTGACATA ATAATAGCAG TGGTAAAAGT ATTTGCTTAA AATTGTGAGC          1516

GAATTAGCAA TAACATACAT GAGATAACTC AAGAAATCAA AAGATAGTTG          1566

ATTCTTGCCT TGTACCTCAA TCTATTCTGT AAAATTAAAC AAATATGCAA          1616

ACCAGGATTT CCTTGACTTC TTTG                                      1640
```

(2) INFORMATION FOR SEQ ID NO: 12:

(i) SEQUENCE CHARACTERISTICS:
(A) LENGTH: 943 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-31 gene (xi) SEQUENCE DESCRIPTION: SEQ ID NO: 12:

```
GGATCCTCCA CCCCAGTAGA GTGGGGACCT CACAGAGTCT GGCCAACCCT           50

CCTGACAGTT CTGGGAATCC GTGGCTGCGT TTGCTGTCTG CACATTGGGG          100

GCCCGTGGAT TCCTCTCCCA GGAATCAGGA GCTCCAGGAA CAAGGCAGTG          150

AGGACTTGGT CTGAGGCAGT GTCCTCAGGT CACAGAGTAG AGGGGGCTCA          200

GATAGTGCCA ACGGTGAAGG TTTGCCTTGG ATTCAAACCA AGGGCCCCAC          250

CTGCCCCAGA ACACATGGAC TCCAGAGCGC CTGGCCTCAC CCTCAATACT          300

TTCAGTCCTG CAGCCTCAGC ATGCGCTGGC CGGATGTACC CTGAGGTGCC          350

CTCTCACTTC CTCCTTCAGG TTCTGAGGGG ACAGGCTGAC CTGGAGGACC          400

AGAGGCCCCC GGAGGAGCAC TGAAGGAGAA GATCTGTAAG TAAGCCTTTG          450

TTAGAGCCTC CAAGGTTCCA TTCAGTACTC AGCTGAGGTC TCTCACATGC          500

TCCCTCTCTC CCCAGGCCAG TGGGTCTCCA TTGCCCAGCT CCTGCCCACA          550

CTCCCGCCTG TTGCCCTGAC CAGAGTCATC                                580

ATG CCT CTT GAG CAG AGG AGT CAG CAC TGC AAG CCT GAA GAA         622

GGC CTT GAG GCC CGA GGA GAG GCC CTG GGC CTG GTG GGT GCG         664

CAG GCT CCT GCT ACT GAG GAG CAG GAG GCT GCC TCC TCC TCT         706

TCT AGT GTA GTT GAA GTC ACC CTG GGG GAG GTG CCT GCT GCC         748

GAG TCA CCA GAT CCT CCC CAG AGT CCT CAG GGA GCC TCC AGC         790

CTC CCC ACT ACC ATG AAC TAC CCT CTC TGG AGC CAA TCC TAT         832

GAG GAC TCC AGC AAC CAA GAA GAG GAG GGG CCA AGC ACC TTC         874

CCT GAC CTG GAG TCT GAG TTC CAA GCA GCA CTC AGT AGG AAG         916

GTG GCC AAG TTG GTT CAT TTT CTG CTC                             943
```

(2) INFORMATION FOR SEQ ID NO: 13:

(i) SEQUENCE CHARACTERISTICS:
(A) LENGTH: 1067 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: cDNA MAGE-4

(xi) SEQUENCE DESCRIPTION: SEQ ID NO: 13:

```
GGG CCA AGC ACC TCG CCT GAC GCA GAG TCC TTG TTC CGA          39

GAA GCA CTC AGT AAC AAG GTG GAT GAG TTG GCT CAT TTT CTG      81

CTC CGC AAG TAT CGA GCC AAG GAG CTG GTC ACA AAG GCA GAA     123

ATG CTG GAG AGA GTC ATC AAA AAT TAC AAG CGC TGC TTT CCT     165

GTG ATC TTC GGC AAA GCC TCC GAG TCC CTG AAG ATG ATC TTT     207

GGC ATT GAC GTG AAG GAA GTG GAC CCC GCC AGC AAC ACC TAC     249

ACC CTT GTC ACC TGC CTG GGC CTT TCC TAT GAT GGC CTG CTG     291

GGT AAT AAT CAG ATC TTT CCC AAG ACA GGC CTT CTG ATA ATC     333

GTC CTG GGC ACA ATT GCA ATG GAG GGC GAC AGC GCC TCT GAG     375

GAG GAA ATC TGG GAG GAG CTG GGT GTG ATG GGG GTG TAT GAT     417

GGG AGG GAG CAC ACT GTC TAT GGG GAG CCC AGG AAA CTG CTC     459

ACC CAA GAT TGG GTG CAG GAA AAC TAC CTG GAG TAC CGG CAG     501

GTA CCC GGC AGT AAT CCT GCG CGC TAT GAG TTC CTG TGG GGT     543

CCA AGG GCT CTG GCT GAA ACC AGC TAT GTG AAA GTC CTG GAG     585

CAT GTG GTC AGG GTC AAT GCA AGA GTT CGC ATT GCC TAC CCA     627

TCC CTG CGT GAA GCA GCT TTG TTA GAG GAG GAA GAG GGA GTC     669

TGAGCATGAG TTGCAGCCAG GGCTGTGGGG AAGGGGCAGG GCTGGGCCAG      719

TGCATCTAAC AGCCCTGTGC AGCAGCTTCC CTTGCCTCGT GTAACATGAG      769

GCCCATTCTT CACTCTGTTT GAAGAAAATA GTCAGTGTTC TTAGTAGTGG      819

GTTTCTATTT TGTTGGATGA CTTGGAGATT TATCTCTGTT TCCTTTTACA      869

ATTGTTGAAA TGTTCCTTTT AATGGATGGT TGAATTAACT TCAGCATCCA      919

AGTTTATGAA TCGTAGTTAA CGTATATTGC TGTTAATATA GTTTAGGAGT      969

AAGAGTCTTG TTTTTTATTC AGATTGGGAA ATCCGTTCTA TTTTGTGAAT     1019

TTGGGACATA ATAACAGCAG TGGAGTAAGT ATTTAGAAGT GTGAATTC       1067
```

(2) INFORMATION FOR SEQ ID NO: 14:

(i) SEQUENCE CHARACTERISTICS:
(A) LENGTH: 226 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-5 gene (xi) SEQUENCE DESCRIPTION: SEQ ID NO: 14:

```
AGGATCCCCA GGAGGCCCTA GAGGAGCACC AAAGGAGAAG ATCTGTAAGT       50
```

-continued

```
AAGCCTTTGT TAGAGCCTCC AAGGTTCAGT TTTTAGCTGA GGCTTCTCAC          100

ATGCTCCCTC TCTCTCCAGG CCAGTGGGTC TCCATTGCCC AGCTCCTGCC          150

CACACTCCTG CCTGTTGCGG TGACCAGAGT CGTC                            184

ATG TCT CTT GAG CAG AAG AGT CAG CAC TGC AAG CCT GAG GAA          226
```

(2) INFORMATION FOR SEQ ID NO: 15:

(i) SEQUENCE CHARACTERISTICS:
(A) LENGTH: 225 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: MAGE-6 gene (xi) SEQUENCE DESCRIPTION: SEQ ID NO: 15:

```
TAT TTC TTT CCT GTG ATC TTC AGC AAA GCT TCC GAT TCC TTG           42

CAG CTG GTC TTT GGC ATC GAG CTG ATG GAA GTG GAC CCC ATC           84

GGC CAC GTG TAC ATC TTT GCC ACC TGC CTG GGC CTC TCC TAC          126

GAT GGC CTG CTG GGT GAC AAT CAG ATC ATG CCC AGG ACA GGC          168

TTC CTG ATA ATC ATC CTG GCC ATA ATC GCA AGA GAG GGC GAC          210

TGT GCC CCT GAG GAG                                              225
```

(2) INFORMATION FOR SEQ ID NO: 16:

(i) SEQUENCE CHARACTERISTICS:
(A) LENGTH: 166 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: MAGE-7 gene (xi) SEQUENCE DESCRIPTION: SEQ ID NO: 16:

```
ACA AGC ACT AGT TTC CTT GTG ATC TAT GGC AAA GCC TCA GAG           42

TGC ATG CAG GTG ATG TTT GGC ATT GAC ATG AAG GAA GTG GAC           84

CCC GCG GCC ACT CCT ACG TCT TGT ACC TGC TTG GGC CTC TCC          126

TAC AAT GGC CTG CTG GGT GAT GAT CAG AGC ATG CCC GAG A            166
```

(2) INFORMATION FOR SEQ ID NO: 17

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: complementary DNA (xi) SEQUENCE DESCRIPTION: SEQ ID NO: 17

```
ACTCAGCTCC TCCCAGATTT                                             20
```

(2) INFORMATION FOR SEQ ID NO: 18

-continued

```
     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (ii) MOLECULE TYPE: complementary DNA

    (xi) SEQUENCE DESCRIPTION: SEQ ID NO: 18

GAAGAGGAGG GGCCAAG                                                  17


(2) INFORMATION FOR SEQ ID NO: 19

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

    (ii) MOLECULE TYPE: complementary DNA

    (xi) SEQUENCE DESCRIPTION: SEQ ID NO: 19

TCTTGTATCC TGGAGTCC                                                 18


(2) INFORMATION FOR SEQ ID NO: 20

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

    (ii) MOLECULE TYPE: complementary DNA

    (xi) SEQUENCE DESCRIPTION: SEQ ID NO: 20

TTGCCAAGAT CTCAGGAA                                                 18


(2) INFORMATION FOR SEQ ID NO: 21

     (i) SEQUENCE CHARACTERISTICS:
          (A) LENGTH: 15 amino acids
          (B) TYPE: amino acid
          (D) TOPOLOGY: linear

    (xi) SEQUENCE DESCRIPTION: SEQ ID NO: 21

Asp Val Lys Glu Ala Asp Pro Thr Gly His Ser Tyr Val Leu Val
                5                   10                  15
```

We claim:

1. An isolated nucleic acid molecule which codes for the MAGE tumor rejection antigen precursor as set forth in SEQ. ID. NO. 8.

2. The isolated nucleic acid molecule of claim 1, wherein said nucleic acid is a DNA cDNA molecule which comprises nucleotides 3881 to 4711 of SEQ. ID. NO. 8.

3. An isolated mRNA molecule which is complementary to the nucleic acid molecule of claim 1.

[4. An isolated nucleic acid molecule which hybridizes to the nucleic acid molecule which codes for the MAGE-1 tumor rejection antigen precursor as set forth in SEQ ID No: 8 under stringent conditions and which codes for a tumor rejection precursor.]

5. A expression vector comprising the isolated nucleic acid molecule of claim 1 operably linked to a promoter.

6. The expression vector of claim 5, wherein said promoter is an incurable promoter.

7. An expression vector comprising the isolated nucleic acid molecule of claim 2 operably linked to a promoter.

8. The expression vector of claim 7, wherein said promoter is an inducible promoter.

[9. An expression vector comprising the isolated nucleic acid molecule of claim 4 operably linked to a promoter.]

[10. The expression vector of claim 9, wherein said promoter is an inducible promoter.]

11. A host cell transfected with the nucleic acid molecule of claim 1.

12. The host cell of claim 11, wherein said host cell is a mammalian cell.

13. The host cell of claim 12, wherein said cell line is a fibroblast cell line.

14. A host cell line transfected with the nucleic acid molecule of claim 2.

[15. A host cell line transfected with the nucleic acid molecule of claim 4.]

[16. The hose cell of claim 15, wherein MAGE 1 has the nucleic acid sequence as follows:

```
   1 GGATCCAGGC CCTGCCAGGA AAAATATAAG GGCCCTGCGT GAGAACAGAG GGGGTCATCC   60
  61 ACTGCATGAG AGTGGGGATG TCACAGAGTC CAGCCCACCC TCCTGGTACG ACTGAGAAGC  120
 121 CAGGGCTGTG CTTGCGGTCT GCACCCTGAG GGCCCGTGGA TTCCTCTTCC TGGAGCTCCA  180
 181 GGAACCAGGC AGTGAGGCCT TGGTCTGAGA CAGTATCCTC AGGTCACAGA GCAGAGGATG  240
 241 CACAGGGTGT GCCAGCAGTG AATGTTTGCC CTGAATGCAC ACCAAGGGCC CCACCTGCCA  300
 301 CAGGACACAT AGGACTCCAC AGAGTCTGGC CTCACCTCCC TACTGTCAGT CCTGTACAAT  360
 361 CGACCTCTGC TGGCCGGCTG TACCCTGAGT ACCCTCTCAC TTCCTCCTTC AGGTTTTCAG  420
 421 GGGACAGGCC AACCCAGAGG ACAGGATTCC CTGGAGGCCA CAGAGGAGCA CCAAGGAGAA  480
 481 GATCTGTAAG TAGGCCTTTG TTAGAGTCTC CAAGGTTCAG TTCTCAGCTG AGGCCTCTCA  540
 541 CACACTCCCT CTCTCCCCAG GCCTGTGGGT CTTCATTGCC CAGCTCCTGC CCACACTCCT  600
 601 GCCTGCTGCC CTGACGAGAG TCATCATGTC TCTTGAGCAG AGGAGTCTGC ACTGCAAGCC  660
 661 TGAGGAAGCC CTTGAGGCCC AACAAGAGGC CCTGGGCTGG TGTGTGTGCA GGCTGCCACC  720
 721 TCCTCCTCCT CTCCTCTGGT CCTGGGCACC CTGGAGGAGG TGCCCACTGC TGGGTCAACA  780
 781 GATCCTCCCC AGAGTCCTCA GGGAGCCTCC GCCTTTCCCA CTACCATCAA CTTCACTCGA  840
 841 CAGAGGCAAC CCAGTGAGGG TTCCAGCAGC CGTGAAGAGG AGGGGCCAAG CACCTCTTGT  900
 901 ATCCTGGAGT CCTTGTTCCG AGCAGTAATC ACTAAGAAGG TGGCTGATTT GGTTGGTTTT  960
 961 CTGCTCCTCA AATATCGAGC CAGGGAGCCA GTCACAAAGG CAGAAATGCT GGAGAGTGTC 1020
1021 ATCAAAAATT ACAAGCACTG TTTTCCTGAG ATCTTCGGCA AAGCCTCTGA GTCCTTGCAG 1080
1081 CTGGTCTTTG GCATTGACGT GAAGGAAGCA GACCCCACCG GCCACTCCTA TGTCCTTGTC 1140
1141 ACCTGCCTAG GTCTCTCCTA TGATGGCCTG CTGGGTGATA ATCAGATCAT GCCCAAGACA 1200
1201 GGCTTCCTGA TAATTGTCCT GGTCATGATT GCAATGGAGG GCGGCCATGC TCCTGAGGAG 1260
1261 GAAATCTGGG AGGAGCTGAG TGTGATGGAG GTGTATGATG GGAGGGAGCA CAGTGCCTAT 1320
1321 GGGGAGCCCA GGAAGCTGCT CACCCAAGAT TTGGTGCAGG AAAAGTACCT GGAGTACGGC 1380
1381 AGGTGCCGGA CAGTGATCCC GCACGCTATG AGTTCCTGTG GGGTCCAAGG GCCCTCGCTG 1440
1441 AAACCAGCTA TGTGAAAGTC CTTGAGTATG TGATCAAGGT CAGTGCAAGA GTTCGCTTTT 1500
1501 TCTTCCCATC CCTGCGTGAA GCAGCTTTGA GAGAGGAGGA AGAGGGAGTC TGAGCATGAG 1560
1561 TTGCAGCCAA GGCCAGTGGG AGGGGGACTG GGCCAGTGCA CCTTCCAGGG CCGCGTCCAG 1620
1621 CAGCTTCCCC TGCCTCGTGT GACATGAGGC CCATTCTTCA CTCTGAAGAG AGCGGTCAGT 1680
1681 GTTCTCAGTA GTAGGTTTCT GTTCTATTGG GTGACTTGGA GATTTATCTT TGTTCTCTTT 1740
1741 TGGAATTGTT CAAATGTTTT TTTTTAAGGG ATGGTTGAAT GAACTTCAGC ATCCAAGTTT 1800
1801 ATGAATGACA GCAGTCACAC AGTTCTGTGT ATATAGTTTA AGGGTAAGAG TCTTGTGTTT 1860
1861 TATTCAGATT GGGAAATCCA TTCTATTTTG TGAATTGGGA TAATAACAGC AGTGGAATAA 1920
1921 GTACTTAGAA ATGTGAAAAA TGAGCAGTAA AATAGATGAG ATAAAGAACT AAAGAAATTA 1980
1981 AGAGATAGTC AATTCTTGCC TTATACCTCA GTCTATTCTG TAAAATTTTT AAAGATATAT 2040
2041 GCATACCTGG ATTTCCTTGG CTTCTTTGAG AATGTAAGAG AAATTAAATC TGAATAAAGA 2100
2101 ATTCTTCCTG TTCACTGGCT CTTTTCTTCT CCATGCACTG AGCATCTGCT TTTTGGAAGG 2160
2161 CCCTGGGTTA GTAGTGGAGA TGCTAAGGTA AGCCAGACTC ATACCCACCC ATAGGGTCGT 2220
2221 AGAGTCTAGG AGCTGCAGTC ACGTAATCGA GGTGGCAAGA TGTCCTCTAA AGATCTAGGG 2280
```

-continued

```
2281 AAAAGTGAGA GAGGGGTGAG GGTGTGGGGC TCCGGGTGAG AGTGGTGGAG TGTCAATGCC 2340

2341 CTGAGCTGGG GCATTTTGGG CTTTGGGAAA CTGCAGTTCC TTCTGGGGGA GCTGATTGTA 2400

2401 ATGATCTTGG GTGGATCC                                               2418
```

]

17. The host cell of claim 14, wherein said host cell is a mammalian cell.

[18. The host cell of claim 15, wherein said host cell is a mammalian cell.]

*19. An isolated nucleic acid molecule which hybridizes to the nucleic acid molecule which codes for the MAGE-1 tumor rejection antigen precursor as set forth in SEQ ID NO: 8 at 0.1×SSC, 0.1% SDS, and which codes for a tumor rejection antigen precursor.*

*20. An expression vector comprising the isolated nucleic acid molecule of claim 19, operably linked to a promoter.*

*21. The expression vector of claim 20, wherein said promoter is an inducible promoter.*

*22. A host cell transfected with the insolated nucleic acid molecule of claim 19.*

*23. The host cell of claim 22, wherein said isolated nucleic acid molecule has the nucleotide sequence of SEQ ID NO: 7.*

*24. The host cell of claim 22, wherein said host cell is a mammalian cell.*

*25. A host cell transfected with an isolated nucleic acid molecule which hybridizes to the nucleic acid molecule which codes for the MAGE-1 tumor rejection antigen precursor as set forth in SEQ ID NO: 8 at 0.1×SSC, 0.1% SDS and which codes for a tumor rejection antigen precursor.*

* * * * *